US007429586B2

(12) United States Patent
Apodaca et al.

(10) Patent No.: US 7,429,586 B2
(45) Date of Patent: Sep. 30, 2008

(54) NON-IMIDAZOLE ARYLOXYALKYLAMINES

(75) Inventors: Richard Apodaca, San Diego, CA (US); Nicholas I. Carruthers, Poway, CA (US); Curt A. Dvorak, San Diego, CA (US); Dale A. Rudolph, San Diego, CA (US); Chandravadan R. Shah, San Diego, CA (US); Wei Xiao, San Diego, CA (US)

(73) Assignee: Ortho-McNeil Pharmaceuticlas, Inc., Raritan, NJ (US)

( * ) Notice: Subject to any disclaimer, the term of this patent is extended or adjusted under 35 U.S.C. 154(b) by 0 days.

(21) Appl. No.: 11/453,422

(22) Filed: Jun. 15, 2006

(65) Prior Publication Data

US 2006/0235049 A1    Oct. 19, 2006

Related U.S. Application Data

(62) Division of application No. 09/922,631, filed on Aug. 6, 2001, now Pat. No. 7,186,732.

(60) Provisional application No. 60/223,768, filed on Aug. 8, 2000.

(51) Int. Cl.
*A61K 31/435*    (2006.01)
*C07D 217/00*    (2006.01)

(52) U.S. Cl. ............... 514/235.5; 546/139; 548/571

(58) Field of Classification Search ............... 514/235.5; 546/139

See application file for complete search history.

(56) References Cited

U.S. PATENT DOCUMENTS

| | | | |
|---|---|---|---|
| 3,919,231 A | 11/1975 | Pelosi | |
| 4,833,149 A | 5/1989 | Press | |
| 5,182,291 A | 1/1993 | Gubin et al. | |
| 5,217,986 A | 6/1993 | Pomponi et al. | |
| 5,352,707 A | 10/1994 | Pompni et al. | |
| 5,580,523 A | 12/1996 | Bard | |
| 5,580,883 A | 12/1996 | Goto et al. | |
| 5,840,746 A | 11/1998 | Ducharme | |
| 5,869,479 A | 2/1999 | Kreutner | |
| 5,883,096 A | 3/1999 | Lowe | |
| 5,929,089 A | 7/1999 | Jegham | |
| 6,638,967 B2 | 10/2003 | Bogenstaetter et al. | |
| 6,821,980 B1 * | 11/2004 | Guerry et al. | 514/275 |
| 7,071,191 B2 | 7/2006 | Apodaca | |
| 7,241,778 B2 * | 7/2007 | Apodaca et al. | 514/316 |

FOREIGN PATENT DOCUMENTS

| | | |
|---|---|---|
| DE | 19920161 | 5/2000 |
| EP | 0978512 | 2/2000 |
| EP | 982300 | 3/2000 |
| WO | 93/20061 | 10/1993 |
| WO | 95/04052 | 2/1995 |
| WO | 95/14007 | 5/1995 |
| WO | 97/17345 | 5/1997 |
| WO | 99/00186 | 1/1999 |
| WO | 99/42458 | 8/1999 |
| WO | 00/06254 | 2/2000 |
| WO | 00/51720 | 9/2000 |
| WO | 01/32633 A1 | 5/2001 |
| WO | 01/89681 | 11/2001 |

OTHER PUBLICATIONS

Albengres, E. et al.; "Systemic Antifungal Agents"; Drug Safety; Feb. 1998; 18(2) :83-97.
Ali, S.M. et al, "Design, Synthesis, and Structure-Activity Relationships of Acetylene-Based Histamine H3 Receptor Antagonists"; J. Med. Chem. ; 1999 42:903-909.
Arrang, J.M. et al; "Auto-inhibition of brain histamine release mediated by a novel class (h3) of histamine receptor" Nature; Apr. 1983: 302:832-837.
Ash, A.S.F. et al; "Receptors Mediating Some Actions of Histamine"; Br. J. Pharmac. Chemother.; 1966 27:427-439.
Back, D.J.; et al; "Inhibition of tolbutamide metabolism by substituted imidazole drugs in vivo:evidence for a structure-activity relationship"; Br. J. Pharmacol.; 1985 85:121-126.
Barnes, J.C. et al; "The selective Histamine H3 Receptor Antagonist Thioperamide Improves Cognition and Enhances Hippocampal Acetylcholine Release in vivo"; Soc. Neurosci. Abstr.; 1993 19:1813.
Black, J.W. et al.; "Definition and Antagonism of Histamine H2-receptors"; Nature. Apr. 1972; 236:385-390.
Caplus English Abstract WO 2001032633 Guerry et al 2001.* Holger Stark et al.: Developments of histamine H3-antagonists, Drugs of the Future, 1996, pp. 507-520, vol. 21, No. 5, XP002084872 Barcelona, ES ISSN: 0377-8282.
Cui, T. et al.: "Fabrication of microreactors for dehydrogenation of cyclohexane to benzene", Sensors and Actuators B., Elsevier Sequoia S.A., Lausanne, CH, Gd 71, Nr. 3, Dec. 1, 2000, XP004223421.
Ganellin, C.R. et al.: "Synthesis of potent Non-imidazole Histamine H3-Receptor Antagonists" Archiv Der Pharmazie., vol. 331, 1998, pp. 395-404, XP002123596 VCH Verlagsgesellschaft mbH, Weinheim., De ISSN: 0365-6233 cited in the application.
Garbag, M. et al; "S-[2-(4-Imidazolyl)ethyl] Isothiourea, a Highly Specific and Potent Histamine H3 Receptor Agonist"; J. Pharmacol. Exp. Ther.; 1992; 263(1):304-310.
Gilatech, Inc.; "Other News to Note"; Bioworls Today, Mar. 2, 199, p. 3.
Gilatech, Inc.; "Gilatech's first drug candidate begins phase I human clinical trials"; Gilatech Inc. Press Release; Nov. 5, 1998.
Greene Protective Groups in Organic Synthesis (1981).
Ichinose, M. et al; "Histamine H3-receptors modulate nonadrenergic noncholinergic neural bronchoconstriction in guinea-pig in vivo"; P.J. Eur. J. Pharmacol; 1989; 174:49-55.

(Continued)

*Primary Examiner*—Kamal A. Saeed

(57) ABSTRACT

Substituted aryloxyalkylamines of formula (I), compositions containing them, and methods of making and using them to treat histamine-mediated conditions.

7 Claims, No Drawings

OTHER PUBLICATIONS

Imamura, M. et al.; "Unmasking of Activated Histamine H3-Receptors in Myocardial Ischemia: Their Role as Regulators of Exocytotic Norepinephrine Release 1,2"; J. Pharmacol, Exp. ther.; 1994; 271(3):1259-1266.

Kapetanovic, I.M. et al; "Nafimidone, An Imidazole Anticonvulsant, and its Metabolite as Potent Inhibitors of Microsomal Metabolism of Phenytoin and Carbamazepine"; H. J. Drug Metab. Dispos.; 1984 12(5) :560-564.

Korte, A. et al; "Characterization and Tissue Distribution of H3 Histamine Receptors in Guinea Pigs by Na-Methylhistamine"; Biochem. Biophys. Res. Commun.; May 1990; 168(3) :979-986.

Krause, M. et al.; "The Histamine H3 Receptor-A Target for New Drugs"; Leurs, R.; Timmerman, H. (Eds.); Elsevier; 1998;175-196.

Lavrijsen, K. et al; "Induction Potential of Antifungals Containing and Imidazole or Triazole Moiety"; Biochem. Pharmacol.; 1986 35 (11):1867-1878.

Leurs, R. et al; "The medicinal chemistry and therapeutic potentials of ligands of the histamine h3 receptor" Prog. Drug. Res.; 1995; 45:107-165.

Lin, Jiang-Sheng et al. "Involvement of histaminergic neurons in arousaol mechanisms demonstrated with H3-receptor ligands in the cat"; Brain Res.; 1990; 523:325-330.

Linney, Ian D. et al.: "Design, synthesis, and Structure-Activity Relationships of novel Non-imidazole Histamine H3 receptor Antagonists" Journal of Medicinal Chemistry., vol. 43, No. 12, May 20, 2000 (May 20, 2000), pp. 2362-2370, XP001019293 American Chemical Society., US ISSN: 0022-2623 cited in the application.

Lovenberg, T.W. et al; "Cloning and Functional Expression of the Human Histamine H3 Receptor"; Mol. Pharmacol; 1999 55:1101-1107.

Machidori, H. et al; "Zucker obese rats:defect in brain histamine control of feeding"; Brain Res.; 1992; 590:180-186.

McLeod, R.L. et al; "Antimigraine and Sedative Activity of SCH 50971: A Novel Orally-Active Histamine H3 Receptor Agonist"; Soc. Neurosci, Abstr.; 1996; 22:2010.

Meier, G. et al.; "Influence of imidazole replacement in different structural classes of histamine H3-receptor antagonists"; Eur. J. Pharm. Sci.; 2001 13:249-259.

Monti, J.M. et al; "Effects of selective activation or blockade of the histamine h3 receptor on sleep and wakefulness"; Eur. J. Pharmacol.; 1991; 205:283-287.

Morisset, S. et al; "High constitutuive activity of native H3 receptors regulates histamine neurons in brain"; Nature; Dec., 2000; 408:860-864.

Oda, Tamaki et al.; "Molecular Cloning and characterization of a Novel Type of Histamine Receptor Preferentially Expressed in Leukocytes"; J. Biol. Chem.; Nov. 2000; 275(47):36781-36786.

Panula, P. et al.; "Significant Changes in the Human Brain Histaminergic System in Alzheimer's Disease"Soc. Neurosci. Abstr.; 1995; 21:1977.

Phillips, J. G. et al; "The Histamine H3 Receptor-A Target for New Drugs"; Leurs, R.; Timmerman, H. (eds.); Elsevier; 1998; 197-222.

Rouleau, A. et al.; "Bioavailability, Antinociceptive and Antiinflammatory Properties of BP 2-94, a Histamine H3 Receptor Agonist Prodrug"; J. Pharmacol. Exp. Ther.; 1997 281(3) :1085-1094.

Schlicker, E., et al; "The moderate affinity of clozapine at H3 receptors is not shared by its two major metab oiltes and by structurally related and unrelated atypical neuroleptics"; Naunyn-Schmiedeberg's Arch. Pharmacol.; 1996 353:290-294.

Sheets, Joel J., et al.; "Ketoconazole: A Potent Inhibitor of Cytochrome P-450Dependent Drug Metabolism in Rat Liver", Drug Metab. Dispos.; 1984 12(5) :603-606.

Starks, H. et al.: "Developments of histamine H3- antagonists" Drugs of the Future, vol. 21, No. 5, 1996, pp. 507-520, XP002084872 Barcelona, ES ISSN: 0377-8282 cited in the application.

Starke, H. et al.: "General Construction Patterb of Histamine H3-Receptor Antagonists: Change of a paradigm" Bioorganic & Medicinal Chemistry Letters, No. 8, 1998, pp. 2011-2016, XP004137177 Oxford, GB ISSN: 0960-894X.

Tozer, M.J., et al.: "Histamine H3 receptor antagonists" Exp. Opinion. Ther. Patents; 2000 10:1045-1055.

Walczynski, K. et al, "Non-Imidazole Histamine H3 Ligands, Part 2: New 2-Substituted Benzothiazoles as Histamine H3 Antagonists"; Arch. Pharm. Pharm. Med. Chem (Weinheim, Ger.); 1999 332:389-398.

Walczynski, K. et al.; "Non-imidazole histamine H3 ligands. Part I. Synthesis of 2-(1-piperazinyl)-and 2-hexahydro-1 H-1,4-diazepin-1-yl0 benzoyhiazole derivatives as H3 antagonists with H1 blocking activities"; IL Farmaco; 1999; 54:684-694.

West, R.E. Jr. et al.; "The Profiles of Human and Primate [3H] Na-Methylhistamoine Binding Differ From That of Rodents"; Eur. J. Pharmacol.; 1999; 377:233-239.

Wolin, Ronald et al.: Novel H3 Receptor Antagonists. Sulfonamide Homologs of Histamine; Bioorganic & Medicinal Chemistry Letters, 1998, pp. 2157-2162, No. 8; XP004137238, GB ISSN: 0960-894X.

Yokohama, H. et al., "Effect of thioperamide, a histamine h3 receptor anatgonist, on electrically induced convulsions in mice"; Eur. J. Pharmacol. ; 119 234:129-133 1993.

* cited by examiner

NON-IMIDAZOLE ARYLOXYALKYLAMINES

This Application is a Divisional of U.S. application Ser. No. 09/922,631, filed Aug. 6, 2001, now U.S. Pat. No. 7,186,732 which claims priority to U.S. Provisional Application No. 60/223,768, filed Aug. 8, 2000, both of which are incorporated herein by reference in their entirety.

The complete disclosures of the aforementioned related U.S. patent applications are hereby incorporated by reference for all purposes.

FIELD OF THE INVENTION

The present invention relates to aryloxyalkylamines, their synthesis and their use, for example, for the treatment of disorders and conditions mediated by the histamine receptor.

BACKGROUND OF THE INVENTION

Histamine [2-(imidazol-4-yl)ethylamine] is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the $H_1$ receptor (Ash, A. S. F. and Schild, H. O., *Br. J. Pharmacol.*, 1966, 27, 427).and are blocked by the classical antihistamines (e.g. diphenhydramine). Histamine is also an important regulator of gastric acid secretion through its action on parietal cells. These effects of histamine are mediated via the $H_2$ receptor (Black, J. W., Duncan, W. A. M., Durant, C. J., Ganellin, C. R. and Parsons, E. M., *Nature*, 1972, 236, 385) and are blocked by $H_2$ receptor antagonists (e.g. cimetidine). The third histamine receptor —$H_3$— was first described as a presynaptic autoreceptor in the central nervous system (CNS) (Arrang, J.-M., Garbarg, M., and Schwartz, J.-C., *Nature* 1983, 302, 832) controlling the synthesis and release of histamine. Recent evidence has emerged showing that the $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently there are many potential therapeutic applications for histamine $H_3$ agonists, antagonists, and inverse agonists. (See: "*The Histamine $H_3$ Receptor-A Target for New Drugs*", Leurs, R., and Timmerman, H., (Editors), Elsevier, 1998; Morisset et al., *Nature*, 2000, 408, 860-864.) A fourth histamine receptor —$H_4$— was recently described by Oda et al., (J. Biol. Chem., 2000, 275, 36781-36786).

The potential use of histamine $H_3$ agonists in sleep/wake and arousal/vigilance disorders is suggested based on animal studies (Lin et al, *Br. Res.*, 1990, 523, 325; Monti et al *Eur. J. Pharmacol.*, 1991, 205, 283). Their use in the treatment of migraine has also been suggested (McLeod et al *Abstr. Society Neuroscience*, 1996, 22, 2010) based on their ability to inhibit neurogenic inflammation. Other applications could be a protective role in myocardial ischemia and hypertension where blockade of norepinephrine release is beneficial (Imamura et al *J. Pharmacol. Expt Ther.*, 1994, 271, 1259). It has been suggested that histamine $H_3$ agonists may be beneficial in asthma due to their ability to reduce non-adrenergic non-cholinergic (NANC) neurotransmission in airways and to reduce microvascular leakage (Ichinose et al *Eur. J. Pharmacol.*, 1989, 174, 49).

Several indications for histamine $H_3$ antagonists and inverse agonists have similarly been proposed based on animal pharmacology experiments with known histamine $H_3$ antagonists (e.g. thioperamide). These include dementia, Alzheimer's disease (Panula et al *Abstr. Society Neuroscience*, 1995, 21, 1977), epilepsy (Yokoyama et al *Eur. J. Pharmacol.*, 1993, 234, 129) narcolepsy, eating disorders (Machidori et al *Brain Research* 1992, 590, 180), motion sickness, vertigo, attention deficit hyperactivity disorders (ADHD), learning and memory (Barnes et al *Abstr. Society Neuroscience*, 1993, 19, 1813), schizophrenia (Schlicker et al *Naunyn-Schmiedeberg's Arch. Pharmacol.*, 1996, 353, 290-294); (also see; Stark et al *Drugs Future*, 1996, 21, 507 and Leurs et al *Progress in Drug Research*, 1995, 45, 107 and references cited therein). Histamine $H_3$ antagonists, alone or in combination with a histamine $H_1$ antagonist, are reported to be useful for the treatment of upper airway allergic response (U.S. Pat. Nos. 5,217,986; 5,352,707 and 5,869,479). Recently, a histamine $H_3$ antagonist (GT-2331) was identified and is being developed by Gliatech Inc. (Gliatech Inc. Press Release Nov. 5, 1998; *Bioworld Today*, Mar. 2, 1999) for the treatment of CNS disorders.

As noted, the prior art related to histamine $H_3$ ligands has been comprehensively reviewed ("*The Histamine $H_3$ Receptor-A Target for New Drugs*", Leurs, R., and Timmerman, H., (Editors), Elsevier, 1998). Within this reference the medicinal chemistry of histamine $H_3$ agonists and antagonists was reviewed (see Krause et al and Phillips et al respectively). The importance of an imidazole moiety containing only a single substitution in the 4 position was noted together with the deleterious effects of additional substitution on activity. Particularly methylation of the imidazole ring at any of the remaining unsubstituted positions was reported to strongly decrease activity. Additional publications support the hypothesis that an imidazole function is essential for high affinity histamine $H_3$ receptor ligands (See, Ali et al *J. Med. Chem.*, 1999, 42, 903 and Stark et al, *Drugs Future*, 1996, 21, 507 and references cited therein). However many imidazole containing compounds are substrates for histamine methyl transferase, the major histamine metabolizing enzyme in humans, which leads to shortened half lives and lower bioavailability (See, Rouleau et al *J. Pharmacol. Exp. Ther.* 1997, 281, 1085). In addition, imidazole containing drugs, via their interaction with the cytochrome P450 monooxygenase system, can result in unfavorable biotransformations due to enzyme induction or enzyme inhibition. (Kapetanovic et al *Drug Metab. Dispos.* 1984, 12, 560; Sheets et al *Drug Metab. Dispos.* 1984, 12, 603; Back, et al *Br. J. Pharmacol.* 1985, 85, 121; Lavrijsen et al *Biochem. Pharmacol.* 1986, 35, 1867; *Drug Saf.*, 1998, 18, 83). The poor blood brain barrier penetration of earlier histamine $H_3$ receptor ligands may also be associated with the imidazole fragment (Ganellin et al *Arch. Pharm.* (*Weinheim, Ger.*) 1998, 331, 395).

More recently, several publications have described histamine $H_3$ ligands that do not contain an imidazole moiety. For example; Ganellin et al *Arch. Pharm.* (*Weinheim, Ger.*) 1998, 331, 395; Walczynski et al *Arch. Pharm.* (*Weinheim, Ger.*) 1999, 332, 389; Walczynski et al Farmaco 1999, 684; Linney et al *J. Med. Chem.* 2000, 2362; Tozer and Kalindjian *Exp. Opin. Ther. Patents* 2000, 10, 1045-1055; U.S. Pat. No. 5,352,707; PCT Application WO99/42458, Aug. 26, 1999; and European Patent Application 0978512, Feb. 9, 2000.

The compounds of the present invention do not contain the imidazole moiety, and its inherent liabilities, and maintain potency at the human $H_3$ receptor. Thus in the present invention receptor binding was determined using the human histamine $H_3$ receptor (See Lovenberg et al *Mol. Pharmacol.*

1999, 1107). Screening using the human receptor is particularly important for the identification of new therapies for the treatment-of human disease. Conventional binding assays for example are determined using rat synaptosomes (Garbarg et al *J. Pharmacol. Exp. Ther.* 1992, 263, 304), rat cortical membranes (West et al *Mol. Pharmacol.* 1990, 610), and guinea pig brain (Korte et al Biochem. *Biophys. Res. Commun.* 1990, 978). Only limited studies have been performed previously using human tissue but these allude to significant differences in the pharmacology of rodent and primate receptors (West et al *Eur. J. Pharmacol.* 1999, 233).

We now describe a series of aryloxyalkylamines with the ability to modulate the activity of the histamine receptor, specifically the $H_3$ receptor, without the inherent problems associated with the presence of an imidazolyl moiety.

SUMMARY OF THE INVENTION

The present invention is directed to a compound of formula (I):

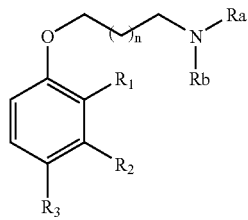

wherein $R_a$ and $R_b$ are independently $C_{1-8}$ alkyl, $C_{3-8}$ alkenyl, $C_{3-8}$ cycloalkyl, ($C_{3-8}$ cycloalkyl) $C_{1-6}$ alkyl, or taken together with the nitrogen to which they are attached form a 4-7 membered heterocyclyl optionally including up to 3 additional heteroatoms;

n is 0-4;

one of $R_1$, $R_2$, and $R_3$ is G, and the remaining two are hydrogen or halo;

G is a nitrogen-containing group selected from one of the following:

—$OL_1Q$, -$L_2Q$, —$N(L_1Q)R_5$, -$L_3C(L_1Q)R_6R_7$, —$C(L_1Q)R_6R_7$,

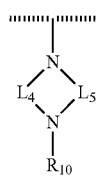

(i)

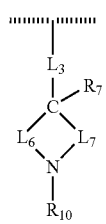

(ii)

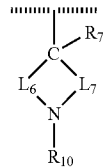

(iii)

wherein:

$L_1$ is $C_{2-6}$ alkylene, $C_{3-8}$ cycloalkylene, $C_{4-6}$ alkenylene, $C_{4-6}$ alkynylene, $C_{2-5}$ alkanoyl, (phenyl)$C_{1-6}$ alkylene, (naphthyl)$C_{1-6}$ alkylene, ($C_{2-5}$ heteroaryl)$C_{1-6}$ alkylene, (phenoxy)$C_{1-6}$ alkylene, or ($C_{2-5}$ heteroaryloxy)$C_{1-6}$ alkylene;

$L_2$ is $C_{1-6}$ alkylene, $C_{3-8}$ cycloalkylene, $C_{3-6}$ alkenylene, $C_{3-6}$ alkynylene, $C_{2-5}$ alkanoyl, (phenyl)$C_{1-6}$ alkylene, (naphthyl)$C_{1-6}$ alkylene, ($C_{1-5}$ heteroaryl)$C_{1-6}$ alkylene, (phenoxy)$C_{1-6}$ alkylene, ($C_{1-5}$ heteroaryloxy)$C_{1-6}$ alkylene, or ($C_{1-5}$ heteroarylthio)$C_{1-6}$ alkylene;

$L_3$ is $C_{1-6}$ alkylene, $C_{2-6}$ alkenylene, $C_{2-6}$ alkynylene, $C_{2-5}$ alkanoyl, (phenyl)$C_{1-6}$ alkylene, phenyl, naphthyl, (naphthyl)$C_{1-6}$ alkylene, $C_{1-5}$ heteroaryl)$C_{1-6}$ alkylene, (phenoxy)$C_{1-6}$ alkylene, ($C_{1-5}$ heteroaryloxy)$C_{1-6}$ alkylene, or $C_{2-5}$ heteroaryl;

$L_4$ is $C_{1-5}$ alkylene;

$L_5$ is $C_{1-5}$ alkylene;

$L_6$ is $C_{1-5}$ alkylene;

$L_7$ is $C_{1-5}$ alkylene or absent;

Q is —$NR_8R_9$ or a non-aromatic $C_{2-15}$ heterocyclyl ring system containing at least one nitrogen atom and optionally between 1 and 3 additional heteroatoms selected from O, S, and N in each ring;

each of $R_5$ and $R_6$ is independently selected from hydrogen, $C_{1-8}$ alkyl, $C_{2-8}$ alkenyl, $C_{3-7}$ cycloalkyl, ($C_{3-7}$ cycloalkyl)$C_{1-6}$ alkylene, $C_{2-15}$ heterocyclyl and ($C_{2-7}$ heterocyclyl)$C_{1-6}$ alkylene;

$R_7$ is H, hydroxyl, halo, $C_{2-6}$ alkoxy or absent where the carbon linking $L_6$ and $L_7$ (or bonded to $R_6$) participates in a double bond;

each of $R_8$ and $R_9$ is independently selected from hydrogen, $C_{1-8}$ alkyl, $C_{3-8}$ alkenyl, $C_{3-7}$ cycloalkyl, ($C_{3-7}$ cycloalkyl)$C_{1-6}$ alkylene, $C_{2-15}$ heterocyclyl, phenyl, ($C_{2-15}$ heterocyclyl)$C_{1-6}$ alkylene, and (phenyl)$C_{1-6}$ alkylene;

$R_{10}$ is H, $C_{1-8}$ alkyl, $C_{3-8}$ alkenyl, $C_{3-7}$ cycloalkyl, ($C_{3-7}$ cycloalkyl)$C_{1-6}$ alkylene, ($C_{2-15}$ heterocyclyl)$C_{1-6}$ alkylene, or (phenyl) $C_{1-6}$ alkylene;

wherein each of the above alkyl, alkylene, alkenyl, alkenylene, alkynyl, alkynylene, heterocyclyl, cycloalkyl, and aryl groups may each be independently and optionally substituted with between 1 and 3 substituents selected from halo, amino, nitro, hydroxyl, and $C_{1-3}$ alkyl;

wherein substituents of Q can be further selected from carboxamide, $C_{2-6}$ alkyl, $C_{1-8}$ heterocyclyl, $N(C_{1-6}$ alkyl)($C_{1-8}$ heterocyclyl), $NH(C_{1-8}$ heterocyclyl), ($C_{1-8}$ heterocyclyl) $C_{1-3}$ alkylene, $O(C_{1-8}$ heterocyclyl), $C_{1-6}$ alkoxy, (phenyl)$C_{3-6}$ cycloalkyl-O—, phenyl, (phenyl) $C_{1-3}$ alkylene, $N(C_{1-6}$ alkyl)[(phenyl)$C_{1-3}$ alkylene], and (phenyl)$C_{1-3}$ alkylene-O— where each of above heterocyclyl, phenyl, and alkyl groups may be optionally substituted with from 1 to 3 substituents independently selected from halogen, nitro, cyano, and $C_{1-3}$ alkyl;

or a pharmaceutically acceptable salt, ester, or amide thereof.

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or combination of differently formulated active agents).

The invention also provides methods of treating certain conditions and diseases, each of which methods includes administering a therapeutically effective (or jointly effective) amount of a compound or composition of the invention to a subject in need of such treatment. The disclosed compounds are useful in methods for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. For example, the invention features methods for preventing, inhibiting the progression of, or treating upper airway allergic response, asthma, itch, nasal congestion and allergic rhinitis.

In yet another embodiment, the disclosed compounds may be used in a combination therapy method including administering a jointly effective dose of an $H_3$ antagonist and administering a jointly effective dose of a histamine $H_1$ antagonist, such as loratidine (CLARITIN™), desloratidine (CLARINEX™), fexofenadine (ALLEGRA™) and cetirizine (ZYRTEC™), for the treatment of allergic rhinitis, nasal congestion, and allergic congestion.

In yet another embodiment, the disclosed compounds may be used in a combination therapy method, including administering a jointly effective dose of an $H_3$ antagonist and administering a jointly effective dose of a neurotransmitter re-uptake blocker, such as a selective serotonin re-uptake inhibitor (SSRI) or a non-selective serotonin, dopamine or norepinephrine re-uptake inhibitor, including fluoxetine (PROZAC™), sertraline (ZOLOFT™), paroxetine (PAXIL™) and amitryptyline, for the treatment of depression, mood disorders or schizophrenia.

Additional features and advantages of the invention will become apparent from the detailed description and examples below, and the appended claims.

DETAILED DESCRIPTION OF THE INVENTION

The present invention provides non-imidazole aryloxyalkylamines useful for the treatment of disorders and conditions modulated by a histamine receptor.

A. TERMS

Certain Terms are Defined Below and by Their Usage Throughout This Disclosure.

As used herein, "halogen" shall mean chlorine, bromine, fluorine and iodine, or monovalent radicals thereof.

As used herein, the term "alkyl", whether used alone or as part of a substituent group, shall include straight and branched carbon chains. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. "Alkylene" refers to a bivalent hydrocarbyl group, such as methylene ($CH_2$), ethylene (—$CH_2$—$CH_2$—) or propylene (—$CH_2CH_2CH_2$—).

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "cycloalkyl" shall denote a three- to eight-membered, saturated monocyclic carbocyclic ring structure. Suitable examples include cyclopropyl, cyclobutyl, cyclopentyl, cyclohexyl, cycloheptyl and cyclooctyl.

As used herein, unless otherwise noted, "cycloalkenyl" shall denote a three- to eight-membered, partially unsaturated, monocyclic, carbocyclic ring structure, wherein the ring structure contains at least one double bond. Suitable examples include cyclohexenyl, cyclopentenyl, cycloheptenyl, cyclooctenyl, cyclohex-1,3-dienyl and the like.

As used herein, unless otherwise noted, "aryl" shall refer to carbocyclic aromatic groups such as phenyl, naphthyl, and the like. Divalent radicals include phenylene (—$C_6H_4$—) which is preferably phen-1,4-diyl, but may also be phen-1,3-diyl.

As used herein, unless otherwise noted, "aralkyl" shall mean any alkyl group substituted with an aryl group such as phenyl, naphthyl and the like. Examples of aralkyls include benzyl, phenethyl, and phenylpropyl.

As used herein, unless otherwise noted, the terms "heterocycle", "heterocyclyl" and "heterocyclo" shall denote any five-, six-, or seven-membered monocyclic, nine or ten membered bicyclic or thirteen or fourteen membered tricyclic ring structure containing at least one heteroatom moiety selected from the group consisting of N, O, SO, $SO_2$, (C=O), and S, and preferably N, O, or S, optionally containing one to four additional heteroatoms in each ring. In some embodiments, the heterocyclyl contains between 1 and 3 or between 1 and 2 additional heteroatoms. Unless otherwise specified, a heterocyclyl may be saturated, partially unsaturated, aromatic or partially aromatic. The heterocyclyl group may be attached at any heteroatom or carbon atom which results in the creation of a stable structure.

Exemplary monocyclic heterocyclic groups can include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, hexahydroazepinyl, 4-piperidinyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl, triazolyl, tetrazolyl, azetidinyl and the like.

For example, where Q is a non-aromatic nitrogen-containing heterocyclyl, preferred values for Q include piperidyl, piperazinyl, pyrrolinyl, pyrrolidinyl, morpholinyl, and N—(C1-6 alkyl)piperazinyl. These may be linked to the rest of the molecule by a nitrogen or a carbon atom; in general, N-linked heterocyclyls are preferred. Q can be substituted with between 1 and 3 substituents selected from pyridyl, pyrimidyl, furyl, thiofuryl, imidazolyl, (imidazolyl)$C_{1-6}$alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, and pyrrolyl. Examples of substituted Q, wherein the substituent comprises a heterocyclyl, include: 4-(4-chloropyridin-2-yl)amino-piperidin-1-yl; 4-(4-chloropyrimidin-2-yl)amino-piperidin-1-yl; 2-([1,2,4]triazol-1-yl)methyl-morpholin-1-yl; 3-(pyrazin-2-yl)piperidin-1-yl; 4-(pyrazol-1-yl)piperidin-1-yl; 4-(pyrimidin-2-yl)piperazin-1-yl; 4-(furan-2-yl)methylpiperazin-1-yl; 4-(thiophen-2-yl)methylpiperazin-1-yl; 4-(4-chloropyridin-2-yl)-[1,4]diazepan-1-yl; and 5-(isoxazol-5-yl)-2,5-diaza-bicyclo[2.2.1]heptan-2-yl.

Exemplary bicyclic heterocyclic groups include benzthiazolyl, benzoxazolyl, benzoxazinyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopridyl, furopyridinyl (such as furo[2,3-c]pyridinyl, furo[3,1-b]pyridinyl), or furo[2,3-b]pyridinyl), dihydroisoindolyl, dihydroquinazolinyl (such as 3,4-dihydro-4-oxo-quinazolinyl), tetrahydroquinolinyl (such as 1,2,3,4-tetrahydroquinolinyl), tetrahydroisoquinolinyl (such as 1,2,3,4-tetrahydroisoquiunolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isoindolyl, tetrahydroindoazolyl (such as 4,5,6,7-tetrahydroindazolyl), isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl,

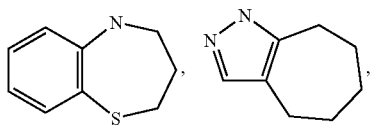

and the like.

Exemplary tricyclic heterocylclic groups include acridinyl, phenoxazinyl, phenazinyl, phenothiazinyl, carbozolyl, perminidinyl, phenanthrolinyl, carbolinyl, naphthothienyl, thianthrenyl, and the like.

Preferred heterocyclyl groups include morpholinyl, piperidinyl, piperazinyl, pyrrolidinyl, pyrimidinyl, pyridyl, pyrrolyl, imidazolyl, oxazolyl, isoxazolyl, acridinyl, azepinyl, hexahydroazepinyl, azetidinyl, indolyl, isoindolyl, thiazolyl, thiadiazolyl, quinolinyl, isoquinolinyl, 1,2,3,4-tetrahydroquinolinyl, 1,3,4-trihydroisoquinolinyl, 4,5,6,7-tetrahydroindadolyl, benzoxazinyl, benzoaxzolyl, benzthiazolyl, benzimidazolyl, tetrazolyl, oxadiazolyl,

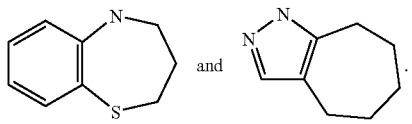

As used herein, unless otherwise noted, the term "heterocyclyl-alkyl" or "heterocyclyl-alkylene" shall denote any alkyl group substituted with a heterocyclyl group, wherein the heterocycly-alkyl group is bound through the alkyl portion to the central part of the molecule. Suitable examples of heterocyclyl-alkyl groups include, but are not limited to piperidinylmethyl, pyrrolidinylmethyl, piperidinylethyl, piperazinylmethyl, pyrrolylbutyl, piperidinylisobutyl, pyridylmethyl, pyrimidylethyl, and the like.

When a particular group is "substituted" (e.g., alkyl, alkylene, cycloalkyl, aryl, heterocyclyl, heteroaryl), that group may have one or more substituents, preferably from one to five substituents, more preferably from one to three substituents, most preferably from one to two substituents, independently selected from the list of substituents.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl(alkyl)amido(alkyl)" substituent refers to a group of the formula

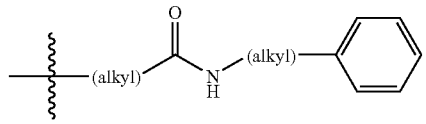

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes prevention, inhibition of onset, or alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Abbreviations used in the specification, particularly in the Schemes and Examples, are as follows:

| | |
|---|---|
| DBAD = | di-tert-butyl azodicarboxylate |
| DCE = | 1,2-dichloroethane |
| DCM = | dichloromethane |
| DEAD = | diethyl azodicarboxylate |
| DMA = | N,N-dimethylacetamide |
| DMAP = | 4-N,N-dimethylamino-pyridine |
| DME = | 1,2-dimethoxyethane |
| DMF = | dimethylformamide |
| DMSO = | dimethylsulfoxide |
| RT = | room temperature |
| TEA = | triethylamine |
| TFA = | trifluoroacetic acid |
| THF = | tetrahydrofuran |

The next section describes the compounds provided by the invention in more detail.

B. COMPOUNDS

The invention features compounds of formula (I) as described, for example, in the above Summary section and in the claims. Preferred compounds include those wherein:
(a) $NR_aR_b$ taken together form piperidyl, methylpiperidyl, dimethylamino, pyrrolidinyl, diethylamino, methylethylamino, ethylpropylamino, or dipropylamino;
(b) $NR_aR_b$ taken together form piperidyl, pyrrolidinyl, or diethylamino;
(c) $NR_aR_b$ taken together form piperidyl or pyrrolidinyl;
(d) one of $R_2$ and $R_3$ is G;
(e) $R_2$ is G;
(f) $R_3$ is G;
(g) n is between 1 and 4, inclusive;
(h) n is 1;
(i) $L_1$ is $C_{2-3}$ alkylene;
(j) $L_2$ is $C_{1-6}$ alkylene, $(C_{1-5}$ heteroaryl$)C_{1-6}$ alkylene, or -phenyl-$C_{1-6}$ alkyl
(k) $L_2$ is methylene;
(l) $L_3$ is ethylene, vinylene, ethynylene, and phenylene;
(m) Q is a non-aromatic nitrogen-containing $C_{2-5}$ heterocyclyl;
(n) Q is selected from piperidyl, N—($C_{1-6}$ alkyl)piperazinyl, piperazinyl, pyrrolinyl, pyrrolidinyl, and morpholinyl;
(o) Q is N-morpholinyl or N-piperidinyl, optionally substituted with between 1 and 3 substituents selected from hydroxyl, carboxamide, $C_{1-6}$ alkyl, $C_{1-8}$ heterocyclyl, $N(C_{1-6}$ alkyl$)(C_{1-8}$ heterocyclyl), $NH(C_{1-8}$ heterocyclyl), $(C_{1-8}$ heterocyclyl$)C_{1-3}$ alkylene, $C_{1-8}$ heterocyclyl-O—, $C_{1-6}$ alkoxy, $(C_{3-6}$ cycloalkyl)-O—, phenyl, (phenyl)$C_{1-3}$ alkylene, $N(C_{1-6}$ alkyl)[(phenyl)$C_{1-3}$ alkylene, and (phenyl)$C_{1-3}$ alkylene-O— where each of above heterocyclyl, phenyl, and alkyl groups may be optionally substituted with from 1 to 3 substituents independently selected from halogen, nitro, cyano, and $C_{1-3}$ alkyl;
(p) Q is substituted with a substituent comprising a $C_{1-6}$ heterocyclyl group selected from: pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, and pyrrolyl;
(q) Q is a substituted or unsubstituted N-morpholinyl;
(r) Q is $NR_8R_9$ wherein each of $R_8$ or $R_9$ is independently selected from hydrogen, $C_{1-8}$ alkyl, $C_{3-8}$ alkenyl, $C_{3-7}$ cycloalkyl, $(C_{3-7}$ cycloalkyl$)C_{1-6}$ alkylene, $C_{2-5}$ heterocyclyl, phenyl, $(C_{2-5}$ heterocyclyl$)C_{1-6}$ alkylene, and (phenyl)$C_{1-6}$ alkylene;
(s) one of $R_8$ and $R_9$ is hydrogen;
(t) $R_8$ is H and $R_9$ is phenyl or aromatic $C_{1-8}$ heterocyclyl optionally substituted with 1-3 substituents selected from halo, nitro, cyano, and $C_{1-3}$ alkyl;
(u) $R_9$ is phenyl, pyridyl, pyrimidyl, furyl, thiofuryl, imidazolyl, (imidazolyl)$C_{1-6}$ alkylene, oxazolyl, thiazolyl, 2,3-dihydro-indolyl, benzimidazolyl, 2-oxobenzimidazolyl, (tetrazolyl)$C_{1-6}$ alkylene, tetrazolyl, (triazolyl)$C_{1-6}$ alkylene, triazolyl, (pyrrolyl)$C_{1-6}$ alkylene, and pyrrolyl;
(v) $NR_aR_b$ taken together form piperidyl, methylpiperidyl, dimethylamino, pyrrolidinyl, diethylamino, methylethylamino, ethylpropylamino, or dipropylamino;
(w) $NR_aR_b$ taken together form piperidyl, pyrrolidinyl, or diethylamino;
(x) n is 1;
(y) G is selected from:
  (1) formula (i) wherein $L_4$ and $L_5$ are independently selected from $C_{2-3}$ alkylene,
  (2) formula (iii) wherein $L_6$ is $C_{2-3}$ alkylene and $L_7$ is $C_{2-3}$ alkylene or absent,
  (3) $L_2Q$ wherein $L_2$ is $C_{1-6}$ alkylene, phenyl $C_{1-4}$ alkylene, or (aromatic $C_{1-5}$ heterocyclyl)$C_{1-4}$ alkylene, and
  (4) $OL_1Q$ wherein $L_1$ is $C_{2-3}$ alkylene;
(z') G is selected from:
  (1) formula (i) wherein $L_4$ and $L_5$ are each $C_2$ alkylene,
  (2) formula (iii) wherein each of $L_6$ and $L_7$ is $C_2$ alkylene, and
  (3) $L_2Q$ wherein $L_2$ is methylene;
(z) G is $L_2Q$;
(aa) $R_{10}$ is H, branched $C_{3-6}$ alkyl, or benzyl;
(bb) $R_{10}$ is isopropyl or benzyl;
(cc) Q is a non-aromatic $C_{2-5}$ heterocyclyl;
(dd) Q is selected from piperidyl, N—($C_{1-6}$ alkyl)piperazinyl, piperazinyl, pyrrolinyl, pyrrolidinyl, and morpholinyl;
(ee) Q is a non-aromatic $C_{2-5}$ heterocyclyl;
(ff) Q is selected from piperidyl, N—($C_{1-6}$ alkyl)piperazinyl, piperazinyl, pyrrolinyl, pyrrolidinyl, and morpholinyl;
(gg) Q is selected from piperidyl, N—($C_{1-6}$ alkyl)piperazinyl, piperazinyl, pyrrolinyl, pyrrolidinyl, and morpholinyl;
(hh) $NR_aR_b$ taken together form piperidyl, pyrrolidinyl, or diethylamino;
(ii) n is 1;
(jj) $R_7$ is hydroxyl, halo, or absent where one of $L_6$ and $L_7$ provides a double bond to the carbon atom to which $R_6$ and $R_7$ are attached; or
(kk) Combinations of the above.

Examples of preferred compounds include: Methyl-[4-(3-piperidin-1-yl-propoxy)-benzyl]-(2-pyridin-2-yl-ethyl)-amine, Benzyl-methyl-[4-(3-piperidin-1-yl-propoxy)-benzyl]-amine, Methyl-(1-methyl-piperidin-4-yl)-[4-(3-piperidin-1-yl-propoxy)-benzyl]-amine, Ethyl-[4-(3-piperidin-1-yl-propoxy)-benzyl]-pyridin-4-ylmethyl-amine, [2-(3,4-Dimethoxy-phenyl)-ethyl]-methyl-[4-(3-piperidin-1-yl-propoxy)-benzyl]-amine, Methyl-phenethyl-[4-(3-piperidin-1-yl-propoxy)-benzyl]-amine, Dimethyl-[4-(3-piperidin-1-yl-propoxy)-benzyl]-amine, Dimethyl-{2-[4-(3-piperidin-1-yl-propoxy)-phenoxy]-ethyl}-amine, Methyl-phenethyl-[3-(3-piperidin-1-yl-propoxy)-benzyl]-amine, and Dibenzyl-(3-{2-[4-(3-piperidin-1-yl-propoxy)-phenyl]-pyrrol-1-yl}-propyl)-amine.

Additional preferred compounds include: Indan-1-yl-[4-(3-piperidin-1-yl-propoxy)-benzyl]-amine, Cyclohexyl-[4-(3-piperidin-1-yl-propoxy)-benzyl]-amine, Cyclopropyl-[4-(3-piperidin-1-yl-propoxy)-benzyl]-amine, Pyridin-2-yl-[4-(3-pyrrolidin-1-yl-propoxy)-benzyl]-amine, [4-(3-Piperidin-1-yl-propoxy)-benzyl]-pyridin-2-yl-amine, Phenyl-[4-(3-piperidin-1-yl-propoxy)-benzyl]-amine, [3-(3-Piperidin-1-yl-propoxy)-benzyl]-pyridin-2-yl-amine, (4-Chloro-phenyl)-[4-(3-piperidin-1-yl-propoxy)-benzyl]-amine, and (4-Chloro-phenyl)-[4-(3-piperidin-1-yl-propoxy)-benzyl]-amine.

Additional examples of preferred compounds include: 4-[3-(3-Piperidin-1-ylmethyl-phenoxy)-propyl]-morpholine, 1-[3-(4-Piperidin-1-ylmethyl-phenoxy)-propyl]-piperidine, Benzyl-methyl-{1-[4-(3-piperidin-1-yl-propoxy)-benzyl]-piperidin-4-yl}-amine, 1-[3-(4-Piperidin-1-ylmethyl-phenoxy)-propyl]-decadeuterio-piperidine, 1-(3-{4-[5-(3-Piperidin-1-yl-propylsulfanyl)-tetrazol-1-yl]-phenoxy}-propyl)-piperidine, 1-[4-(3-Piperidin-1-yl-propoxy)-benzyl]-piperidin-4-ol, 4-[4-(3-Piperidin-1-yl-propoxy)-benzyl]-morpholine, 2-[4-(3-Piperidin-1-yl-propoxy)- benzyl]-1,2,3,4-tetrahydro-isoquinoline, {1-[4-(3-Piperidin-1-yl-propoxy)-benzyl]-piperidin-4-yl}-pyridin-2-yl-amine, 1-Benzyl-4-[4-(3-piperidin-1-yl-propoxy)-benzyl]-piperazine, Indan-1-yl-[4-(3-piperidin-1-yl-propoxy)-benzyl]-amine, Cyclohexyl-[4-(3-piperidin-1-yl-propoxy)-benzyl]-amine, Cyclopropyl-[4-(3-piperidin-1-yl-propoxy)-benzyl]-amine, 8-[4-(3-Piperidin-1-yl-propoxy)-benzyl]-1,4-dioxa-8-aza-spiro[4.5]decane, 1-[4-(3-Piperidin-1-yl-propoxy)-benzyl]-piperidine-4-carboxylic acid amide, Methyl-[4-(3-piperidin-1-yl-propoxy)-benzyl]-(2-pyridin-2-yl-ethyl)-amine, Benzyl-methyl-[4-(3-piperidin-1-yl-propoxy)-benzyl]-amine, 4-Phenyl-1-[4-(3-piperidin-1-yl-propoxy)-benzyl]-piperidin-4-ol, 1-Phenyl-4-[4-(3-piperidin-1-yl-propoxy)-benzyl]-piperazine, Methyl-phenethyl-{1-[4-(3-piperidin-1-yl-propoxy)-benzyl]-piperidin-4-yl}-amine, 2-Methyl-1-[3-(4-piperidin-1-ylmethyl-phenoxy)-propyl]-piperidine, Methyl-(1-methyl-piperidin-4-yl)-[4-(3-piperidin-1-yl-propoxy)-benzyl]-amine, {1-[4-(3-Piperidin-1-yl-propoxy)-benzyl]-piperidin-4-yl}-pyridin-2-yl-(2-pyrrolidin-1-yl-ethyl)-amine, 2-{1-[4-(3-Piperidin-1-yl-propoxy)-benzyl]-piperidin-4-yl}-ethanol, 1-[3-(4-Pyrrolidin-1-ylmethyl-phenoxy)-propyl]-piperidine, 1-{3-[4-(4-Benzylidene-piperidin-1-ylmethyl)-phenoxy]-propyl}-piperidine, Ethyl-[4-(3-piperidin-1-yl-propoxy)-benzyl]-pyridin-4-ylmethyl-amine, 1-{3-[4-(4-Benzyl-piperidin-1-ylmethyl)-phenoxy]-propyl}-piperidine, 2-(4-Chloro-phenyl)-5-[4-(3-piperidin-1-yl-propoxy)-benzyl]-2,5-diaza-bicyclo[2.2.1]heptane, 1-[3-(2'-Piperidin-1-ylmethyl-biphenyl-4-yloxy)-propyl]-piperidine, 1-{1-[4-(3-Piperidin-1-yl-propoxy)-benzyl]-piperidin-4-yl}-1,3-dihydro-benzoimidazol-2-one, 1-(3-{4-[1-(3-Piperidin-1-yl-propyl)-1H-pyrrol-2-yl]-phenoxy}-propyl)-piperidine.

The invention also features compounds such as: 1-(3-Phenyl-allyl)-4-[4-(3-piperidin-1-yl-propoxy)-benzyl]-piperazine, [2-(3,4-Dimethoxy-phenyl)-ethyl]-methyl-[4-(3-piperidin-1-yl-propoxy)-benzyl]-amine, Methyl-phenethyl-[4-(3-piperidin-1-yl-propoxy)-benzyl]-amine, 1-{3-[3-(4-Benzylidene-piperidin-1-ylmethyl)-phenoxy]-propyl}-piperidine, 4-(4-Chloro-phenyl)-1-[4-(3-piperidin-1-yl-propoxy)-benzyl]-piperidin-4-ol, 1-[4-(3-Piperidin-1-yl-propoxy)-benzyl]-4-(3-phenyl-propyl)-piperidine, Dimethyl-[4-(3-piperidin-1-yl-propoxy)-benzyl]-amine, 1-{1-[4-(3-Piperidin-1-yl-propoxy)-benzyl]-piperidin-4-yl}-1H-benzoimidazole, 1-[4-(3-Piperidin-1-yl-propoxy)-benzyl]-1,2,3,4,5,6-hexahydro-[2,3']bipyridinyl, 1-{1-[4-(3-Piperidin-1-yl-propoxy)-benzyl]-piperidin-4-yl}-2,3-dihydro-1H-indole, 1-Isopropyl-4-[4-(3-piperidin-1-yl-propoxy)-benzyl]-piperazine, 1-[4-(3-Piperidin-1-yl-propoxy)-benzyl]-azacyclotridecane, 1-Methyl-4-[4-(3-piperidin-1-yl-propoxy)-benzyl]-piperazine, 5-Bromo-1-{1-[4-(3-piperidin-1-yl-propoxy)-benzyl]-piperidin-4-yl}-2,3-dihydro-1H-indole, Methyl-phenethyl-[3-(3-piperidin-1-yl-propoxy)-benzyl]-amine, 2-[55 1-[3-(4-Piperidin-1-ylmethyl-phenoxy)-propyl]-piperidin-2-yl]-ethanol, 4-[3-(4-Piperidin-1-ylmethyl-phenoxy)-propyl]-morpholine, 2-[4-(2-Piperidin-1-yl-ethoxy)-benzyl]-1,2,3,4-tetrahydro-isoquinoline, Pyridin-2-yl-[4-(3-pyrrolidin-1-yl-propoxy)-benzyl]-amine, 1-[4-(3-Piperidin-1-yl-propoxy)-benzyl]-1,2,3,4-tetrahydro-quinoline, [4-(3-Piperidin-1-yl-propoxy)-benzyl]-pyridin-2-yl-amine, 1-[2-(4-Piperidin-1-ylmethyl-phenoxy)-ethyl]-piperidine, Dibenzyl-(3-{2-[4-(3-piperidin-1-yl-propoxy)-phenyl]-pyrrol-1-yl}-propyl)-amine, Dimethyl-[3-(4-piperidin-1-ylmethyl-phenoxy)-propyl]-amine, Phenyl-[4-(3-piperidin-1-yl-propoxy)-benzyl]-amine, [3-(4-Piperidin-1-yl-propoxy)-benzyl]-pyridin-2-yl-amine, 5-(3-Piperidin-1-yl-propoxy)-2-[4-(3-piperidin-1-yl-propoxy)-phenyl]-pyrimidine, (4-Chloro-phenyl)-[4-(3-piperidin-1-yl-propoxy)-benzyl]-amine, 1-Methyl-4-[3-(4-piperidin-1-ylmethyl-phenoxy)-propyl]-piperazine, 1-[4-(2-Piperidin-1-yl-ethoxy)-benzyl]-1,2,3,4-tetrahydro-quinoline, and (4-Chloro-phenyl)-[3-(3-piperidin-1-yl-propoxy)-benzyl]-amine.

Additional examples include: 4-[3-(3-Piperidin-1-ylmethyl-phenoxy)-propyl]-morpholine, 1-[3-(4-Piperidin-1-ylmethyl-phenoxy)-propyl]-piperidine, Benzyl-methyl-{1-[4-(3-piperidin-1-yl-propoxy)-benzyl]-piperidin-4-yl}-amine, 1-[3-(4-Piperidin-1-ylmethyl-phenoxy)-propyl]-decadeuterio-piperidine, 1-(3-{4-[5-(3-Piperidin-1-yl-propylsulfanyl)-tetrazol-1-yl]-phenoxy}-propyl)-piperidine, 1-[4-(3-Piperidin-1-yl-propoxy)-benzyl]-piperidin-4-ol, 4-[4-(3-Piperidin-1-yl-propoxy)-benzyl]-morpholine, 2-[4-(3-Piperidin-1-yl-propoxy)-benzyl]-1,2,3,4-tetrahydro-isoquinoline, {1-[4-(3-Piperidin-1-yl-propoxy)-benzyl]-piperidin-4-yl}-pyridin-2-yl-amine, 1-Benzyl-4-[4-(3-piperidin-1-yl-propoxy)-benzyl]-piperazine, Indan-1-yl-[4-(3-piperidin-1-yl-propoxy)-benzyl]-amine, Cyclohexyl-[4-(3-piperidin-1-yl-propoxy)-benzyl]-amine, Cyclopropyl-[4-(3-piperidin-1-yl-propoxy)-benzyl]-amine, 8-[4-(3-Piperidin-1-yl-propoxy)-benzyl]-1,4-dioxa-8-aza-spiro[4.5]decane, 1-[4-(3-Piperidin-1-yl-propoxy)-benzyl]-piperidine-4-carboxylic acid amide, Methyl-[4-(3-piperidin-1-yl-propoxy)-benzyl]-(2-pyridin-2-yl-ethyl)-amine, Benzyl-methyl-[4-(3-piperidin-1-yl-propoxy)-benzyl]-amine, 4-Phenyl-1-[4-(3-piperidin-1-yl-propoxy)-benzyl]-piperidin-4-ol, 1-Phenyl-4-[4-(3-piperidin-1-yl-propoxy)-benzyl]-piperazine, Methyl-phenethyl-{1-[4-(3-piperidin-1-yl-propoxy)-benzyl]-piperidin-4-yl}-amine, 2-Methyl-1-[3-(4-piperidin-1-ylmethyl-phenoxy)-propyl]-piperidine, Methyl-(1-methyl-piperidin-4-yl)-[4-(3-piperidin-1-yl-propoxy)-benzyl]-amine, {1-[4-(3-Piperidin-1-yl-propoxy)-benzyl]-piperidin-4-yl}-pyridin-2-yl-(2-pyrrolidin-1-yl-ethyl)-amine, 2-{1-[4-(3-Piperidin-1-yl-propoxy)-benzyl]-piperidin-4-yl}-ethanol, 1-[3-(4-Pyrrolidin-1-ylmethyl-phenoxy)-propyl]-piperidine, 1-{3-[4-(4-Benzylidene-piperidin-1-ylmethyl)-phenoxy]-propyl}-piperidine, and Ethyl-[4-(3-piperidin-1-yl-propoxy)-benzyl]-pyridin-4-ylmethyl-amine.

More preferred compounds of the invention include: 1-{3-[4-(4-Benzyl-piperidin-1-ylmethyl)-phenoxy]-propyl}-piperidine, 2-(4-Chloro-phenyl)-5-[4-(3-piperidin-1-yl-propoxy)-benzyl]-2,5-diaza-bicyclo[2.2.1]heptane, 1-[3-(2'-Piperidin-1-ylmethyl-biphenyl-4-yloxy)-propyl]-piperidine, 1-{1-[4-(3-Piperidin-1-yl-propoxy)-benzyl]-piperidin-4-yl}-1,3-dihydro-benzoimidazol-2-one, 1-(3-{4-[1-(3-Piperidin-1-yl-propyl)-1H-pyrrol-2-yl]-phenoxy}-propyl)-piperidine, 1-(3-Phenyl-allyl)-4-[4-(3-piperidin-1-yl-propoxy)-benzyl]-piperazine, [2-(3,4-Dimethoxy-phenyl)-ethyl]-methyl-[4-(3-piperidin-1-yl-propoxy)-benzyl]-amine, Methyl-phenethyl-[4-(3-piperidin-1-yl-propoxy)-benzyl]-amine, 1-{3-[3-(4-Benzylidene-piperidin-1-ylmethyl)-phenoxy]-propyl}-piperidine, 4-(4-Chloro-phenyl)-1-[4-(3-piperidin-1-yl-propoxy)-benzyl]-piperidin-4-ol, 1-[4-(3-Piperidin-1-yl-propoxy)-benzyl]-4-(3-phenyl-propyl)-piperidine, Dimethyl-[4-(3-piperidin-1-yl-propoxy)-benzyl]-amine, 1-{1-[4-(3-Piperidin-1-yl-propoxy)-benzyl]-piperidin-4-yl}-1H-benzoimidazole, 1-[4-(3-Piperidin-1-yl-propoxy)-benzyl]-1,2,3,4,5,6-hexahydro-[2,3']bipyridinyl, 1-{1-[4-(3-Piperidin-1-yl-propoxy)-benzyl]-piperidin-4-yl}-2,3-dihydro-1H-indole, 1-Isopropyl-4-[4-(3-piperidin-1-yl-propoxy)-benzyl]-piperazine, 1-[4-(3-Piperidin-1-yl-propoxy)-benzyl]-azacyclotridecane, 1-Methyl-4-[4-(3-piperidin-1-yl-propoxy)-benzyl]-piperazine, 5-Bromo-1-{1-[4-(3-piperidin-1-yl -propoxy)-benzyl]-piperidin-4-yl}-2,3-dihydro-1H-indole, Methyl-phenethyl-[3-(3-piperidin-1-yl-propoxy)-benzyl]-amine, 2-{1-[3-(4-Piperidin-1-ylmethylphenoxy)-propyl]-piperidin-2-yl}-ethanol, 4-[3-(4-Piperidin-1-ylmethyl-phenoxy)-propyl]-morpholine, 2-[4-(2-Piperidin-1-yl-ethoxy)-benzyl]-1,2,3,4-tetrahydro-isoquinoline, Pyridin-2-yl-[4-(3-pyrrolidin-1-yl-propoxy)-benzyl]-amine, 1-[4-(3-Piperidin-1-yl-propoxy)-benzyl]-1,2,3,4-tetrahydro-quinoline, [4-(3-Piperidin-1-yl-propoxy)-benzyl]-pyridin-2-yl-amine, 1-[2-(4-Piperidin-1-ylmethyl-phenoxy)-ethyl]-piperidine, Dibenzyl-(3-{2-[4-(3-piperidin-1-yl-propoxy)-phenyl]-pyrrol-1-yl}-propyl)-amine, Dimethyl-[3-(4-piperidin-1-ylmethyl-phenoxy)-propyl]-amine, Phenyl-[4-(3-piperidin-1-yl-propoxy)-benzyl]-amine, and [3-(3-Piperidin-1-yl-propoxy)-benzyl]-pyridin-2-yl-amine.

The invention also features compounds such as: 1-Isopropyl-4-[4-(3-piperidin-1-yl-propoxy)-phenyl]-piperazine, 1-[4-(3-Piperidin-1-yl-propoxy)-phenyl]-piperazine hydrochloride, 1-Benzyl-4-[4-(3-pyrrolidin-1-yl-propoxy)-phenyl]-piperazine, 1-[4-(3-Pyrrolidin-1-yl-propoxy)-phenyl]-piperazine hydrochloride, and 1-Benzyl-4-[4-(3-piperidin-1-yl-propoxy)-phenyl]-piperazine. More preferred compounds include: 1-[4-(3-Piperidin-1-yl-propoxy)-phenyl]-piperazine, 1-Isopropyl-4-[4-(3-piperidin-1-yl-propoxy)-phenyl]-piperazine, 1-Benzyl-4-[4-(3-pyrrolidin-1-yl-propoxy)-phenyl]-piperazine, and 1-[4-(3-Pyrrolidin-1-yl-propoxy)-phenyl]-piperazine.

Further examples include: (A) 1-{3-[2'-(1-Isopropyl-piperidin-4-yl)-biphenyl-4-yloxy]-propyl}-piperidine, 1-(3-{4-[2-(1-Methyl-pyrrolidin-2-yl)-ethyl]-phenoxy}-propyl)-piperidine, and 1-{3-[4-(1-Isopropyl-piperidin-4-ylmethyl)-phenoxy]-propyl}-piperidine; (B) 1-{3-[4-(1-Methyl-pyrrolidin-2-yl)-phenoxy]-propyl}-piperidine, 1-Benzyl-4-[4-(3-piperidin-1-yl-propoxy)-phenyl]-piperidin-4-ol, and 1-Isopropyl-4-[4-(3-piperidin-1-yl-propoxy)-phenyl]-piperidin-4-ol; (C) 1-{3-[4-(1-Methyl-pyrrolidin-2-yl)-phenoxy]-propyl}-piperidine, and 1-Benzyl-4-[4-(3-piperidin-1-yl-propoxy)-phenyl]-piperidin-4-ol; (D) {3-Furan-2-yl-3-[4-(3-piperidin-1-yl-propoxy)-phenyl]-propyl}-dimethyl-amine, 4-{3-[4-(3-Piperidin-1-yl-propoxy)-phenyl]-3-pyrimidin-2-yl-propyl}-morpholine, 4-{4,4,4-Trifluoro-3-[4-(3-piperidin-1-yl-propoxy)-phenyl]-butyl}-morpholine, and 4-{4,4,4-Trifluoro-3-[4-(3-piperidin-1-yl-propoxy)-phenyl]-butyl}-morpholine; and (E) (2-Morpholin-4-yl-ethyl)-[4-(3-piperidin-1-yl-propoxy)-phenyl]-pyridin-2-yl-amine, Isopropyl-(2-morpholin-4-yl-ethyl)-[4-(3-piperidin-1-yl-propoxy)-phenyl]-amine, and (2-Morpholin-4-yl-ethyl)-[4-(3-piperidin-1-yl-propoxy)-phenyl]-thiazol-2-ylmethyl-amine.

The invention also provides compounds that are useful as synthetic intermediates of the compounds of the invention. Such compounds, which themselves may or may not have pharmaceutical activity, include those provided in the schemes and synthetic examples.

The invention also contemplates compounds isotopically-labelled to be detectable by positron emission tomography (PET) or single-photon emission computed tomography (SPECT) useful for studying $H_3$-mediated disorders.

During any of the processes for preparation of the compounds of the present invention, it may be necessary and/or desirable to protect sensitive or reactive groups on any of the molecules concerned. In addition, compounds of the invention may be modified by using protecting groups; such compounds, precursors, or prodrugs are also within the scope of the invention. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',441-tris(benzoyloxyphenyl)methyl, 3-(Imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N', N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Protection for 1,2- and 1,3-diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide(isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

Amino Protecting Groups

Protection for the amino group includes carbamates, amides, and special—NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include:

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-4-methoxybenzyl, N-di(4-methoxyphenyl)methyl, N-5-dibenzosuberyl, N-triphenylmethyl, N-(4-methoxyphenyl)

diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or —S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl)imidazoles, N,N'-dimethylimidazolidines, 2,3-dihydro-1,3-benzothiazoles, diethylamine adducts, and methylaluminum bis (2,6-di-t-butyl-4-methylphenoxide)(MAD)complex.

Monoprotection of Dicarbonyl Compounds

Selective Protection of α- and β-Diketones

Examples of selective protection of α- and β-diketones include enamines, enol acetates, enol ethers, methyl, ethyl, i-butyl, piperidinyl, morpholinyl, 4-methyl-1,3-dioxolanyl, pyrrolidinyl, benzyl, S-butyl, and trimethylsilyl.

Cyclic Ketals, Monothio and Dithio Ketals

Examples of cyclic ketals, monothio and dithio ketals include bismethylenedioxy derivatives and tetramethylbismethylenedioxy derivatives.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and d i-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxalanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl.

The compounds of the invention can be prepared according to the methods described in the next section.

C. SYNTHESIS

The compounds of the invention can be prepared according to traditional synthetic organic methods and matrix or combinatorial chemistry methods, as shown in Schemes 1-10 below and in Examples 1-97. A person of ordinary skill will be aware of variations and adaptations of the schemes and examples provided to achieve the compounds of the invention.

One skilled in the art will recognize that synthesis of the compounds of the present invention may be effected by purchasing intermediate or protected intermediate compounds described in any of the Schemes disclosed herein. Throughout the schemes when the reacting functionality is located at $R_3$, one skilled in the art will recognize that the choice of $R_3$ is illustrative only and that the reacting functionality could also be located at $R_1$ and $R_2$ also.

One skilled in the art will further recognize that during any of the processes for preparation of the compounds of the present invention, it may be necessary and/or desirable to protect sensitive or reactive groups on any of the molecules concerned. This may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", John Wiley & Sons, 1991. The protecting groups may be removed at a convenient subsequent stage using methods known from the art.

Compounds of formula (I) may be prepared according to the process outlined in Scheme 1.

sodium hydroxide, TEA, potassium carbonate, and the like, in an organic solvent such as DCM, THF, DMF, and the like, to yield the corresponding compound of formula (I).

In an alternative embodiment a compound of formula (II) may be reacted with a compound of formula (VI) where $X_1$ is as defined, in the presence of a base such as sodium hydroxide, TEA, sodium hydride, potassium carbonate, and the like, in an organic solvent such as DCM, THF, DMF, DMA, and the like, to yield the corresponding compound of formula (I).

In a further alternative embodiment a compound of formula (II) is reacted with a compound formula (III), or a compound of formula (VI) in which $X_1$ is OH, under Mitsunobu conditions, (in the presence of triphenylphosphine or polymer supported triphenyl phosphine and DBAD or DEAD, in an organic solvent such as DCM, THF, and the like), to yield the corresponding compounds of formula (IV) or (I).

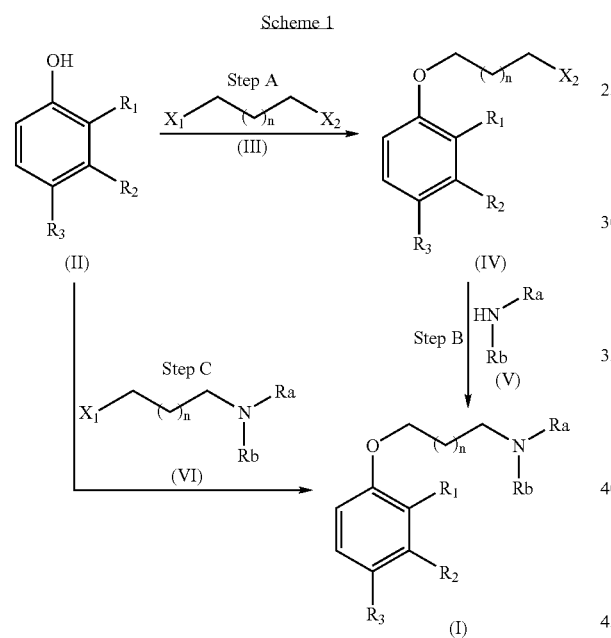

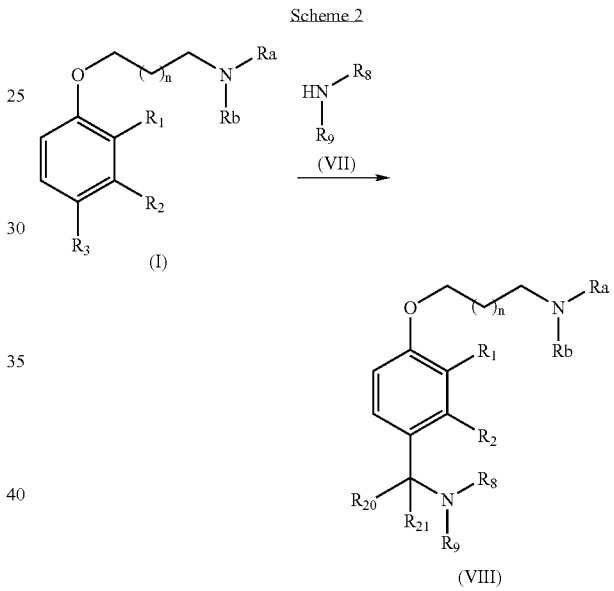

Generally, a compound of formula (II), a known compound or compound prepared by known methods is reacted in Step A to form the compound of formula (IV) and then reacted in Step B to form the compound of formula (I). Alternatively, the compound of formula (II) is reacted with a compound of formula (VI) in Step C to form the compound of formula (I). Specifically, a compound of formula (II), wherein $R_1$, $R_2$, $R_3$ are as defined is reacted with a compound of formula (III) where $X_1$ and $X_2$ are each independently selected from the group consisting Cl, Br, I, tosylate, mesylate, and the like wherein $X_1$ is selected such that under the reaction conditions, $X_1$ is preferentially displaced (rather than $X_2$; i.e. such that the compound of formula (III) is selectively coupled in terms of which end of the molecule is bonded to the compound of formula (II)), in the presence of a base such as sodium hydroxide, TEA, sodium hydride, potassium carbonate, and the like, in an organic solvent such as DCM, THF, DMF, DMA, and the like, to yield the corresponding compound of formula (IV). The compound of formula (IV) is reacted with a compound of formula (V), in the presence of a base such as A compound of formula (VIII) may be prepared according to the process outlined in Scheme 2. More particularly, a compound of formula (I), wherein $R_3$ is —$COR_5$ is reacted with an amine of formula (VII), in the presence of a reducing agent such as sodium borohydride, sodium cyanoborohydride, sodium triacetoxyborohydride, hydrogen gas in the presence of a catalyst, and the like, in a solvent such as methanol, ethanol, 1,2-dichloroethane, trifluoroethanol, and the like, to yield the compound of formula (VIII). One skilled in the art will recognize that addition of acid to decrease the pH of the reaction mixture to a pH of less than about 7 may be necessary to effect the reaction, wherein the acid is added as needed. Examples of appropriate acids include acetic acid, hydrochloric acid, and the like. When $R_{20}$ is H, the compound of formula (VII) is preferably reacted with a reducing agent such as sodium cyanoborohydride or sodium triacetoxyborohydride.

In an alternative embodiment, a compound of formula (VIII) may be prepared according to the processes outlined in Scheme 3.

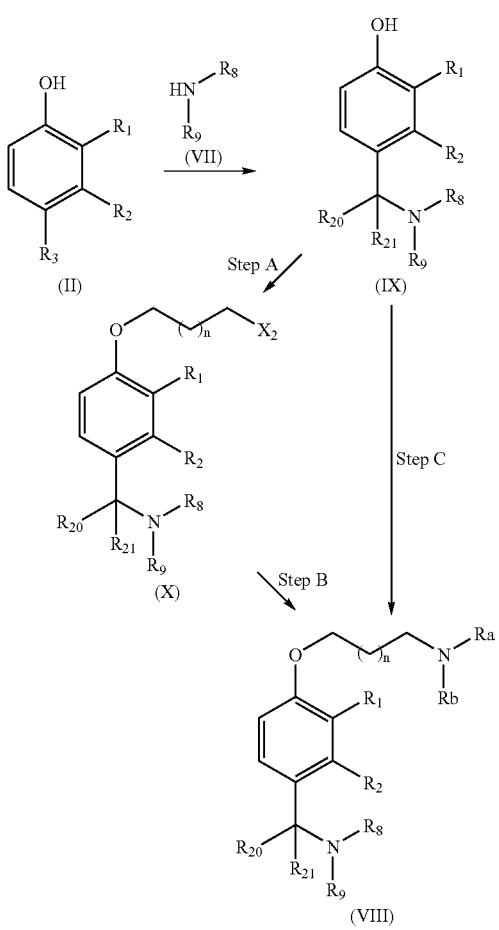

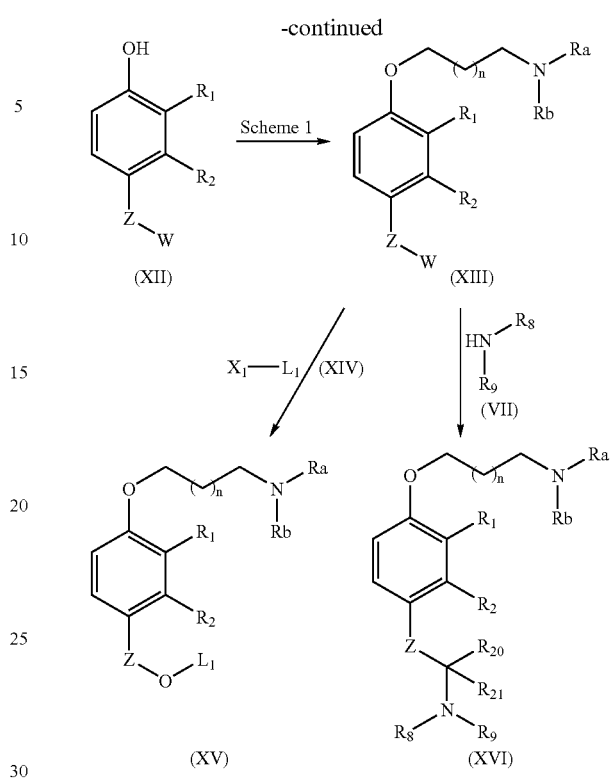

A compound of formula (II) wherein $R_3$ is —$COR_{20}$ is reacted with a compound of formula (VII) according to the procedures of Scheme 2 to afford a compound of formula (IX) which is further reacted according to the procedures of Scheme 1, either Steps A and B or Step C, to afford a compound of formula (VIII).

Scheme 4 provides guidance for the preparation of compounds of formula (XV) and (XVI) where Z can be substituted or unsubstituted phenyl or heterocycle and W is absent or —$COR_{20}$, or —OY, where Y is a protecting group. Preferred compounds are those in which Z is substituted phenyl, thienyl, pyridinyl, pyrimidinyl or pyrrolyl.

A compound of formula (II) or (I) is reacted with a compound of formula (XI) in the presence of a catalyst such as tetrakis(triphenylphosphine)palladium (0), and the like, in the presence of a base such as sodium carbonate, potassium carbonate, and the like, in an organic solvent such as toluene, benzene, xylene, and the like, to yield the corresponding compounds of formula (XII) and (XIII) respectively. A compound of formula (XIII) wherein W is —$COR_{20}$ is reacted with a compound of formula (VII) according to the procedures of Scheme 2 to afford a compound of formula (XVI). Alternatively a compound of formula (XV) may be prepared from a compound of formula (XIII) wherein W is —OY. The protecting group Y is first removed under the appropriate conditions to afford the corresponding hydroxyl compound which is reacted with a compound of formula (XIV), wherein $X_1$ is as defined, under the conditions described for Step A, Scheme 1, to afford a compound of formula (XV).

Scheme 4

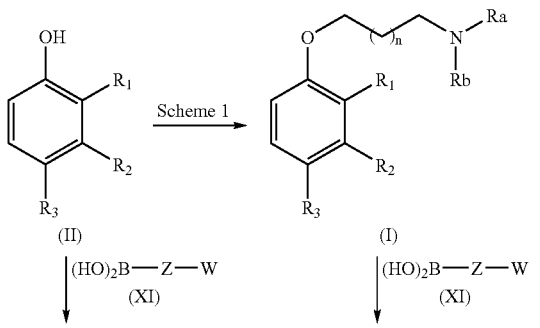

Scheme 5

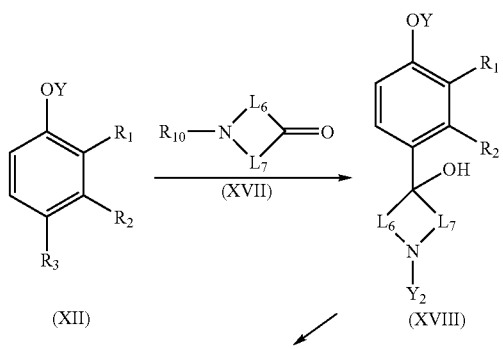

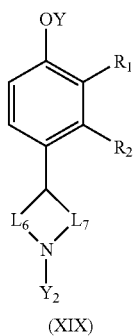

(XIX)

Scheme 1

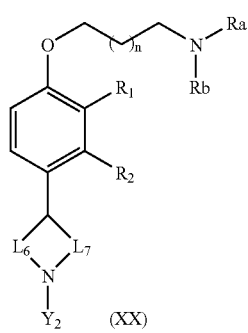

(XX)

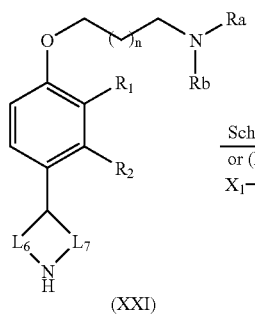

(XXI)

Scheme 2
or (XIVa)
$X_1$—$R_{10}$

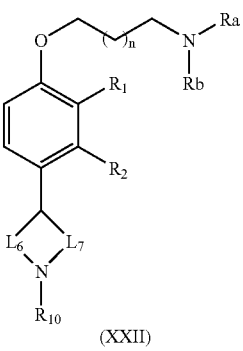

(XXII)

Compounds of formula (XXI) may be prepared according to the processes outlined in Scheme 5. A compound of formula (XII) where Y is a protecting group and $R_3$ is a halogen, preferably Br or I, more preferably I, is reacted with an organolithium reagent such as n-butyllithium in an organic solvent such as THF, diethyl ether and the like, and then reacted with a compound of formula (XVII) to afford a compound of formula (XVIII). The compound of formula (XVIII) is then reacted with a reducing agent such as sodium borohydride or sodium cyanoborohydride, and the like, in the presence of an acid such as TFA, HCl or acetic acid in an organic solvent such as THF or diethyl ether to yield the corresponding compound of formula (XIX). Alternatively the compound of formula (XVIII) may be reacted with hydrogen in the presence of a catalyst such as palladium on carbon or triethylsilane in the presence of TFA to yield a compound of formula (XIX). A compound of formula (XX) may be obtained upon removal of the protecting group Y from the compound of formula (XIX) followed by reaction under the conditions described in Scheme 1. A compound of formula (XXI) may be obtained from a compound of formula (XX) via removal of the group $Y_2$. One skilled in the art will recognize that in this Scheme both Y and $Y_2$ may be protecting groups. One skilled in the art will further recognize and understand the concept of orthogonal protection such that the groups Y and $Y_2$ may be removed separately and at the appropriate points in the synthetic procedure. The compound of formula (XXI) may also be reacted further via the procedures of Scheme 2 (reductive amination) or via N-alkylation with a compound of formula (XIVa) to afford a compound of formula (XXII).

Compounds of formula (XXVII) may be prepared according to the processes outlined in Scheme 6. Thus a compound of formula (XII) where $R_3$ is selected from Br and I, and is preferably I, is reacted with a compound of formula (XXIII) in the presence of a catalyst such as tris(dibenzylidineacetone)dipalladium(0), and the like, in the presence of a base such as sodium t-butoxide, cesium carbonate, triethylamine, potassium carbonate, and the like, in an organic solvent such as THF or dioxane, and the like, preferably in the presence of BINAP (2,2'-bis(diphenylphosphino)-1,1'-dinaphthyl) and 18-Crown-6 (a crown ether), to yield the corresponding compound of formula (XXIV).

Scheme 6

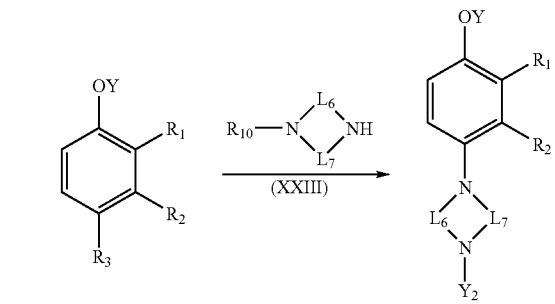

Scheme 1

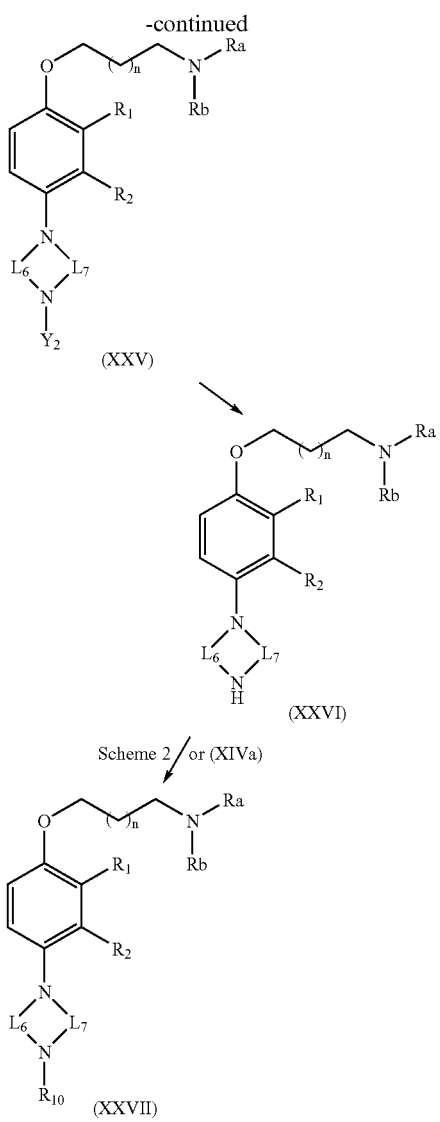

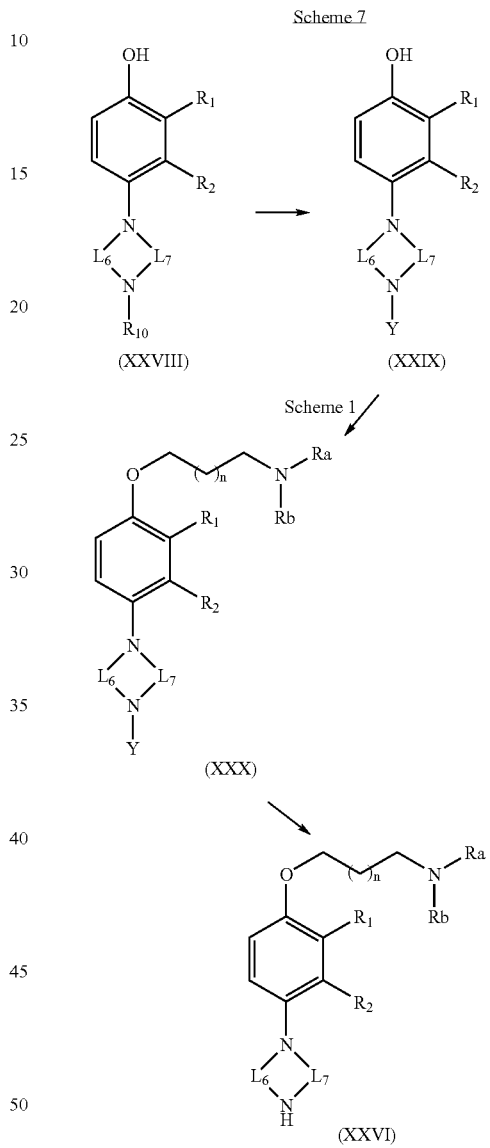

A compound of formula (XXV) may be obtained upon removal of the protecting group Y from the compound of formula (XXIV) followed by reaction under the conditions described in Scheme 1. A compound of formula (XXVI) may be obtained from a compound of formula (XXV) via removal of the group $Y_2$. The compound of formula (XXVI) may also be reacted further via the procedures of Scheme 2 (reductive amination) or via N-alkylation with a compound of formula (XIVa) to afford a compound of formula (XXVII).

In an alternative embodiment a compound of formula (XXVI) may be obtained from a compound of formula (XXVIII) according to the processes outlined in Scheme 7. A compound of formula (XXVIII) where $R_{10}$ is H is reacted with an alkyl chloroformate or dialkyldicarbonate and the like if necessary in the presence of an amine base to yield the corresponding compound of formula (XXIX) where Y represents a carbamate protecting group. In a preferred embodiment the chloroformate is ethylchloroformate, benzylchloroformate, 2,2,2-trichloroethylchloroformate, alpha-chloroethylchloroformate and the dialkyldicarbonate is di-tert-butyldicarbonate. A particularly preferred embodiment uses di-tert-butyldicarbonate. The compound of formula (XXIX) is reacted according to the procedures of Scheme 1 to afford compound (XXX) whereupon removal of the carbamate protecting group affords compound of formula (XXVI). In a preferred embodiment a tert-butyl carbamate is removed under acidic conditions using TFA or HCl in a solvent, for example TFA in DCM or HCl in ether.

Compounds of formula (XXXV) may be prepared according to the procedures outlined in Scheme 8. Compounds of formula (XXXI) are reacted according to the processes outlined in Scheme 1 to give compounds of formula (XXXII). Removal of the protecting group Y affords compound of formula (XXXIII). In a preferred embodiment the group Y is a benzyl group, thus the compound of formula (XXXII) is reacted with with hydrogen gas or ammonium formate, in the presence of a catalyst such as palladium on carbon, and the like, in a solvent such as methanol, ethanol, and the like, (i.e. catalytic hydrogenolysis) to yield the corresponding compound of formula (XXXIII). The compound of formula (XXXIII) is reacted with a compound of formula (XXXIV) to afford a compound of formula (XXXV). Thus the compound of formula (XXXIII) is reacted with a compound of formula (XXXIV) under Mitsunobu conditions, (in the presence of triphenylphosphine or polymer supported triphenyl phosphine and DBAD or DEAD, in an organic solvent such as DCM, THF, and the like), to yield the corresponding compound of formula (XXXV).

compound of formula (XXXIV) under Mitsunobu conditions, (in the presence of triphenylphosphine or polymer supported triphenyl phosphine and DBAD or DEAD, in an organic solvent such as DCM, THF, and the like), to yield the corresponding compound of formula (XXXVI).

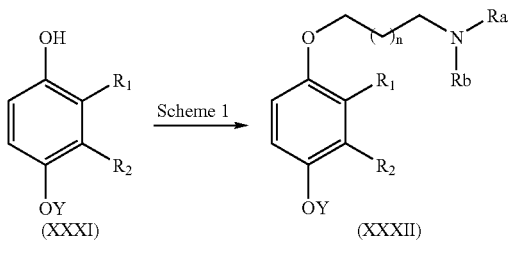

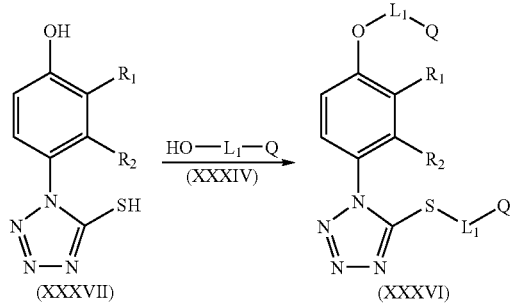

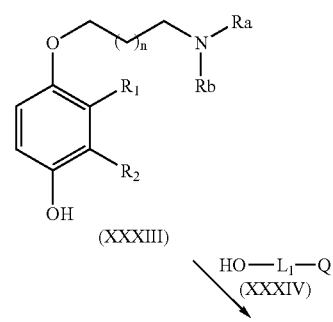

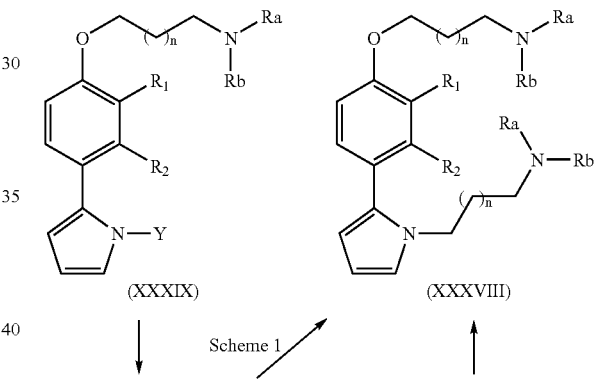

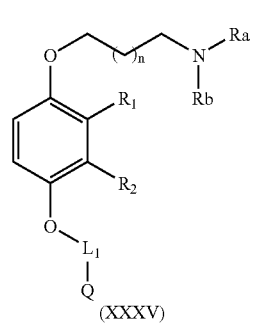

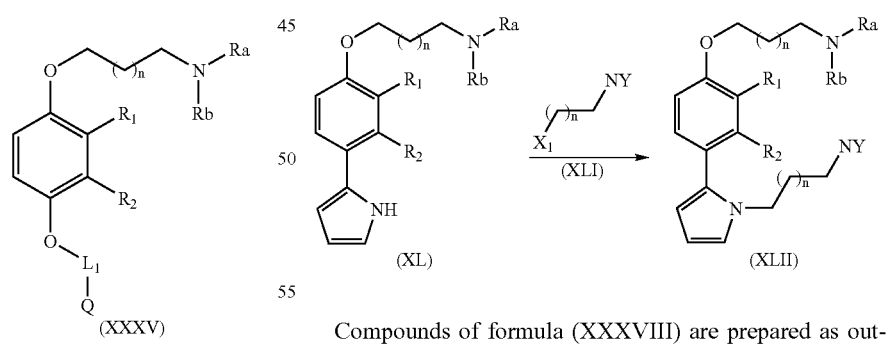

In a particular embodiment of Scheme 8, illustrated in Scheme 9, the compound of formula (XXXVI) may be prepared via a double Mitsunobu reaction between a compound of formula (XXXVII) and a compound of formula (XXXIV). Thus the compound of formula (XXXVII) is reacted with a Compounds of formula (XXXVIII) are prepared as outlined in Scheme 10, by reacting compounds of formula (XL), prepared as outlined in Scheme 4, with a compound of formula (XLI) to afford a compound of formula (XLII). The compound of formula (XLII) may be reacted further to give a compound of formula (XXXVIII). In a particular embodiment compound of formula (XXXIX) contains the protecting group Y which is removed to afford a compound of formula (XL). The compound of formula (XL) is reacted with a compound of formula (XLI) in the presence of a base to yield a compound of formula (XLII). In a preferred embodiment the compound of formula (XLI) contains NY where NY is 2,2,5,5-tetramethyl-1-aza-2,5-disilacyclopentane. The protecting group Y of the compound of formula (XXXXII) is removed and the primary amine product reacted via alkylation or reductive amination to afford compound of formula (XXXVIII). In an alternative embodiment a compound of formula (XXXVIII) may be prepared from a compound of formula (XL) according to the procedures outlined in Scheme 1.

D. FORMULATION, ADMINISTRATION, AND THERAPY

The disclosed compounds, alone or in combination (with, for example, a histamine $H_1$ receptor antagonist), are useful for treating or preventing neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof.

1. Formulation and Administration

The compounds or compositions of the invention may be formulated and administered to a subject by any conventional route of administration, including, but not limited to, intravenous, oral, subcutaneous, intramuscular, intradermal and parenteral administration. The quantity of the compound which is effective for treating each condition may vary, and can be determined by one of ordinary skill in the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali ml salts, e.g., sodium or potassium salts; alkaline earth ml salts, e.g., calcium or magnesium salts; and salts formed with suitable organic ligands, e.g., quaternary ammonium salts.

Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preption of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention also provides pharmaceutical compositions comprising one or more compounds of this invention in association with a pharmaceutically acceptable carrier and optionally additional pharmaceutical agents such as $H_1$ antagonists or SSRIs. Preferably these compositions are in unit dosage forms such as pills, tablets, caplets, capsules (each including immediate release, timed release and sustained release formulations), powders, granules, sterile parenteral solutions or suspensions (including syrups and emulsions), metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 5 to about 1000 mg of the active ingredient of the present invention. Examples include 5 mg, 7 mg, 10 mg, 15 mg, 20 mg, 35 mg, 50 mg, 75 mg, 100 mg, 120 mg, 150 mg, and so on. The tablets or pills of the disclosed compositions can be coated or otherwise compounded to provide a dosage form affording the advantage of prolonged action. For example, the tablet or pill can comprise an inner dosage and an outer dosage component, the latter being in the form of an envelope over the former. The two components can be septed by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the compounds and compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of ADHD is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the subject to be treated. An effective amount of the drug is ordinarily supplied at a dosage level of from about 0.01 mg/kg to about 20 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

2. Combination Therapy

The disclosed compounds are useful in combination with other therapeutic agents, including $H_1$ receptor antagonists, $H_2$ receptor antagonists, and neurotransmitter modulators such as SSRIs and non-selective serotonin re-uptake inhibitors (NSSRIs).

Methods are known in the art for determining effective doses for therapeutic and prophylactic purposes for the disclosed pharmaceutical compositions or the disclosed drug combinations, whether or not formulated in the same composition. For therapeutic purposes, the term "jointly effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "jointly effective amount" refers to that amount of each active compound or pharmaceutical agent, alone or in combination, that inhibits in a subject the onset or progression of a disorder as being sought by a researcher, veterinarian, medical doctor or other clinician, the delaying of which disorder is mediated, at least in part, by the modulation of one or more histamine receptors. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both drugs are administered in an amount that is sub-therapeutic or sub-prophylactic if administered alone, but are therapeutic or prophylactic when administered together. Combinations of three or more drugs are analogously possible. Methods of combination therapy include co-administration of a single formulation containing all active agents; essentially contemporaneous administration of more than one formulation; and administration of two or more active agents separately formulated.

E. EXAMPLES

Example 1

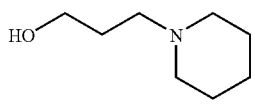

3-Piperidin-1-yl-propan-1-ol

A solution of potassium carbonate (24.9 g) and piperidine (130 mL) in 1:1 ethanol-water (130 mL) was treated with 3-bromopropan-1-ol (25.0 g). The resulting mixture was stirred vigorously for 20 h. Dichloromethane (200 mL) and water (50 mL) were added and the aqueous phase was extracted with dichloromethane (2×100 mL). The combined organic extracts were dried (magnesium sulfate) and evaporated in vacuo. Kugelrohr distillation of the residue (5-10 mm Hg, 120° C.) gave the title compound as a colorless oil (13.9 g).

Example 2

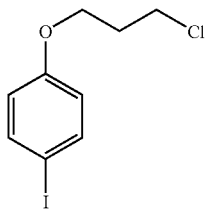

1-(3-Chloro-propoxy)-4-iodo-benzene

A suspension of 4-iodophenol (20 g), 1-bromo-3-chloropropane (18 mL), and potassium carbonate (38 g) in acetone (250 mL) was heated at reflux for 16 h and allowed to cool to room temperature. The suspension was filtered, and the filtrate was evaporated in vacuo. Kugelrohr distillation of the residue (5-10 mm Hg, 210° C.) gave the title compound as a white crystalline solid (22 g).

Example 3

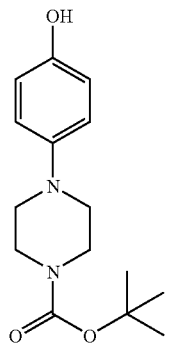

4-(4-Hydroxy-phenyl)-piperazine-1-carboxylic acid tert-butyl ester

To a solution of 1-(4-hydroxyphenyl)piperazine (12.0 g) in tetrahydrofuran (50 mL) was added dropwise a solution of di-tert butyl dicarbonate (72 ml of a 1M solution). Saturated aqueous sodium bicarbonate (60 ml) was added and the resulting mixture was stirred at room temperature for 16 h. The reaction was extracted with ethyl acetate (700 ml). The organic phase was washed with water (50 ml), brine (5 ml), and dried (magnesium sulfate). Solvent was removed in vacuo and the residue was triturated with hexanes, giving the title compound as a brown solid (16.3 g).

Example 4

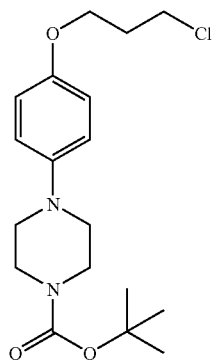

4-[4-(3-Chloro-propoxy)-phenyl]-piperazine-1-carboxylic acid tert-butyl ester

A suspension of tert-butyl 1-(4-(4-hydroxy)phenyl)piperazine carboxylate (5.0 g), 1-bromo-3-chloropropane (3.6 mL), and potassium carbonate (7.4 g) in acetone (60 mL) was heated at reflux for 24 h and allowed to cool to room temperature. The suspension was filtered, and the filtrate was evaporated in vacuo. Silica gel chromatography of the residue (30% ethyl acetate/hexane) gave the title compound as a light yellow solid (5.3 g).

Example 5

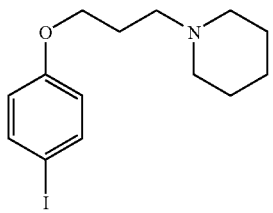

1-[3-(4-Iodo-phenoxy)-propyl]-piperidine

A suspension of 4-(3-chloro-1-propoxy)iodobenzene (5 g), piperidine (2.2 mL), sodium carbonate (2.7 g), and potassium iodide (140 mg) in n-butanol (30 mL) was heated in a 105° C. bath for 18 h. The resulting mixture was allowed to cool to room temperature, diluted with water (50 mL), and extracted with methylene chloride (2×20 mL). The combined organic phases were dried (magnesium sulfate), and evaporated in vacuo. Kugelrohr distillation of the residue (5 mm Hg, 260° C.) gave the title compound as a white crystalline solid (4.8 g).

Example 6

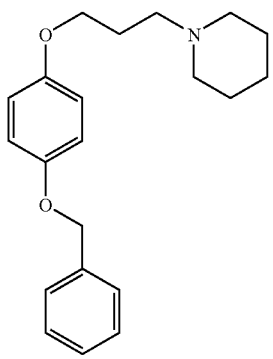

1-[3-(4-Benzyloxy-phenoxy)-propyl]-piperidine

A suspension of 4-benzyloxyphenol (30 g), 1-bromo-3-chloropropane (30 mL) and potassium carbonate (62 g) in acetone (400 mL) was heated at reflux for 25 h and allowed to cool to room temperature. The suspension was filtered, and the filtrate was evaporated in vacuo. Recrystallization of the residue (hexanes) gave fine needles (29 g). A suspension of this material (32 g), piperidine (14.8 mL), sodium carbonate (18.3 g), and potassium iodide (95 mg) in n-butanol (140 mL) was heated in a 105° C. bath for 28 h. The resulting mixture was allowed to cool to room temperature, diluted with water (100 mL), and extracted with methylene chloride (3×100 mL). The combined organic phases were dried (magnesium sulfate), and evaporated in vacuo. Recrystallization of the residue (ethanol) gave the title compound as a white crystalline solid (29 g).

Example 7

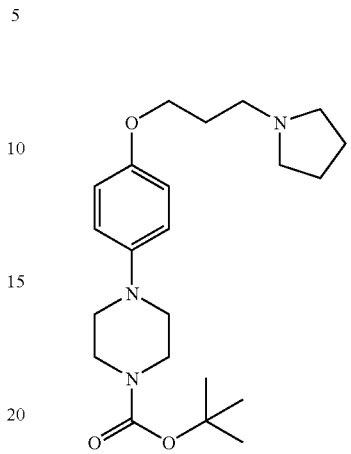

4-[4-(3-Pyrrolidin-1-yl-propoxy)-phenyl]-piperazine-1-carboxylic acid tert-butyl ester A suspension of the product of Example 4 (1.0 g), pyrrolidine (435 mg), sodium carbonate (297 mg), and potassium iodide (9.3 mg) in n-butanol (5 mL) was heated in a 100° C. bath for 16 h. The resulting mixture was allowed to cool to room temperature, and filtered through celite. The filtrate evaporated in vacuo. Silica gel chromatography of the residue (5% 2M ammonia-methanol/dichloromethane) gave the title compound as a yellow solid (900 mg).

Example 8

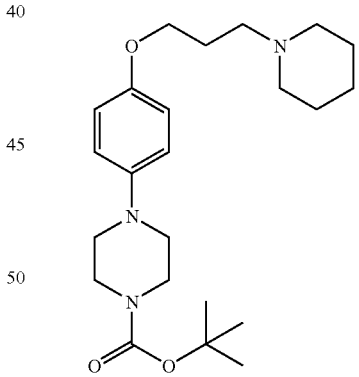

4-[4-(3-Piperidin-1-yl-propoxy)-phenyl]-piperazine-1-carboxylic acid tert-butyl ester A suspension of the product of Example 4 (3.0 g), piperidine (1.4 g), sodium carbonate (900 mg), and potassium iodide (28 mg) in n-butanol (15 mL) was heated in a 100° C. bath for 16 h. The resulting mixture was allowed to cool to room temperature, and filtered through celite. The filtrate evaporated in vacuo. Silica gel chromatography of the residue (5% 2M methanolic ammonia/dichloromethane) gave the title compound as a brown solid (2.3 g).

Example 9

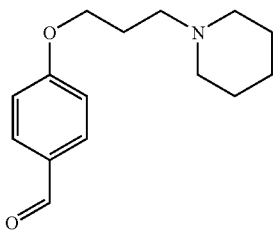

4-(3-Piperidin-1-yl-propoxy)-benzaldehyde

A solution the product of Example 11 (10 g), piperidine (6.5 mL), sodium carbonate (8.1 g), and potassium iodide (422 mg) in 1-butanol (60 mL) was heated to 105° C. for 18 h, cooled to RT, diluted with water (50 mL) and extracted with DCM (3×50 mL). The combined organic phases were dried (magnesium sulfate) and evaporated, giving the title compound as a yellow oil (11.5 g).

Example 10

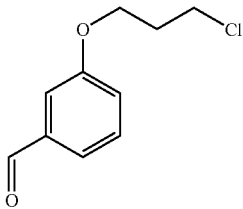

3-(3-Chloro-propoxy)-benzaldehyde

A suspension of 3-hydroxybenzaldenyde (25.0 g), 1-bromo-3-chloropropane (30.4 mL) and potassium carbonate (50.9 g) in acetone (300 mL) was heated under reflux. After 16 h, the resulting mixture was cooled to RT and filtered through a pad of celite. The pad was washed with acetone (3×20 mL). The combined filtrates were concentrated. Chromatography of the residue (15-25% ethyl acetate/hexane) gave the title compounds as a yellow oil (14.2 g).

Example 11

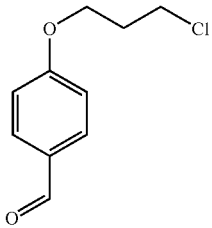

4-(3-Chloro-propoxy)-benzaldehyde

A suspension of 4-hydroxybenzaldehyde (40 g), 1-bromo-3-chloropropane (63 mL), and potassium carbonate (136 g) in acetone (920 mL) was heated to reflux for 16 h. The resulting mixture was filtered, and the filtrate was evaporated. Distillation of the residue (0.5 mm Hg, 220° C.) gave the title compound as a pale yellow oil that crystallized on standing (46 g).

Example 12

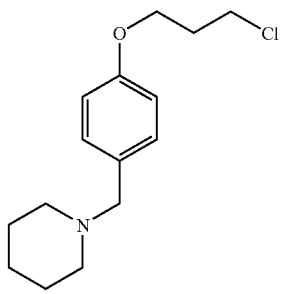

1-[4-(3-Chloro-propoxy)-benzyl]-piperidine

A solution of the product of Example 11 (5.0 g), piperidine (3.1 mL), and acetic acid (2.0 mL) in DCE (100 mL) was treated with sodium triacetoxyborohydride (9.3 g). After 16 h, the resulting mixture was diluted with water (100 mL) and extracted with DCM (3×50 mL). The combined organic phases were dried (magnesium sulfate) and evaporated, giving the title compound as an amber oil (5.3 g).

Example 13

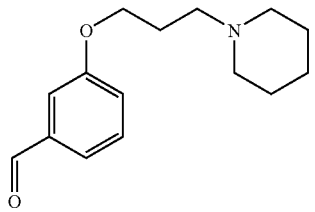

3-(3-Piperidin-1-yl-propoxy)-benzaldehyde

A suspension of the product of Example 10 (4.16 g), potassium carbonate (5.52 g) and piperidine (5.0 mL) in DMF (25.0 mL) was heated to 80° C. for 12 h. The resulting mixture was poured into water (400 mL) and extracted with ethyl acetate (3×50 mL) and the combined extracts were dried over sodium sulfate. Chromatography of the residue (1 to 10% 2M methanolic ammonia/DCM) gave the title compound as a yellow oil (3.14 g).

Example 14

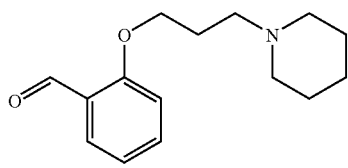

2-(3-Piperidin-1-yl-propoxy)-benzaldehyde

A suspension of 2-hydroxybenzaldenyde (5.43 g), 1-bromo-3-chloropropane (6.5 mL) and potassium carbonate (13.11 g) in acetone (100 mL) was heated under reflux. After 16 h, the resulting mixture was cooled to RT and poured into water (400 mL) and extracted with ether (3×100 mL). The organics were washed with water (3×50 mL) and 1M NaOH (2×50 mL) and brine. The combined filtrates were concentrated. The excess 1-bromo-3-chloropropane was removed by distillation (80° C., 2 mm Hg) to give 1-(3-chloro-propoxy)-benzaldehyde as a yellow oil (8.80 g). A suspension of this material (4.81 g), potassium carbonate (5.04 g) and piperidine (5.0 mL) in DMF (5.0 mL) was then heated to 80° C. for 12 h. The resulting mixture was poured into water (400 mL) and extracted with DCM (3×50 mL) and the combined extracts were dried over sodium sulfate. Chromatography of the residue (1-10% 2M methanolic ammonia/DCM) gave the title compound as a yellow oil (1.53 g).

Example 15

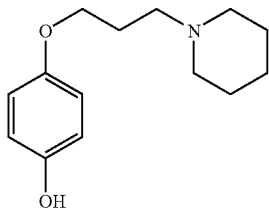

4-(3-Piperidin-1-yl-propoxy)-phenol

A suspension of the product of Example 6 (2.5 g), ammonium formate (2.7 g), and 10% palladium on carbon (2.5 g) in methanol (100 mL) was heated in a 68° C. bath for 3 h, and allowed to cool to room temperature. The mixture was filtered through Celite, and the filtrate was evaporated in vacuo. Saturated aqueous sodium bicarbonate was added, and the mixture was extracted with dichloromethane (4×30 mL). The combined organic phases were dried (magnesium sulfate) and evaporated in vacuo, yielding the title compound as a pink microcrystalline solid (1.3 g) which was used without further purification. A small sample (100 mg) was recrystallized (ethanol) to obtain the title compound as beige prisms (68 mg).

Example 16

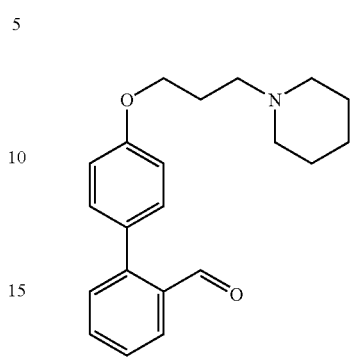

4'-(3-Piperidin-1-yl-propoxy)-biphenyl-2-carbaldehyde

A solution of the product of Example 5 (593 mg), tetrakis(triphenylphosphine)palladium(0) (116 mg), and 2-formylphenylboronic acid (270 mg) in tetrahydrofuran (11 mL) was treated with a solution of sodium carbonate (191 mg) in water (2.7 mL). The resulting mixture was heated in a 65° C. bath for 14 h, and allowed to cool to room temperature. Ether (20 mL) and water (10 mL) were added, and the aqueous phase was extracted with ether (2×20 mL). The combined organic phases were dried (magnesium sulfate) and evaporated in vacuo. Silica gel chromatography of the residue (2.5% 2M ammonia-methanol/dichloromethane) gave the title compound as a pale yellow oil (175 mg).

Example 17

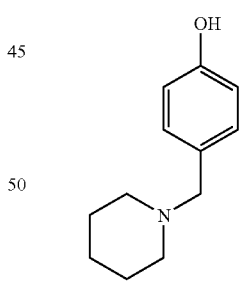

4-Piperidin-1-ylmethyl-phenol

A solution of 4-hydroxybenzaldehyde (10 g), piperidine (8.9 mL), and acetic acid (4.7 mL) in DCE (200 mL) was treated with sodium triacetoxyborohydride (24 g). After 16 h, the resulting mixture was treated with saturated aqueous sodium bicarbonate (100 mL) and extracted with DCM (5×100 mL). The combined organic phases were dried (magnesium sulfate) and evaporated. Trituration of the residue with ethyl acetate gave the title compound as a white crystalline solid (5.5 g).

Example 18

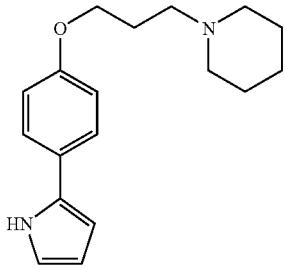

1-{3-[4-(1H-Pyrrol-2-yl)-phenoxy]-propyl}-piperidine

To a stirred solution of the product of Example 5 (4 g) in tetrahydrofuran (30 mL) was added tetrakis(triphenylphosphine)palladium (0.76 g). The mixture was stirred at RT for 30 min and then treated with a solution of 1-(tert-butoxycarbonyl)pyrrole-2-boronic acid (2.57 g) and sodium carbonate (1.29 g) in water (20 mL). The mixture was heated to reflux for 1.5 d. The tetrahydrofuran was removed under reduced pressure and the aqueous layer was extracted several times with methylene chloride. The combined organic layers were dried (sodium sulfate), filtered and concentrated under reduced pressure to give a black oil (5.42 g). Chromatography (50% ethyl acetate/hexane containing 2% triethylamine) afforded an orange-red oil (3.63 g). This material (3.63 g) was dissolved in a mixture of methanol (75 mL) and tetrahydrofuran (40 mL) and treated with sodium methoxide (3.12 g). The mixture was stirred at RT for 12 h and then additional sodium methoxide was added (1.7 g). After stirring at RT for 12 additional hours, the mixture was concentrated under reduced pressure, and the residue partitioned between diethyl ether and water. The organic layer was separated and the aqueous layer extracted several times with diethyl ether. The combined organic layers were dried (sodium sulfate), filtered and concentrated, yielding the title compound (2.68 g).

Example 19

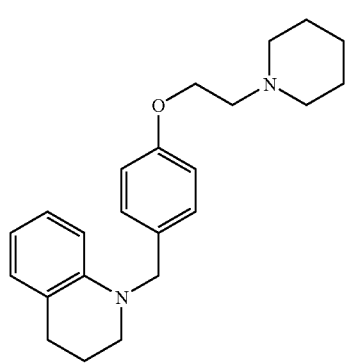

$K_i = 37$ nM

1-[4-(2-Piperidin-1-yl-ethoxy)-benzyl]-1,2,3,4-tetrahydro-quinoline

A solution of 4-(2-piperidylethoxy)-benzaldehyde (200 mg), 1,2,3,4-tetrahydroquinoline (126 mg), and acetic acid (0.11 mL) in dichloroethane (2 mL) was treated with sodium triacetoxyborohydride (254 mg). After 15 h, the reaction was quenched with saturated aqueous sodium bicarbonate, and the aqueous phase was extracted with dichloromethane (2×2 mL). The combined organic phases were dried (magnesium sulfate) and evaporated in vacuo. Silica gel chromatography of the residue (2% 2M ammonia-methanol/dichloromethane) gave the title compound as a colorless viscous oil (51 mg). $^1$H NMR (400 MHz, CDCl$_3$): 7.17 (d, J=8.8 Hz, 2H), 6.97 (d, J=7.4 Hz, 2H), 6.86 (d, J=8.8 Hz, 2H), 6.60-6.52 (m, 2H), 4.41 (s, 2H), 4.09 (t, J=6.2 Hz, 2H), 3.36-3.32 (m, 2H), 2.83-2.75 (m, 4H), 2.54-2.47 (m, 4H), 2.03-1.97 (m, 2H), 1.64-1.57 (m, 4H), 1.49-1.42 (m, 2H).

Example 20

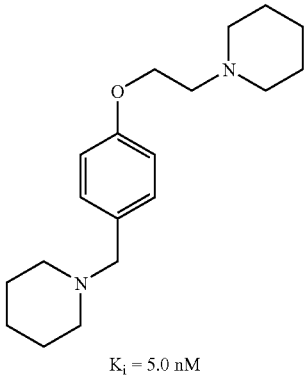

$K_i = 5.0$ nM

1-[2-(4-Piperidin-1-ylmethyl-phenoxy)-ethyl]-piperidine

A solution of 4-(2-piperidylethoxy)-benzaldehyde (200 mg), piperidine (80 mg), and acetic acid (1 mL of a solution prepared from acetic acid (0.5 mL) in dichloroethane (10 mL)) in dichloroethane (1 mL) was treated with sodium triacetoxyborohydride (254 mg). After 17 h, the reaction was quenched with saturated aqueous sodium bicarbonate, and the aqueous phase was extracted with dichloromethane (2×1 mL). The combined organic phases were dried (magnesium sulfate) and evaporated in vacuo. Silica gel chromatography of the residue (5% 2M ammonia-methanol/ethyl acetate) gave the title compound as a pale yellow oil (69 mg). $^1$H NMR (400 MHz, CDCl$_3$): 7.20 (d, J=8.4 Hz, 2H), 6.84 (d, J=8.4 Hz, 2H), 4.08 (t, J=6.1 Hz, 2H), 3.39 (s, 2H), 2.75 (t, J=6.1 Hz, 2H), 2.54-2.45 (m, 4H), 2.38-2.30 (m, 4H), 1.63-1.52 (m, 8H), 1.47-1.37 (m, 4H).

Example 21

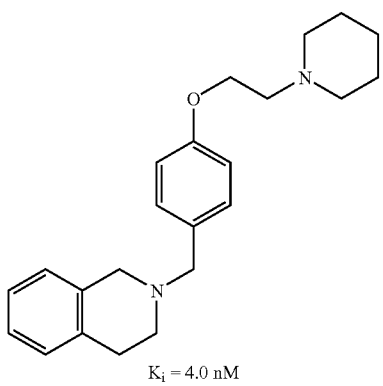

$K_i = 4.0$ nM

2-[4-(2-Piperidin-1-yl-ethoxy)-benzyl]-1,2,3,4-tetrahydro-isoquinoline 1,2,3,4-Tetrahydroisoquinoline (126 mg) was treated with a solution of acetic acid (1 mL of a solution of acetic acid (1 mL) in dichloroethane (10 mL)) and the resulting solution was added to 4-(2-piperidylethoxy)-benzaldehyde (200 mg). The resulting mixture was treated with sodium triacetoxyborohydride (254 mg). After 15 h, the reaction was quenched with saturated aqueous sodium bicarbonate, and the aqueous phase was extracted with dichloromethane (2×2 mL). The combined organic phases were dried (magnesium sulfate) and evaporated in vacuo. Silica gel chromatography of the residue (2% 2M ammonia-methanol/dichloromethane) gave the title compound as a colorless viscous oil (218 mg). $^1$H NMR (400 MHz, CDCl$_3$): 7.31 (d, J=8.4 Hz, 2H), 7.13-7.06 (m, 3H), 7.01-6.96 (m, 1H), 6.91-6.86 (m, 2H), 4.12 (t, J=6.1 Hz, 2H), 3.62 (s, 4H), 2.90 (t, J=5.7 Hz, 2H), 2.81-2.71 (m, 4H), 2.56-2.47 (m, 4H), 1.66-1.57 (m, 4H), 1.50-1.42 (m, 2H).

Example 22

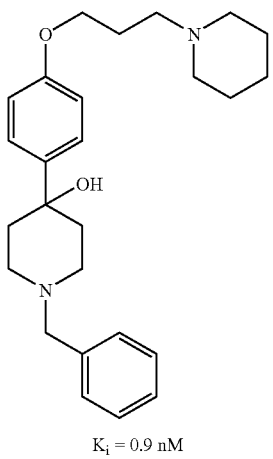

$K_i = 0.9$ nM

1-Benzyl-4-[4-(3-piperidin-1-yl-propoxy)-phenyl]-piperidin-4-ol

A solution of the product of Example 5 (297 mg) in tetrahydrofuran (2 mL) was cooled in a dry-ice/acetone bath and treated with n-butyllithium (0.44 mL of a 2.5 M solution in hexane). After 30 min, the resulting solution was treated with a solution of 1-benzyl-4-piperidone (0.19 mL) in tetrahydrofuran (1 mL). After 15 min, the reaction was allowed to warm to room temperature, and quenched with water (3 mL). Volatiles were removed in vacuo, and the residue was extracted with ether (3×5 mL). The combined organic phases were dried (magnesium sulfate) and evaporated in vacuo. Silica gel chromatography of the residue (3% 2M ammonia-methanol/dichloromethane) gave the title compound as a white microcrystalline solid (80 mg). $^1$H NMR (400 MHz, CDCl$_3$): 7.42-7.22 (m, 7H), 6.86 (d, J=8.8 Hz, 2H), 3.97 (t, J=6.4 Hz, 2H), 3.57 (s, 2H), 2.79-2.72 (m, 2H), 2.50-2.33 (m, 7H), 2.16-2.06 (m, 2H), 1.99-1.91 (m, 2H), 1.77-1.65 (m, 3H), 1.61-1.54 (m, 4H), 1.47-1.39 (m, 2H)

Example 23

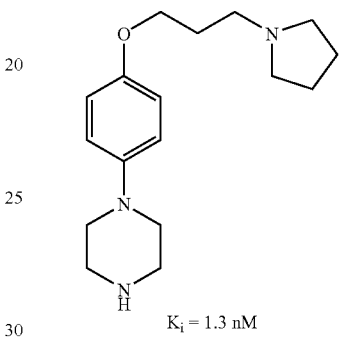

$K_i = 1.3$ nM

1-[4-(3-Pyrrolidin-1-yl-propoxy)-phenyl]-piperazine hydrochloride

A solution of the product of Example 7 (300 mg) in dioxane (5 mL) was treated with a solution of 4N hydrogen chloride in dioxane (2 mL) for 48 h. Volatiles were removed in vacuo, and the residue was triturated with ether, giving the title compound as an ivory solid (230 mg). $^1$H NMR (400 MHz, MeOH-d$_4$): 7.35-7.33 (d, J=8.9 Hz, 2H), 7.05-7.03 (d, J=8.9 Hz, 2H), 4.13 (t, J=5.5 Hz, 2H), 3.73-3.69 (m, 2H), 3.60(bs, 8H), 3.45-3.41 (m, 2H), 3.16-3.11 (m, 2H), 2.27-2.15 (m, 4H), 2.10-2.05 (m, 2H)

Example 24

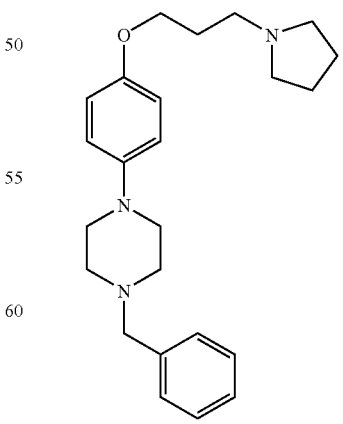

$K_i = 1.3$ nM

1-Benzyl-4-[4-(3-pyrrolidin-1-yl-propoxy)-phenyl]-piperazine

A solution of the product of Example 23 (148 mg), benzaldehyde (520 mg), and acetic acid (25 mg) in dichloroethane (3 mL) was treated with sodium triacetoxyborohydride (121 mg). After 14 h, the reaction was quenched with saturated aqueous sodium bicarbonate, and the aqueous phase was extracted with dichloromethane (120 mL). The organic phase was dried (magnesium sulfate) and evaporated in vacuo. Silica gel chromatography of the residue (5% 2M ammonia-methanol/dichloromethane) gave the title compound as a light yellow solid (8 mg). $^1$H NMR (400 MHz, CDCl$_3$): 7.36-7.24 (m, 5H), 6.94-6.81 (m, 4H), 3.96 (t, J=6.4 Hz, 2H), 3.56 (s, 2H), 3.08 (t, J=4.9 Hz, 4H), 2.64-2.60 (m, 4H), 2.04-1.94 (m, 2H), 1.80-1.75 (m, 4H).

Example 25

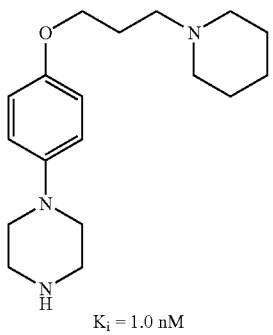

$K_i = 1.0$ nM

1-[4-(3-Piperidin-1-yl-propoxy)-phenyl]-piperazine hydrochloride

A solution of the product of Example 8 (520 mg) in dioxane (6 mL) was treated with a solution of 4N hydrogen chloride in dioxane (4 mL) for 48 h. Volatiles were removed in vacuo, and the residue was triturated with ether, giving the title compound as an ivory solid (750 mg). $^1$H NMR (400 MHz, MeOH-d$_4$): 7.16-7.14 (d, J=9.0 Hz, 5H), 6.84-6.96 (d, J=8.9 Hz, 4H), 4.10 (t, J=5.6 Hz, 2H), 3.62 (d, J=12.0 Hz, 2H), 3.00 (t, J=12.1 Hz, 2H), 2.67-2.21 (m, 2H), 2.01-1.98 (m, 2H), 1.90-1.76 (m, 3H), 1.70-1.52 (m, 1H).

Example 26

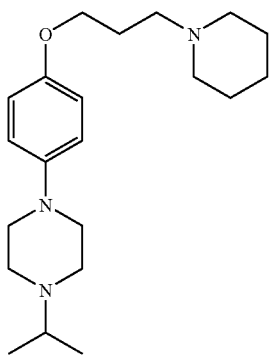

$K_i = 0.3$ nM

1-Isopropyl-4-[4-(3-piperidin-1-yl-propoxy)-phenyl]-piperazine

A solution of the product of Example 25 (122 mg), acetone (23 mg), and acetic acid (19 mg) in dichloroethane (3 mL) was treated with sodium triacetoxyborohydride (96 mg). After 14 h, the reaction was quenched with saturated aqueous sodium bicarbonate, and the aqueous phase was extracted with dichloromethane (120 mL). The organic phase was dried (magnesium sulfate) and evaporated in vacuo. Silica gel chromatography of the residue (5% 2M ammonia-methanol/dichloromethane) gave the title compound as a white solid (31 mg). $^1$H NMR (400 MHz, CDCl$_3$): 6.91-6.87 (m, 2H), 6.85-6.81 (m, 2H), 3.95 (t, J=6.4 Hz, 2H), 3.10 (t, J=4.9 Hz, 4H), 2.69 (t, J=4.9 Hz, 4H), 2.48-2.44 (m, 2H), 2.39 (bs, 4H), 1.98-1.91 (m, 2H), 1.61-1.56 (m, 4H), 1.46-1.40 (m, 2H), 1.09 (d, J=6.5 Hz, 6H).

Example 27

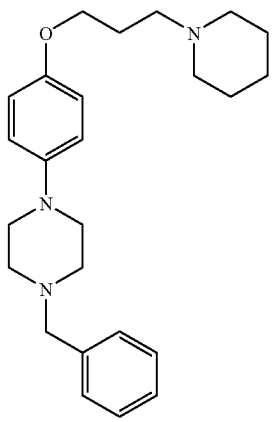

$K_i = 3.0$ nM

1-Benzyl-4-[4-(3-piperidin-1-yl-propoxy)-phenyl]-piperazine

A solution of the product of Example 25 (151 mg), benzaldehyde (54 mg), and acetic acid (24 mg) in dichloroethane (3 mL) was treated with sodium triacetoxyborohydride (119 mg). After 14 h, the reaction was quenched with saturated aqueous sodium bicarbonate, and the aqueous phase was extracted with dichloromethane (120 mL). The organic phase was dried (magnesium sulfate) and evaporated in vacuo. Silica gel chromatography of the residue (5% 2M ammonia-methanol/dichloromethane) gave the title compound as an ivory solid (73 mg). $^1$H NMR (400 MHz, CDCl$_3$): 7.36-7.24 (m, 5H), 6.89-6.80 (m, 4H), 3.94 (t, J=6.4 Hz, 2H), 3.56 (s, 2H), 3.08 (t, J=4.9 Hz, 4H), 2.61 (t, J=5.0 Hz, 4H), 2.48-2.44 (m, 2H), 2.39 (bs, 4H), 1.98-1.91 (m, 2H), 1.61-1.56 (m, 4H), 1.46-1.40 (m, 2H).

Example 28

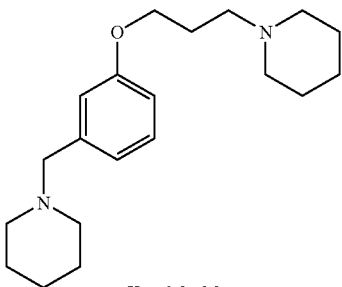

$K_i = 0.3$ nM

4-[3-(3-Piperidin-1-ylmethyl-phenoxy)-propyl]-morpholine dihydrochloride

A solution of the product of Example 10 (1.0 g), piperidine (0.55 mL), and acetic acid (0.29 mL) in DCE (10 mL) was treated with sodium triacetoxyborohydride (1.5 g). After 16 h, saturated aqueous sodium bicarbonate was added. The resulting mixture was extracted with DCM (3×10 mL). The combined organic phases were dried (magnesium sulfate) and evaporated, giving a material which was dissolved in n-butanol (20 mL), treated with piperidine (0.65 mL), sodium carbonate (800 mg), and potassium iodide (42 mg), and heated to 105° C. After 16 h, the reaction was cooled to RT, treated with water (10 mL), and extracted with DCM (3×20 mL). The combined organic phases were dried (magnesium sulfate) and evaporated. The residue was treated with ether (20 mL), and filtered. The filtrate was treated with hydrogen chloride (2.5 mL of a 2 M solution in ether) followed by methanol (3 mL). The resulting solution was stirred for 1 h, and evaporated. Methanol (10 mL) was added, and the resulting suspension was heated to dissolve all solids. The mixture was cooled to RT, and ether (30 mL) was slowly added. Filtration gave the title compound as an amorphous white powder (0.74 g). $^1$H NMR (400 MHz, MeOH-$d_4$): 7.19 (t, J=8.1 Hz, 1H), 6.89-6.87 (m, 2H), 6.79-6.76 (m, 1H), 4.00 (t, J=6.4 Hz, 2H), 3.43 (s, 2H), 2.47 (d, J=7.6 Hz, 10H), 2.04-1.94 (m, 2H), 1.62-1.54 (m, 8H), 1.45-1.42 (m, 4H).

Example 29

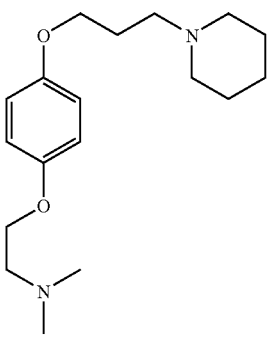

$K_i = 2.3$ nM

Dimethyl-{2-[4-(3-piperidin-1-yl-propoxy)-phenoxy]-ethyl}-amine

A suspension of the product of Example 15 (217 mg), 2-piperidylethan-1-ol (119 mg), and polymer-supported triphenylphosphine (613 mg, 3 mmol/g phosphorus content) in dichloromethane (4 mL) was treated with a solution of di-tert-butyl azodicarboxylate (318 mg) in dichloromethane (1 mL). The resulting mixture was stirred for 3 h and filtered. Chromatography of the filtrate (2% 2M ammonia-methanol/dichloromethane) gave the title compound as a white waxy solid (58 mg). $^1$H NMR (400 MHz, CDCl$_3$): 6.86-6.79 (m, 4H), 4.01 (t, J=5.7 Hz, 2H), 3.94 (t, J=6.4 Hz, 2H), 2.70 (t, J=5.8 Hz, 2H), 2.51-2.37 (m, 6H), 2.33 (s, 6H), 2.00-1.92 (m, 2H), 1.64-1.57 (m, 4H), 1.47-1.40 (m, 2H).

Example 30

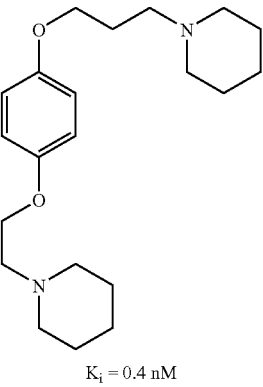

$K_i = 0.4$ nM

1-{3-[4-(2-Piperidin-1-yl-ethoxy)-phenoxy]-propyl}-piperidine

A suspension of the product of Example 15 (217 mg), 2-piperidylethan-1-ol (119 mg), and polymer-supported triphenylphosphine (613 mg, 3 mmol/g phosphorus content) in dichloromethane (4 mL) was treated with a solution of di-tert-butyl azodicarboxylate (318 mg) in dichloromethane (1 mL). The resulting mixture was stirred for 3 h and filtered. Chromatography of the filtrate (2% 2M ammonia-methanol/dichloromethane) gave the title compound as a white waxy solid (58 mg). $^1$H NMR (400 MHz, CDCl$_3$): 6.82 (s, 4H), 4.05 (t, J=6.2 Hz, 2H), 3.94 (t, J=6.5 Hz, 2H), 2.74 (t, J=6.2 Hz, 2H), 2.53-2.30 (m, 10H), 1.99-1.90 (m, 2H), 1.64-1.55 (m, 8H), 1.49-1.39 (m, 4H).

Example 31

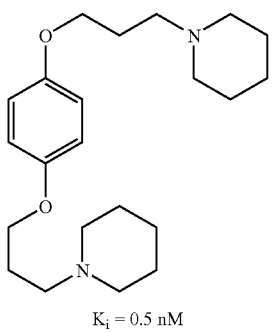

$K_i = 0.5$ nM

1-{3-[4-(3-Piperidin-1-yl-propoxy)-phenoxy]-propyl}-piperidine

A suspension of the product of Example 15 (132 mg), 1-(3-hydroxypropyl)piperidine (132 mg), and polymer-supported triphenylphosphine (613 mg, 3 mmol/g phosphorus content) in dichloromethane (4 mL) was treated with a solution of di-tert-butyl azodicarboxylate (318 mg) in dichloromethane (1 mL). The resulting mixture was stirred for 3 h and filtered. Chromatography of the filtrate (2% 2M ammonia-methanol/dichloromethane) gave the title compound as a waxy solid (39 mg). $^1$H NMR (400 MHz, CDCl$_3$): 6.81 (s, 4H), 3.94 (t, J=3.94, 4H), 2.49-2.34 (m, 12H), 1.99-1.90 (m, 4H), 1.63-1.55 (m, 8H), 1.47-1.40 (m, 4H).

Example 32

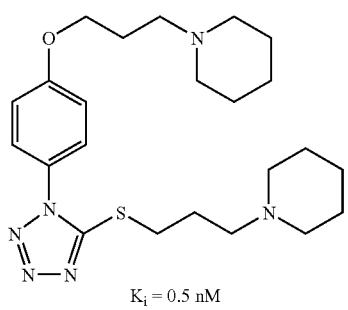

$K_i = 0.5$ nM 1-(3-{4-[5-(3-Piperidin-1-yl-propylsulfanyl)-tetrazol-1-yl]-phenoxy}-propyl)-piperidine A suspension of 1-(4-hydroxyphenyl)-1H-tetrazole-5-thiol (175 mg), the product of Example 1 (256 mg), and polymer-supported triphenylphosphine (600 mg, 3 mmol/g phosphorus content) in dichloromethane (5 mL) was treated with di-tert-butyl azodicarboxylate (456 mg). The resulting mixture was stirred for 24 h and filtered. Chromatography of the filtrate (5% 2M ammonia-methanol/dichloromethane) gave the title compound as a colorless oil (25 mg). $^1$H NMR (400 MHz, CDCl$_3$): 7.40-7.35 (m, 2H), 7.07-6.94 (m, 2H), 4.00 (t, J=6.4 Hz, 2H), 3.33 (t, J=7.1 Hz, 2H), 2.43-2.40 (m, 2H), 2.36-2.29 (m, 10H), 1.97-1.89 (m, 4H), 1.56-1.46 (m, 8H), 1.40-1.35 (m, 4H).

Example 33

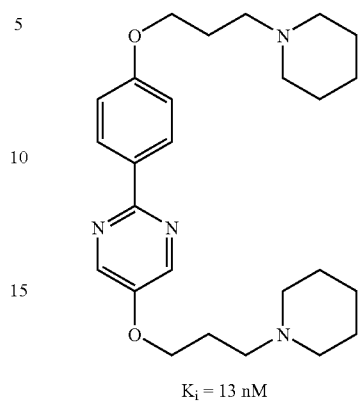

$K_i = 13$ nM 5-(3-Piperidin-1-yl-propoxy)-2-[4-(3-piperidin-1-yl-propoxy)-phenyl]-pyrimidine A suspension of 2-(4-hyroxyphenyl)-5-pyrimidinol (169 mg), the product of Example 1 (256 mg), and polymer-supported triphenylphosphine (600 mg, 3 mmol/g phosphorus content) in dichloromethane (5 mL) was treated with di-tert-butyl azodicarboxylate (456 mg). The resulting mixture was stirred for 24 h and filtered. Chromatography of the filtrate (5% 2M ammonia-methanol/dichloromethane) gave the title compound as a white solid (6.7 mg). $^1$H NMR (400 MHz, CDCl$_3$): 8.24 (s, 2H), 8.06 (d, J=8.8 Hz, 2H), 6.77 (d, J=8.8 Hz, 2H), 4.10 (t, J=6.1 Hz, 2H), 3.82 (t, J=5.2 Hz, 2H), 2.60-2.36 (m, 12H), 2.07-2. (m, 2H), 1.73-1.63 (m, 6H), 1.61-1.55 (m, 4H), 1.48-1.44 (m, 4H).

Example 34

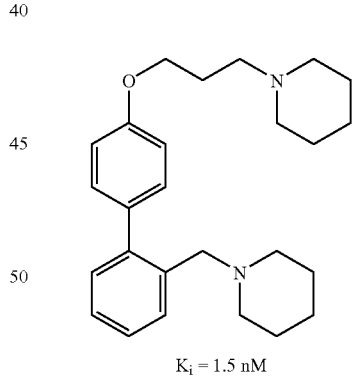

$K_i = 1.5$ nM

1-[3-(2'-Piperidin-1-ylmethyl-biphenyl-4-yloxy)-propyl]-piperidine

The product of Example 16 (75 mg), was treated with 1 mL of a solution prepared from piperidine (0.28 mL) and acetic acid (0.29 mL) in dichloroethane (10 mL). The resulting solution was treated with sodium triacetoxyborohydride (68 mg). After 16 h, the reaction was quenched with saturated aqueous sodium bicarbonate, and the aqueous phase was extracted with dichloromethane (3×1 mL). The combined organic phases were dried (magnesium sulfate) and evaporated in vacuo. Silica gel chromatography of the residue (4% 2M ammonia-methanol/dichloromethane) gave the title compound as a colorless oil (43 mg). ¹H NMR (400 MHz, CDCl₃): 7.52 (dd, J=6.9, 2.0 Hz, 1H), 7.34-7.20 (m, 5H), 6.92 (d, J=6.92 Hz, 2H), 4.05 (t, J=4.5 Hz, 2H), 2.35 (s, 2H), 2.54-2.25 (m, 10H), 2.06-1.98 (m, 2H), 1.64-1.35 (m, 12H).

Example 35

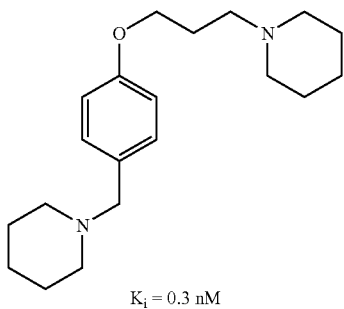

K<sub>i</sub> = 0.3 nM

1-[3-(4-Piperidin-1-ylmethyl-phenoxy)-propyl]-piperidine

A solution of the product of Example 12 (6.13 g), piperidine (3.0 mL), sodium carbonate (3.6 g), and potassium iodide (190 mg) in n-butanol (50 mL) was heated to 105° C. for 21 h, cooled to RT, and treated with water (50 mL). The resulting mixture was extracted with DCM (4×50 mL), and the combined organic phases were dried (magnesium sulfate) and evaporated. Chromatography of the residue (5% 2M methanolic ammonia/methanol) gave the title compound as a waxy solid (3.2 g). ¹H NMR (400 MHz, CDCl₃): 7.19 (d, J=8.6 Hz, 2H), 6.83 (d, J=8.8 Hz, 2H), 3.97 (t, J=6.5 Hz, 2H), 3.4 (s, 2H), 2.48-2.31 (m, 10H), 2.00-1.92 (m, 2H), 1.62-1.52 (m, 8H), 1.47-1.38 (m, 4H).

Example 36

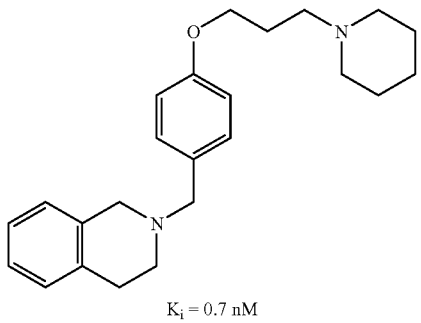

K<sub>i</sub> = 0.7 nM

2-[4-(3-Piperidin-1-yl-propoxy)-benzyl]-1,2,3,4-tetrahydro-isoquinoline

A solution of the product of Example 11 (1.0 g), 1,2,3,4-tetrahydro-isoquinoline (0.0.69 mL), and acetic acid (0.29 mL) in DCE (10 mL) was treated with sodium triacetoxyborohydride (1.5 g). After 16 h, saturated aqueous sodium bicarbonate was added. The resulting mixture was extracted with DCM (3×10 mL). The combined organic phases were dried (magnesium sulfate) and evaporated, giving a material which was dissolved in n-butanol (20 mL), treated with piperidine (0.65 mL), sodium carbonate (800 mg), and potassium iodide (42 mg), and heated to 105° C. After 16 h, the reaction was cooled to RT, treated with water (10 mL), and extracted with DCM (3×20 mL). The combined organic phases were dried (magnesium sulfate) and evaporated. The residue was treated with ether (20 mL), and filtered. The filtrate was treated with hydrogen chloride (2.5 mL of a 2 M solution in ether) followed by methanol (3 mL). The resulting solution was stirred for 1 h, and evaporated. The residue was dried in vacuo, and ether was added, followed by enough methanol to cause a precipitate to form. Filtration gave the title compound as an amorphous pink powder (0.86 g). ¹H NMR (400 MHz, CDCl₃): 7.27 (d, J=8.6 Hz, 2H), 7.13-7.05 (m, 4H), 6.99-6.96 (m, 1H), 6.89-6.83 (m, 2H), 4.00 (t, J=6.3 Hz, 2H), 3.60 (s, 4H), 2.89 (t, J=5.7 Hz, 2H), 2.72 (t, J=5.8 Hz, 2H), 2.53-2.37 (m, 6H), 2.03-1.95 (m, 2H), 1.64-1.57 (m, 4H), 1.49-1.40 (m, 2H).

Example 37

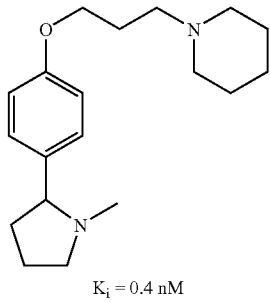

K<sub>i</sub> = 0.4 nM

1-{3-[4-(1-Methyl-pyrrolidin-2-yl)-phenoxy]-propyl}-piperidine

The product of Example 5 (0.345 g) in diethylether (10 mL) was cooled to −78° C. and treated with n-butyllithium (0.5 mL, 2.5 M in hexane) and stirred at −78° C. for an additional 10 minutes whereupon the reaction mixture was warmed to 0° C. for 2-3 minutes then recooled to −78° C. To the cold solution was then added N-methylpyrrolidinone (0.099 g) and the reaction mixture warmed to ambient temperature. Separately a solution of sodium borohydride (0.04 g) and trifluoroacetic acid (0.08 mL) in diethylether (5 mL) was prepared and the reaction mixture added to this solution dropwise with rapid stirring. After 75 minutes the reaction mixture was treated with a solution of 20% sodium carbonate and extracted with ethyl acetate (3×25 mL). The organic extracts were combined, dried over sodium sulfate, filtered and evaporated. The residue was purified by silica gel chromatography (4% methanolic ammonia/DCM) to give the title compound (0.03 g). ¹H NMR (400 MHz, CDCl₃): 7.21(d, J=8.3Hz, 2H), 6.85 (d, J=8.3 Hz, 2H), 3.98 (t, J=6.3, 6.56 Hz, 2H), 3.20 (t, J=8.5 Hz, 1H), 2.95 (t, J=8.3 Hz, 1H), 2.17-2.57 (m, 7H), 2.11 (s, 3H), 1.95 (m, 3H), 1.74 (m, 3H), 1.57 (m, 4H), 1.37-1.48 (m, 2H).

Example 38

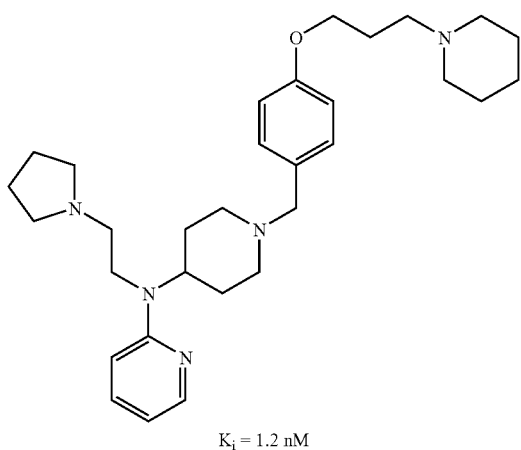

$K_i = 1.2$ nM

{1-[4-(3-Piperidin-1-yl-propoxy)-benzyl]-piperidin-4-yl}-pyridin-2-yl-(2-pyrrolidin-1-yl-ethyl)-amine A solution of the product of Example 9 (30 mg), piperidin-4-yl-pyridin-2-yl-(2-pyrrolidin-1-yl-ethyl)-amine (29.8 mg), and acetic acid (0.015 mL) in DCM (1 mL) was treated with sodium triacetoxyborohydride (38 mg). After 16 h, the resulting mixture was treated with 10% sodium hydroxide (1 mL) and extracted with DCM (3×3 mL). The combined organic phases were dried (sodium sulfate) and evaporated. Chromatography of the residue (1-10% 2 M methanolic ammonia/DCM) gave the title compound as a colorless oil (26 mg). $^1$H NMR (400 MHz, CDCl$_3$): 8.12 (m, 1H), 7.39 (m, 1H), 7.21 (d, J=8.6 Hz, 2H), 6.85 (d, J=8.6 Hz, 2H), 6.53-6.47 (m, 2H), 4.44 (m, 1H), 3.99 (t, J=6.3 Hz, 2H), 3.51-3.47 (m, 2H), 3.46 (s, 2H), 2.95 (m, 2H), 2.62 (m, 6H), 2.49 (m, 2H), 2.42 (m, 4H), 2.12 (m, 2H), 1.98 (m, 2H), 1.84-1.78 (m, 5H), 1.75 (m, 1H), 1.68 (m, 2H), 1.63-1.57 (m, 4H), 1.44 (m, 2H).

Example 39

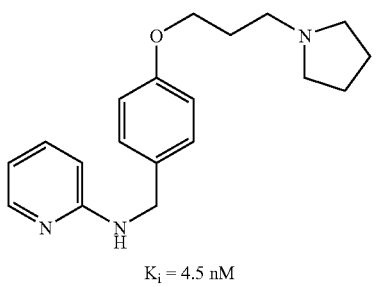

$K_i = 4.5$ nM

Pyridin-2-yl-[4-(3-pyrrolidin-1-yl-propoxy)-benzyl]-amine

A solution of 4-(3-Pyrrolidin-1-yl-propoxy)-benzaldehyde (0.51 g), 2-aminopyridine (0.24 g), and acetic acid (0.13 mL) in DCM (7 mL) was treated with sodium triacetoxyborohydride (650 mg). After 16 h, the resulting mixture was treated with 10% sodium hydroxide (10 mL) and extracted with DCM (3×10 mL). The combined organic phases were dried (sodium sulfate) and evaporated. Chromatography of the residue (1-4% 2 M methanolic ammonia/DCM) gave the title compound as an off white solid (500 mg). $^1$H NMR (400 MHz, CDCl$_3$): 8.09 (m, 1H), 7.39 (m, 1H), 7.26 (d, J=8.8 Hz, 2H), 6.86 (d, J=8.8 Hz, 2H), 6.58 (m, 1H), 6.36 (m, 1H), 4.79 (m, 1H), 4.41 (d, J=5.5, 2H), 4.01 (t, J=6.3 Hz, 2H), 2.63 (t, J=7.6 Hz, 2H), 2.54 (m, 4H), 2.04-1.96 (m, 2H), 1.79 (m, 4H).

Example 40

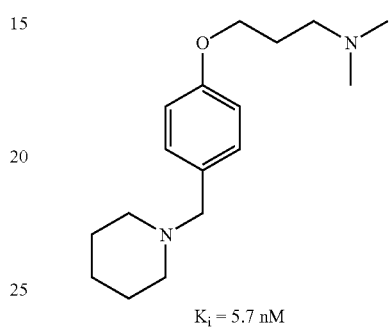

$K_i = 5.7$ nM

Dimethyl-[3-(4-piperidin-1-ylmethyl-phenoxy)-propyl]-amine

A suspension of 3-dimethylamino-1-propanol (0.178 mL), the product of example Example 17 (191 mg), polymer supported triphenyl phosphine (667 mg; loading: 3 mmol/g) and di-tert-butylazodicarboxylate (345 mg) in DCM (15 mL) was shaken for 16 h. The resulting mixture was filtered through a pad of ceilite and washed with DCM (3×3 mL). The combined filtrates were concentrated. Chromatography of the residue (1-6% 2 M methanolic ammonia/DCM) gave the title compound as a colorless oil (90 mg). $^1$H NMR (400 MHz, CDCl$_3$): 7.20 (d, J=8.6 Hz, 2H), 6.84 (d, J=8.6 Hz, 2H), 4.00 (d, J=6.5 Hz, 1H), 3.40 (s, 2H), 2.44 (t, J=7.4, 2H), 2.35 (bs, 4H), 2.25 (s, 6H), 1.98-1.91 (m, 2H), 1.58-1.53 (m, 4H), 1.44-1.39 (m, 2H).

Example 41

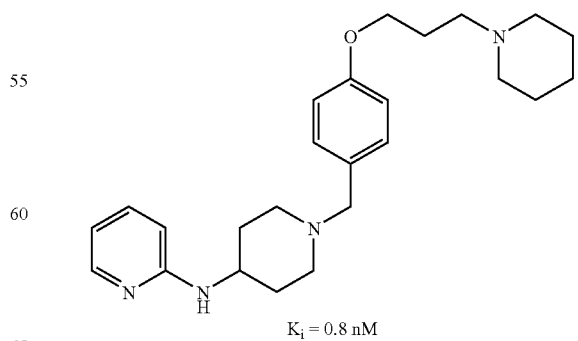

$K_i = 0.8$ nM

{1-[4-(3-Piperidin-1-yl-propoxy)-benzyl]-piperidin-4-yl}-pyridin-2-yl-amine

A solution of the product of Example 9 (240 mg), piperidin-4-yl-pyridin-2-yl-amine (166 mg), and acetic acid (0.12 mL) in DCM (5 mL) was treated with sodium triacetoxyborohydride (290 mg). After 16 h, the resulting mixture was treated with 10% sodium hydroxide (7 mL) and extracted with DCM (3×10 mL). The combined organic phases were dried (sodium sulfate) and evaporated. Chromatography of the residue (3% 2 M methanolic ammonia/DCM) gave the title compound as a colorless oil (188 mg). $^1$H NMR (400 MHz, CDCl$_3$): 8.06 (m, 1H), 7.38 (m, 1H), 7.20 (d, J=8.8 Hz, 2H), 6.84 (d, J=8.8 Hz, 2H), 6.53 (m, 1H), 6.34 (d, J=8.3 Hz, 1H), 4.36 (br, m, 1H), 3.99 (t, J=6.6 Hz, 2H), 3.60 (m, 1H), 3.45 (s, 2H), 2.81 (m, 2H), 2.47 (m, 2H), 2.47 (br, 3H), 2.15 (m, 2H), 2.05-1.93 (m, 4H), 1.62-1.54 (m, 4H), 1.50 (m, 1H), 1.44 (m, 2H).

Example 42

Example 43

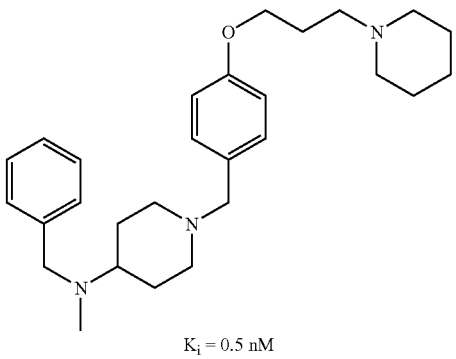

K$_i$ = 0.5 nM

Benzyl-methyl-{1-[4-(3-piperidin-1-yl-propoxy)-benzyl]-piperidin-4-yl}-amine

A solution of the product of Example 9 (155 mg), benzyl-methyl-piperidin-4-yl-amine (123 mg), and acetic acid (0.11 mL) in DCM (3 mL) was treated with sodium triacetoxyborohydride (190 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (155 mg). $^1$H NMR (400 MHz, CDCl$_3$): 7.31-7.28 (m, 4H), 7.24-7.18 (m, 3H), 6.84 (d, J=8.8 Hz, 2H), 3.99 (t, J=6.3 Hz, 2H), 3.56 (s, 2H), 3.42 (s, 2H), 2.94 (m, 2H), 2.47 (m, 2H), 2.40 (m, 4H), 2.19 (s, 3H), 2.01-1.88 (m, 4H), 1.77 (m, 2H), 1.67 (m, 2H), 1.59 (m, 4H), 1.44 (m, 2H)

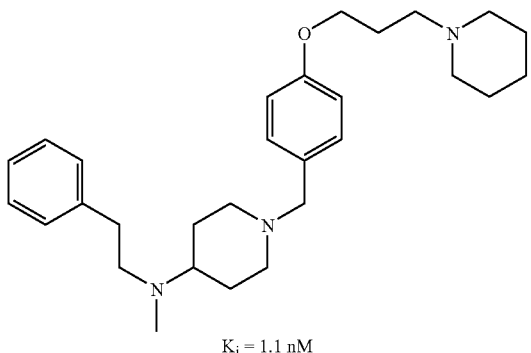

K$_i$ = 1.1 nM

Methyl-phenethyl-{1-[4-(3-piperidin-1-yl-propoxy)-benzyl]-piperidin-4-yl}-amine

A solution of the product of Example 9 (152 mg), methyl-phenethyl-piperidin-4-yl-amine (128 mg), and acetic acid (0.11 mL) in DCM (3 mL) was treated with sodium triacetoxyborohydride (190 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (148 mg). $^1$H NMR (400 MHz, CDCl$_3$): 7.29-7.25 (m, 2H), 7.21-7.16 (m, 5H), 6.83 (j, J=8.6 Hz, 2H), 3.99 (d, J=6.3 Hz, 2H), 3.41 (s, 2H), 2.92 (m, 2H), 2.77-2.66 (m, 4H), 2.47 (m, 2H), 2.40 (m, 4H), 2.34 (s, 3H), 2.00-1.88 (m, 4H), 1.71 (m, 2H), 1.62-1.55 (m, 6H), 1.44 (m, 2H).

Example 44

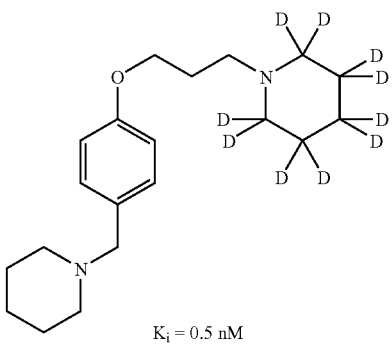

K$_i$ = 0.5 nM

1-[3-(4-Piperidin-1-ylmethyl-phenoxy)-propyl]-decadeuterio-piperidine

A suspension of the product of Example 12 (1.0 g), perdeuteropiperidine (0.58 mL), sodium carbonate (3.6 g), and potassium iodide (30 mg) in 1-butanol (15 mL) was heated to 105° C. for 16 h, cooled to RT, diluted with water (6 mL) and extracted with DCM (3×12 mL). The combined organic phases were dried (magnesium sulfate) and evaporated. Chromatography of the residue (3% 2 M methanolic ammonia/DCM) gave the title compound as a yellow oil (872 mg). $^1$H NMR (400 MHz, CDCl$_3$): 7.19 (d, J=8.2 Hz, 2H), 6.84 (d, J=8.4 Hz, 2H), 3.98 (t, J=6.5 Hz, 2H), 3.41 (s, 2H), 2.46 (t, J=7.4 Hz, 2H), 2.38-2.28 (br s, 4H), 2.00-1.92 (m, 2H), 1.59-1.50 (m, 4H), 1.45-1.34 (m, 2H).

Example 45

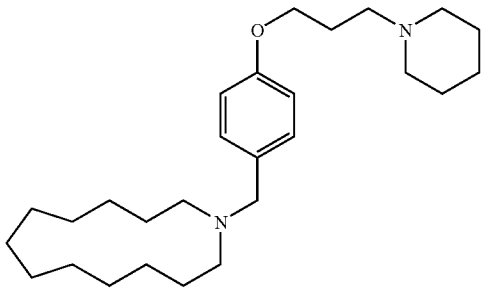

$K_i$ = 2.5 nM

1-[4-(3-Piperidin-1-yl-propoxy)-benzyl]-azacyclotridecane

A solution of the product of Example 9 (175 mg), dodecamethyleneamine (143 mg), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (3% 2 M methanolic ammonia/DCM) gave the title compound as a colorless oil (140 mg). $^1$H NMR (400 MHz, CDCl$_3$): 7.20 (d, J=8.8 Hz 2H), 6.82 (d, J=8.6 Hz, 2H), 3.99 (t, J=6.5 Hz, 2H), 3.40 (s, 2H), 2.50-2.31 (m, 10H), 2.01-1.93 (m, 2H), 1.63-1.56 (m, 4H), 1.48-1.34 (m, 22H).

Example 46

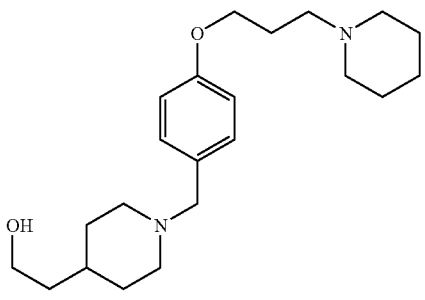

$K_i$ = 1.2 nM

2-{1-[4-(3-Piperidin-1-yl-propoxy)-benzyl]-piperidin-4-yl}-ethanol

A solution of the product of Example 9 (175 mg), 4-hydroxyethylpiperidine (101 mg), (143 mg), and acetic acid (0.02 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (3% 2 M methanolic ammonia/DCM) gave the title compound as a colorless oil (80 mg). $^1$H NMR (400 MHz, CDCl$_3$): 7.19 (d, J=8.6 Hz, 2H), 6.83 (d, J=8.6 Hz, 2H), 3.98 (t, J=6.4 Hz, 2H), 3.65 (t, J=6.7 Hz, 2H), 3.41 (s, 2H), 2.88-2.82 (m, 2H), 2.50-2.33 (m, 7H), 2.01-1.86 (m, 4H), 1.68-1.55 (m, 6H), 1.52-1.37 (m, 5H), 1.31-1.20 (m, 2H).

Example 47

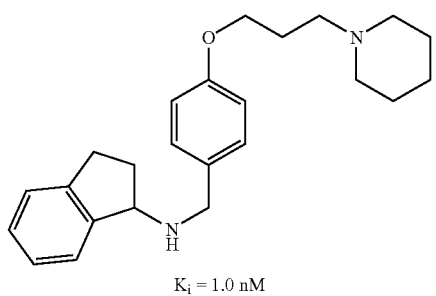

$K_i$ = 1.0 nM

Indan-1-yl-[4-(3-piperidin-1-yl-propoxy)-benzyl]-amine

A solution of the product of Example 9 (175 mg), 1-aminoindane (0.10 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (2.5% 2 M methanolic ammonia/DCM) gave the title compound as a colorless oil (119 mg). $^1$H NMR (400 MHz, CDCl$_3$): 7.37-7.34 (m, 1H), 7.28 (d, J=8.8 Hz, 2H), 7.25-7.17 (m, 3H), 6.86 (d, J=8.8 Hz, 2H), 4.28 (t, J=6.7 Hz, 1H), 3.99 (t, J=6.5 Hz, 2H), 3.86 (d, J=13 Hz, 1H), 3.81 (d, J=13 Hz, 1H), 3.05-2.96 (m, 1H), 2.85-2.76 (m, 1H), 2.49-2.36 (m, 6H), 2.00-1.82 (m, 3H), 1.62-1.55 (m, 4H), 1.47-1.39 (m, 2H)

Example 48

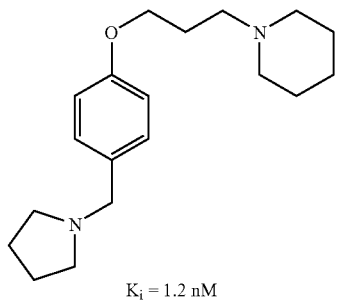

$K_i$ = 1.2 nM

1-[3-(4-Pyrrolidin-1-ylmethyl-phenoxy)-propyl]-piperidine

A solution of the product of Example 9 (175 mg), pyrrolidine (0.07 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (3% 2 M methanolic ammonia/DCM) gave the title compound as a colorless oil (27 mg). $^1$H NMR (400 MHz, CDCl$_3$): 7.21 (d, J=8.6 Hz, 2H), 7.0 (d, J=8.8 Hz, 2H), 3.99 (t, J=6.3 Hz, 2H), 3.52 (s, 2H), 2.50-2.32 (m, 10H), 2.01-1.92 (m, 2H), 1.79-1.72 (m, 4H), 1.61-1.54 (m, 4H), 1.49-1.40 (m, 2H).

Example 49

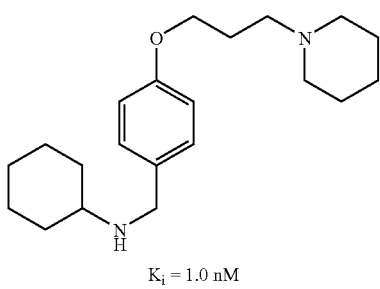

$K_i = 1.0$ nM

Cyclohexyl-[4-(3-piperidin-1-yl-propoxy)-benzyl]-amine

A solution of the product of Example 9 (175 mg), aminocyclohexane (0.09 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (2.5% 2 M methanolic ammonia/DCM) gave the title compound as a colorless oil (84 mg). $^1$H NMR (400 MHz, CDCl$_3$): 7.21 (d, J=8.8 Hz, 2H), 6.84 (d, J=8.6 Hz, 2H), 3.98 (t, J=6.5 Hz, 2H), 3.73 (s, 2H), 2.50-2.35 (m, 7H), 2.00-1.86 (m, 4H), 1.76-1.68 (m, 2H), 1.64-1.55 (m, 5H), 1.47-1.39 (m, 2H), 1.30-1.04 (m, 5H).

Example 50

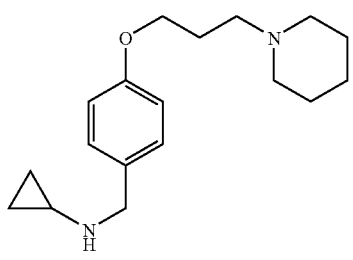

$K_i = 1.0$ nM

Cyclopropyl-[4-(3-piperidin-1-yl-propoxy)-benzyl]-amine

A solution of the product of Example 9 (175 mg), aminocyclopropane (0.05 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (4% 2 M methanolic ammonia/DCM) gave the title compound as a colorless oil (113 mg). $^1$H NMR (400 MHz, CDCl$_3$): 7.20 (d, J=8.8 Hz, 2H), 6.84 (d, J=8.8 Hz, 2H), 3.98 (t, J=6.5 Hz, 2H), 3.76 (s, 2H), 2.49-2.35 (m, 6H), 2.16-2.09 (m, 1H), 2.00-1.92 (m, 2H), 1.62-1.55 (m, 4H), 1.47-1.39 (m, 2H), 0.45-0.34 (m, 4H).

Example 51

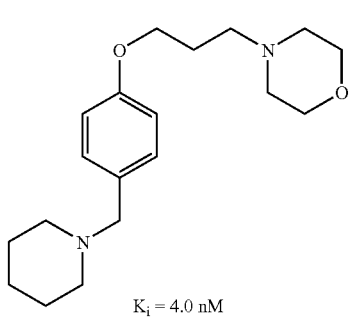

$K_i = 4.0$ nM

4-[3-(4-Piperidin-1-ylmethyl-phenoxy)-propyl]-morpholine

A suspension of the product of Example 12 (268 mg), morpholine (0.11 mL), sodium carbonate (159 g), and potassium iodide (8.3 mg) in 1-butanol (4 mL) was heated to 105 C for 16 h, cooled to RT, diluted with water (2 mL) and extracted with DCM (3×3 mL). The combined organic phases were dried (magnesium sulfate) and evaporated. Chromatography of the residue (2.5% 2 M methanolic ammonia/DCM) gave the title compound as a yellow oil (93 mg). $^1$H NMR (400 MHz, CDCl$_3$): 7.20 (d, J=8.6 Hz, 2H), 6.84 (d, J=8.8 Hz, 2H), 4.01 (t, J=6.5 Hz, 2H), 3.72 (t, J=4.5 Hz, 4H), 3.40 (s, 2H), 2.54-2.44 (m, 6H), 2.34 (br s, 4H), 1.99-1.92 (m, 2H), 1.58-1.52 (m, 4H), 1.45-1.38 (m, 2H).

Example 52

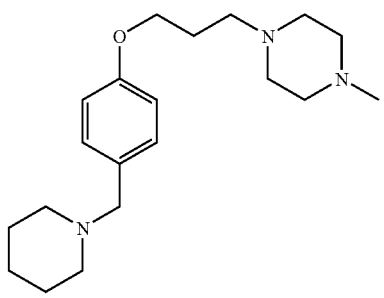

$K_i = 25$ nM

1-Methyl-4-[3-(4-piperidin-1-ylmethyl-phenoxy)-propyl]-piperazine

A suspension of the product of Example 12 (268 mg), N-methylpiperazine (0.14 mL), sodium carbonate (159 g), and potassium iodide (8.3 mg) in 1-butanol (4 mL) was heated to 105° C. for 16 h, cooled to RT, diluted with water (2 mL) and extracted with DCM (3×3 mL). The combined organic phases were dried (magnesium sulfate) and evaporated. Chromatography of the residue (4% 2 M methanolic ammonia/DCM) gave the title compound as a yellow oil (86 mg). $^1$H NMR (400 MHz, CDCl$_3$): 7.19 (d, J=8.6 Hz, 2H), 6.81 (d, J=8.6 Hz, 2H), 3.99 (t, J=6.3 Hz, 2H), 3.40 (s, 2H), 2.53-2.30 (m, 14H), 2.28 (s, 3H), 2.00-1.91 (m, 2H), 1.59-1.50 (m, 4H), 1.44-1.38 (m, 2H).

Example 53

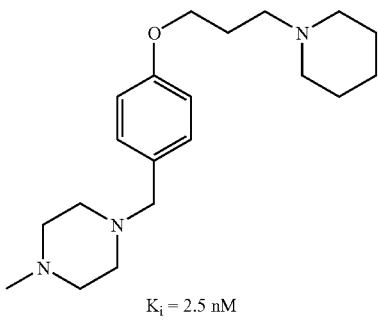

$K_i = 2.5$ nM

1-Methyl-4-[4-(3-piperidin-1-yl-propoxy)-benzyl]-piperazine

A solution of the product of Example 9 (175 mg), N-methylpiperazine (0.09 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (4% 2 M methanolic ammonia/DCM) gave the title compound as a colorless oil (79 mg). $^1$H NMR (400 MHz, CDCl$_3$): 7.20 (d, J=8.6 Hz, 2H), 6.84 (d, J=8.6 Hz, 2H), 3.97 (t, J=6.3 Hz, 2H), 3.43 (s, 2H), 2.50-2.35 (m, 14H), 2.28 (s, 3H), 2.00-1.93 (m, 2H), 1.62-1.55 (m, 4H), 1.47-1.40 (m, 2H).

Example 54

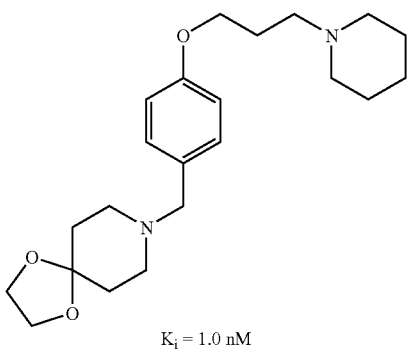

$K_i = 1.0$ nM

8-[4-(3-Piperidin-1-yl-propoxy)-benzyl]-1,4-dioxa-8-aza-spiro[4.5]decane

A solution of the product of Example 9 (175 mg), 1,4-dioxa-8-azaspiro[4.5]-decane (112 mg), and acetic acid (0.01 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (2.5% 2 M methanolic ammonia/DCM) gave the title compound as a colorless oil (68 mg). $^1$H NMR (400 MHz, CDCl$_3$): 7.20 (d, J=8.6 Hz, 2H), 6.84 (d, J=8.6 Hz, 2H), 3.98 (t, J=6.5 Hz, 2H), 3.94 (s, 4H), 3.45 (s, 2H), 2.53-2.35 (m, 10H), 2.00-1.92 (m, 2H), 1.75-1.71 (m, 4H), 1.62-1.55 (m, 4H), 1.47-1.39 (m, 2H).

Example 55

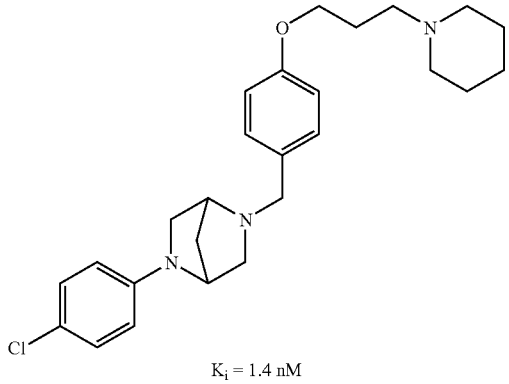

$K_i = 1.4$ nM

2-(4-Chloro-phenyl)-5-[4-(3-piperidin-1-yl-propoxy)-benzyl]-2,5-diaza-bicyclo[2.2.1]heptane A solution of the product of Example 9 (175 mg), 2-phenyl-2,5-diaza-bicyclo[2.2.1]heptane hydrobromide (162 mg), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (2.5% 2 M methanolic ammonia/DCM) gave the title compound as a colorless oil (111 mg). $^1$H NMR (400 MHz, CDCl$_3$): 7.19 (d, J=8.8 Hz, 2H), 7.14 (d, J=9.0 Hz, 2H), 6.82 (d, J=8.6 Hz, 2H), 6.47 (d, J=9.0 H2, 2H), 4.15 (br s, 1H), 3.97 (t, J=6.5 Hz, 2H), 3.59 (s, 2H), 3.52 (br s, 1H), 3.35 (dd, J=8.8, 2.2 Hz, 1H), 3.27 (dd, J=9.0 Hz, 0.8 Hz, 1H), 2.89 (dd, J=9.6, 2.0 Hz, 1H), 2.63 (dd, J=9.6, 1.1 Hz, 1H), 2.48-2.35 (m, 5H), 2.05-1.83 (m, 5H), 1.62-1.54 (m, 4H), 1.47-1.39 (m, 2H).

Example 56

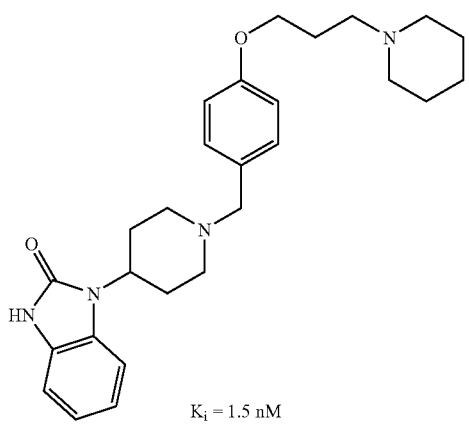

K$_i$ = 1.5 nM

1-{1-[4-(3-Piperidin-1-yl-propoxy)-benzyl]-piperidin-4-yl}-1,3-dihydro-benzoimidazol-2-one A solution of the product of Example 9 (175 mg), 1-piperidin-4-yl-1,3-dihydro-benzoimidazol-2-one (170 mg), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (2.5% 2 M methanolic ammonia/DCM) gave the title compound as a colorless oil (111 mg). $^1$H NMR (400 MHz, CDCl$_3$): 10.47 (br s, 1H), 7.30-7.23 (m, 3H), 7.12-7.01 (m, 3H), 6.86 (d, J=8.8 Hz, 2H), 4.42-4.32 (m, 1H), 4.00 (t, J=6.5 Hz, 2H), 3.51 (s, 2H), 3.07-3.01 (m, 2H), 2.52-2.30 (m, 8H), 2.15 (dd, J=12, 12 Hz, 2H), 2.02-1.94 (m, 2H), 1.83-1.76 (m, 2H), 1.64-1.55 (m, 4H), 1.48-1.40 (m, 2H).

Example 57

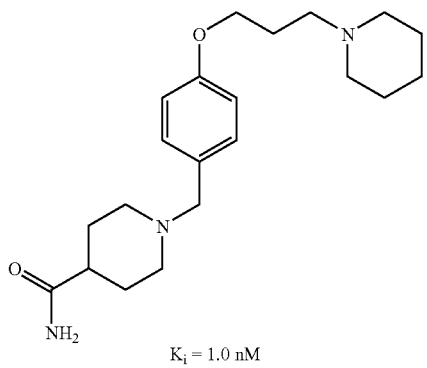

K$_i$ = 1.0 nM

1-[4-(3-Piperidin-1-yl-propoxy)-benzyl]-piperidine-4-carboxylic acid amide

A solution of the product of Example 9 (175 mg), piperidine-4-carboxylic acid amide (100 mg), and acetic acid (0.1 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (5% 2 M methanolic ammonia/DCM) gave the title compound as a colorless oil (84 mg). $^1$H NMR (400 MHz, CDCl$_3$): 7.19 (d, J=8.8 Hz, 2H), 6.84 (d, J=8.6 Hz, 1H), 5.91 (br s, 1H), 5.61 (br s, 1H), 3.99 (t, J=6.4 Hz, 2H), 3.42 (s, 2H), 2.94-2.88 (m, 2H), 2.49-2.35 (m, 6H), 2.17-2.08 (m, 1H), 2.01-1.91 (m, 4H), 1.87-1.67 (m, 4H), 1.62-1.55 (m, 4H), 1.47-1.40 (m, 2H).

Example 58

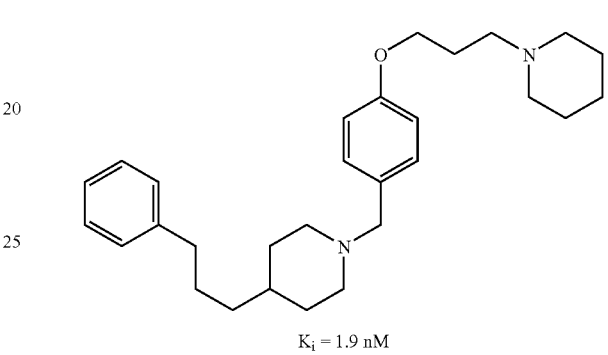

K$_i$ = 1.9 nM

1-[4-(3-Piperidin-1-yl-propoxy)-benzyl]-4-(3-phenyl-propyl)-piperidine

A solution of the product of Example 9 (175 mg), 4-(3-phenyl-propyl)-piperidine (158 mg), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (2% 2 M methanolic ammonia/DCM) gave the title compound as a colorless oil (107 mg). $^1$H NMR (400 MHz, CDCl$_3$): 7.28-7.13 (m, 7H), 6.82 (d, J=8.6 Hz, 2H), 3.97 (t, J=6.3 Hz, 2H), 3.40 (s, 2H), 2.87-2.81 (m, 2H), 2.57 (dd, J=7.7, 7.7 Hz, 2H), 2.49-2.35 (m, 6H), 2.00-1.82 (m, 4H), 1.66-1.55 (m, 8H), 1.47-1.39 (m, 2H), 1.30-1.16 (m, 5H).

Example 59

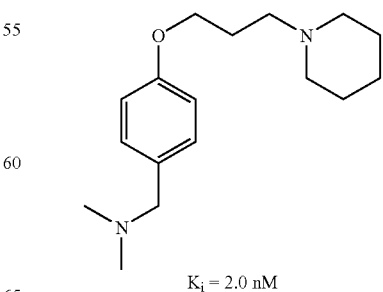

K$_i$ = 2.0 nM

Dimethyl-[4-(3-piperidin-1-yl-propoxy)-benzyl]-amine

A solution of the product of Example 9 (175 mg), dimethylamine hydrochloride (64 mg), and acetic acid (0.05 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (3% 2 M methanolic ammonia/DCM) gave the title compound as a colorless oil (70 mg). $^1$H NMR (400 MHz, CDCl$_3$): 7.19 (d, J=8.6 Hz, 2H), 6.85 (d, J=8.6 Hz, 2H), 3.99 (t, J=6.4 Hz, 2H), 3.35 (s, 2H), 2.50-2.35 (m, 6H), 2.22 (s, 6H), 2.01-1.94 (m, 2H), 1.63-1.55 (m, 4H), 1.46-1.40 (m, 2H).

Example 60

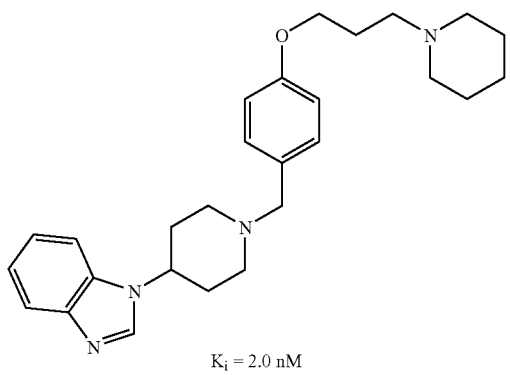

$K_i = 2.0$ nM

1-{1-[4-(3-Piperidin-1-yl-propoxy)-benzyl]-piperidin-4-yl}-1H-benzoimidazole

A solution of the product of Example 9 (82 mg), 1-Piperidin-4-yl-1H-benzoimidazole (62 mg), and acetic acid (0.03 mL) in DCM (3 mL) was treated with sodium triacetoxyborohydride (110 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (81 mg). $^1$H NMR (400 MHz, CDCl$_3$): 7.98 (s, 1H), 7.80 (m, 1H), 7.42 (m, 1H), 7.30-7.20 (m, 4H), 6.87 (d, J=8.6 Hz, 2H), 4.18 (m, 1H), 4.00 (t, J=6.3 Hz, 2H), 3.52 (s, 2H), 3.10-3.03 (m, 2H), 2.48 (m, 2H), 2.41 (br, 4H), 2.21-2.10 (m, 5H), 2.01-1.94 (m, 2H), 1.62-1.55 (m, 4H), 1.47-1.39 (m, 2H).

Example 61

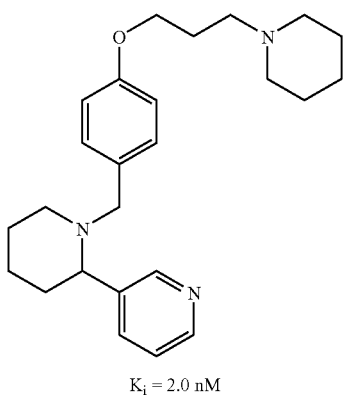

$K_i = 2.0$ nM

1-[4-(3-Piperidin-1-yl-propoxy)-benzyl]-1,2,3,4,5,6-hexahydro-[2,3']bipyridinyl

A solution of the product of Example 9 (174 mg), 1,2,3,4,5,6-hexahydro-[2,3']bipyridinyl (111 mg), and acetic acid (0.05 mL) in DCM (3 mL) was treated with sodium triacetoxyborohydride (240 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (112 mg). $^1$H NMR (400 MHz, CDCl$_3$): 8.63 (m, 1H), 8.49 (m, 1H), 7.80 (m, 1H), 7.27 (m, 1H), 7.11 (d, J=8.6 Hz, 2H) 6.80 (d, J=8.6 Hz, 2H), 3.97 (t, J=6.3 Hz, 2H), 3.61 (d, J=13.4 Hz, 1H), 3.13 (m, 1H), 2.97 (m, 1H), 2.79 (d, J=13.4 Hz, 1H), 2.48 (m, 2H), 2.41 (br, 4H), 2.01-1.98 (m, 5H), 2.01-1.89 (m, 3H), 1.82-1.72 (m, 2H) 1.63-1.51 (m, 4H), 1.48-1.39 (m, 2H).

Example 62

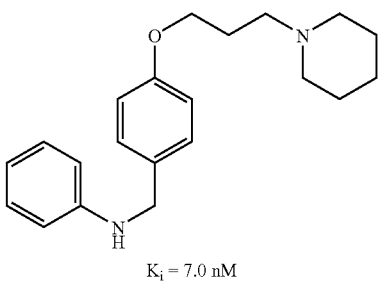

$K_i = 7.0$ nM

Phenyl-[4-(3-piperidin-1-yl-propoxy)-benzyl]-amine

A solution of the product of Example 9 (277 mg), aniline (108 mg), and acetic acid (0.07 mL) in DCM (5 mL) was treated with sodium triacetoxyborohydride (340 mg). After 16 h, the resulting mixture was treated with 10% sodium hydroxide (10 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (256 mg). $^1$H NMR (400 MHz, CDCl$_3$): 7.27 (m, 2H), 7.18 (m, 2H), 6.88 (m, 2H), 6.72 (m, 2H), 6.64 (m, 2H), 4.24 (s, 2H), 4.00 (t, J=6.6 Hz, 2H), 3.94 (br, 1H), 2.48 (m, 2H), 2.41 (br, 4H), 1.98 (m, 2H), 1.64-1.57 (m, 4H), 1.48-1.41 (m, 2H).

Example 63

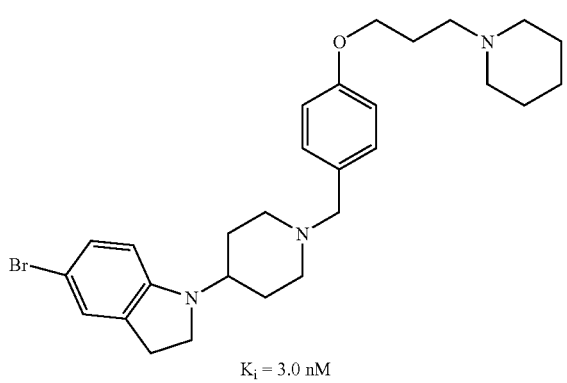

K<sub>i</sub> = 3.0 nM

5-Bromo-1-{1-[4-(3-piperidin-1-yl-propoxy)-benzyl]-piperidin-4-yl}-2,3-dihydro-1H-indole A solution of the product of Example 9 (93 mg) and 5-bromo-1-piperidin-4-yl-2,3-dihydro-1H-indole*2 TFA (191 mg) in DCM (2 mL) was treated with sodium triacetoxyborohydride (150 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (79 mg). $^1$H NMR (400 MHz, CDCl$_3$): 7.20 (d, J=8.6 Hz, 2H), 7.11-7.07 (m, 2H), 6.84 (d, J=8.6 Hz, 2H), 6.23 (d, J=9.1 Hz, 1H), 4.00 (t, J=6.1 Hz, 2H), 3.46 (s, 2H), 3.37 (7, J=8.3 Hz, 2H), 3.28 (m, 1H), 2.97 (m, 2H), 2.90 (t, J=8.3 Hz, 2H), 2.54 (m, 2H), 2.47 (br, 4H), 2.06-1.97 (m, 4H), 1.75-1.60 (m, 8H), 1.50-1.43 (m, 2H).

Example 64

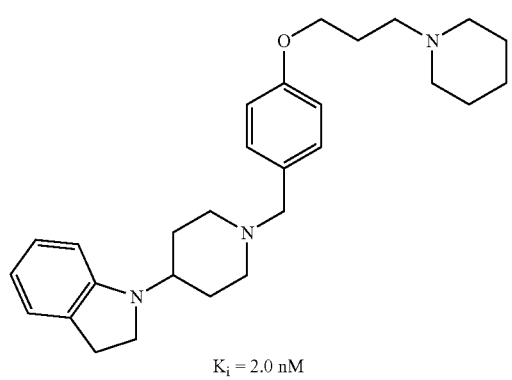

K<sub>i</sub> = 2.0 nM

1-{1-[4-(3-Piperidin-1-yl-propoxy)-benzyl]-piperidin-4-yl}-2,3-dihydro-1H-indole A solution of the product of Example 9 (112 mg) and 1-piperidin-4-yl-2,3-dihydro-1H-indole*2TFA (194 mg) in DCM (2 mL) was treated with sodium triacetoxyborohydride (150 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (78 mg). $^1$H NMR (400 MHz, CDCl$_3$): 7.22 (d, J=8.6 Hz, 2H), 7.06-7.00 (m, 2H), 6.85 (d, J=8.6 Hz, 2H), 6.59 (t, J=7.1 Hz, 1H), 6.39(d, J=7.8 Hz, 1H), 4.00 (t, J=6.3 Hz, 2H), 3.48 (s, 2H), 3.41-3.32 (m, 3H), 2.99 (m, 2H), 2.93 (t, J=8.3 Hz, 2H), 2.54 (m, 2H), 2.47 (br, 4H), 2.09-1.98 (m, 4H), 1.79-1.70 (m, 4H), 1.67-1.61 (m, 4H), 1.50-1.43 (m, 2H).

Example 65

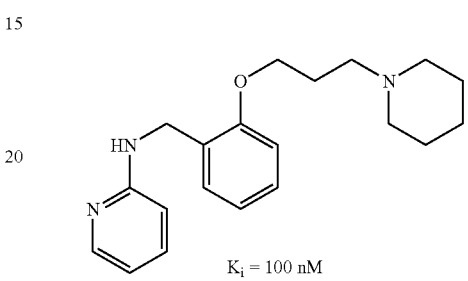

K<sub>i</sub> = 100 nM

[2-(3-Piperidin-1-yl-propoxy)-benzyl]-pyridin-2-yl-amine

A solution of 2-(3-piperidin-1-yl-propoxy)-benzaldehyde (269 mg), 2-aminopyridine (110 mg), and acetic acid (0.07 mL) in DCM (5 mL) was treated with sodium triacetoxyborohydride (410 mg). After 16 h, the resulting mixture was treated with 10% sodium hydroxide (6 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (128 mg). $^1$H NMR (400 MHz, CDCl$_3$): 8.07 (m, 1H), 7.37 (m, 1H), 7.29 (m, 1H), 7.22 (m, 1H), 6.91-6.84 (m, 2H), 6.54 (m, 1H), 6.37 (m, 1H), 5.00 (m, 1H), 4.48 (d, J=5.6, 2H), 4.04 (t, J=6.3 Hz, 2H), 2.52 (m, 2H), 2.41 (br, 4H), 2.02.(m, 2H), 1.64-1.57 (m, 4H), 1.47-1.40 (m, 2H).

Example 66

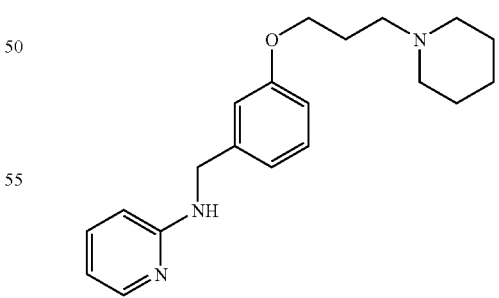

K<sub>i</sub> = 8.0 nM

[3-(3-Piperidin-1-yl-propoxy)-benzyl]-pyridin-2-yl-amine

A solution of the product of Example 13 (262 mg), 2-aminopyridine (104 mg), and acetic acid (0.07 mL) in DCM (5 mL) was treated with sodium triacetoxyborohydride (410 mg). After 16 h, the resulting mixture was treated with 10% sodium hydroxide (6 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (114 mg). $^1$H NMR (400 MHz, CDCl$_3$): 8.10 (m, 1H), 7.39 (m, 1H), 7.22 (m, 1H), 6.94-6.89 (m, 2H), 6.79 (m, 1H), 6.58 (m, 1H), 6.36 (m, 1H), 4.89 (m, 1H), 4.46 (d, J=5.6, 2H), 3.98 (t, J=6.3 Hz, 2H), 2.47 (m, 2H), 2.41 (br, 4H), 1.97 (m, 2H), 1.63-1.56 (m, 4H), 1.47-1.40 (m, 2H).

Example 67

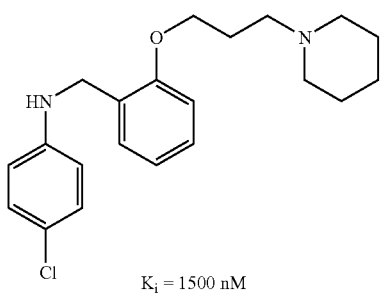

$K_i = 1500$ nM (4-Chloro-phenyl)-[2-(3-piperidin-1-yl-propoxy)-benzyl]-amine

A solution of 2-(3-piperidin-1-yl-propoxy)-benzaldehyde (266 mg), 4-chloroaniline (146 mg), and acetic acid (0.07 mL) in DCM (5 mL) was treated with sodium triacetoxyborohydride (400 mg). After 16 h, the resulting mixture was treated with 10% sodium hydroxide (6 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (246 mg). $^1$H NMR (400 MHz, CDCl$_3$): 7.28-7.20 (m, 2H), 7.09 (d, J=8.9 Hz, 2H), 6.89 (m, 2H), 6.55 (d, J=8.9 Hz, 2H), 4.30 (d, J=5.6, 2H), 4.18 (m, 1H), 4.05 (t, J=6.3 Hz, 2H), 2.47 (m, 2H), 2.37 (br, 4H), 1.96 (m, 2H), 1.62-1.56 (m, 4H), 1.49-1.42 (m, 2H).

Example 68

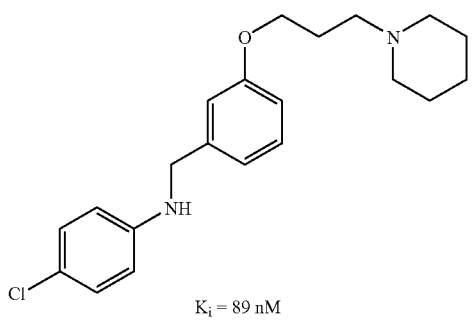

$K_i = 89$ nM (4-Chloro-phenyl)-[3-(3-piperidin-1-yl-propoxy)-benzyl]-amine

A solution of the product of Example 13 (268 mg), 4-chloroaniline (145 mg), and acetic acid (0.07 mL) in DCM (5 mL) was treated with sodium triacetoxyborohydride (400 mg). After 16 h, the resulting mixture was treated with 10% sodium hydroxide (6 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (154 mg). $^1$H NMR (400 MHz, CDCl$_3$): 7.24 (m, 2H), 7.10 (d, J=8.9 Hz, 2H), 6.93-6.88 (m, 2H), 6.81 (m, 1H), 6.54 (d, J=8.9 Hz, 2H), 4.26 (d, J=5.6, 2H), 4.07 (m, 1H), 3.99 (t, J=6.3 Hz, 2H), 2.46 (m, 2H), 2.40 (br, 4H), 1.96 (m, 2H), 1.62-1.56 (m, 4H), 1.49-1.42 (m, 2H).

Example 69

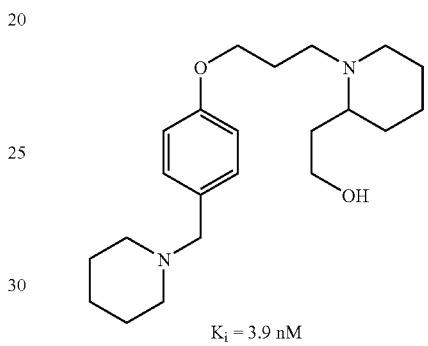

$K_i = 3.9$ nM

2-{1-[3-(4-Piperidin-1-ylmethyl-phenoxy)-propyl]-piperidin-2-yl}-ethanol

A suspension of the product of Example 12 (268 mg), 2-hydroxyethylpiperidine (168 mg), sodium carbonate (159 g), and potassium iodide (8.3 mg) in 1-butanol (4 mL) was heated to 105° C. for 16 h, cooled to RT, diluted with water (2 mL) and extracted with DCM (3×5 mL). The combined organic phases were dried (magnesium sulfate) and evaporated. Chromatography of the residue (4% 2 M methanolic ammonia/DCM) gave the title compound as a colorless glassy solid (53 mg). $^1$H NMR (400 MHz, CDCl$_3$): 7.20 (d, J=8.4 Hz, 2H), 6.83 (d, J=8.4 Hz, 2H), 3.97 (t, J=6.3 Hz, 2H), 3.91-3.84 (m, 1H), 3.78-3.71 (m, 1H), 3.40 (s, 2H), 3.10-2.94 (m, 2H), 2.74-2.64 (m, 2H), 2.39-2.31 (m, 5H), 2.02-1.86 (m, 3H), 1.75-1.35 (m, 14H).

Example 70

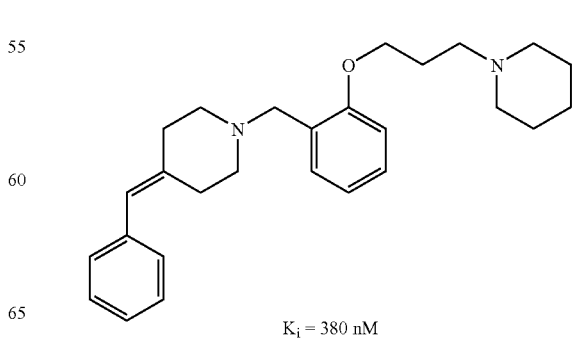

$K_i = 380$ nM

1-{3-[2-(4-Benzylidene-piperidin-1-ylmethyl)-phenoxy]-propyl}-piperidine

A solution of 2-(3-piperidin-1-yl-propoxy)-benzaldehyde (212 mg), 4-benzylidene-piperidine (154 mg), and acetic acid (0.05 mL) in DCM (3 mL) was treated with sodium triacetoxyborohydride (290 mg). After 16 h, the resulting mixture was treated with 10% sodium hydroxide (6 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (148 mg). $^1$H NMR (400 MHz, CDCl$_3$): 7.37 (m, 1H), 7.30 (m, 2H), 7.23-7.16 (m, 4H), 6.92 (m, 1H), 6.86 (m, 1H), 6.27 (s, 1H), 4.00 (t, J=6.3 Hz, 2H), 3.60 (s, 2H), 2.60 (m, 2H), 2.55-2.46 (m, 6H), 2.44-2.37 (m, 6H), 2.00 (m, 2H), 1.64-1.56 (m, 4H), 1.47-1.40 (m, 2H).

Example 71

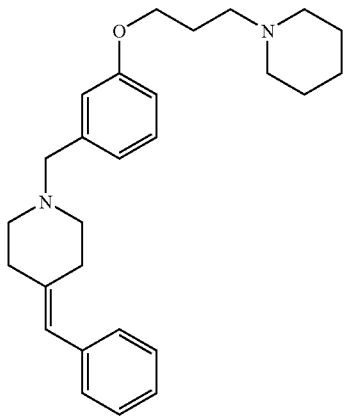

$K_i = 1.8$ nM

1-{3-[3-(4-Benzylidene-piperidin-1-ylmethyl)-phenoxy]-propyl}-piperidine

A solution of the product of Example 13 (210 mg), 4-Benzylidene-piperidine (153 mg), and acetic acid (0.05 mL) in DCM (3 mL) was treated with sodium triacetoxyborohydride (290 mg). After 16 h, the resulting mixture was treated with 10% sodium hydroxide (6 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (189 mg). $^1$H NMR (400 MHz, CDCl$_3$): 7.30 (m, 2H), 7.23-7.16 (m, 3H), 6.89 (m, 2H), 6.79 (m, 1H), 6.27 (s, 1H), 4.00 (t, J=6.3 Hz, 2H), 3.49 (s, 2H), 2.55-2.46 (m, 6H), 2.45-2.37 (m, 6H), 1.99 (m, 2H), 1.64-1.56 (m, 4H), 1.47-1.40 (m, 2H).

Example 72

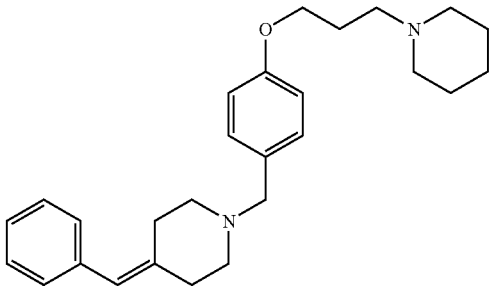

$K_i = 1.3$ nM

1-{3-[4-(4-Benzylidene-piperidin-1-ylmethyl)-phenoxy]-propyl}-piperidine

A solution of the product of Example 9 (204 mg), 4-Benzylidene-piperidine (145 mg), and acetic acid (0.05 mL) in DCM (3 mL) was treated with sodium triacetoxyborohydride (300 mg). After 16 h, the resulting mixture was treated with 10% sodium hydroxide (5 mL) and extracted with DCM (3×10 mL). The combined organic phases were dried (magnesium sulfate) and evaporated. Chromatography of the residue (1 to 5% 2 M methanolic ammonia/DCM) gave the title compound as a colorless oil (308 mg). $^1$H NMR (400 MHz, CDCl$_3$): 7.30 (m, 2H), 7.24-7.16 (m, 4H), 6.84 (m, 2H), 6.26 (s, 1H), 3.99 (t, J=6.3 Hz, 2H), 3.46 (s, 2H), 2.54-2.44 (m, 6H), 2.43-2.35 (m, 6H), 1.97 (m, 2H), 1.74 (br, 1H), 1.63-1.56 (m, 4H), 1.47-1.40 (m, 2H).

Example 73

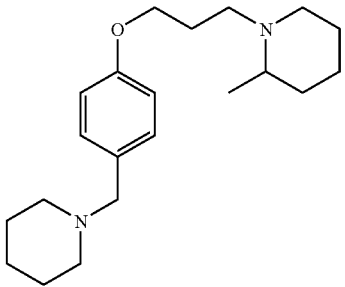

$K_i = 1.1$ nM

2-Methyl-1-[3-(4-piperidin-1-ylmethyl-phenoxy)-propyl]-piperidine

A suspension of the product of Example 17 (176 mg), 3-(2-methyl-piperidin-1-yl)-propan-1-ol (145 mg), and polymer supported triphenylphosphine (613 mg; loading: 3 mmol/g) in DCM (5 mL) was treated with di-tert-butylazodicarboxylate (316 mg). After 2 h, the resulting mixture was filtered, and the filtrate was evaporated. Chromatography of the residue (2.5% 2 M methanolic ammonia/DCM) gave the title compound as a colorless oil (60 mg). ¹H NMR (400 MHz, CDCl₃): 7.20 (d, J=8.6 Hz, 2H), 6.83 (d, J=8.6 Hz, 2H), 4.01-3.92 (m, 2H), 3.40 (s, 2H), 2.90-2.81 (m, 2H), 2.56-2.47 (m, 1H), 2.40-2.25 (m, 5H), 2.21-2.14 (m, 1H), 1.97-1.88 (m, 2H), 1.70-1.51 (m, 8H), 1.45-1.25 (m, 4H), 1.07 (d, J=6.2 Hz, 3H).

Example 74

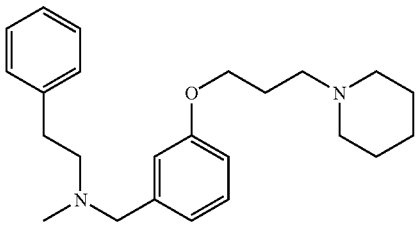

K_i = 3.0 nM

Methyl-phenethyl-[3-(3-piperidin-1-yl-propoxy)-benzyl]-amine

A solution of the product of Example 13 (103 mg), methyl-phenethyl-amine (56 mg), and acetic acid (0.03 mL) in DCM (2 mL) was treated with sodium triacetoxyborohydride (150 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (26 mg). ¹H NMR (400 MHz, CDCl₃): 7.30-7.25 (m, 2H), 7.22-7.16 (m, 4H), 6.87-6.84 (m, 2H), 6.78 (m, 1H), 3.97 (t, J=6.3 Hz, 2H), 3.52 (s, 2H), 2.82 (m, 2H), 2.64 (m, 2H), 2.48 (m, 2H), 2.40 (br, 4H), 2.28 (s, 3H), 1.97 (m, 2H), 1.63-1.56 (m, 4H), 1.47-1.40 (m, 2H).

Example 75

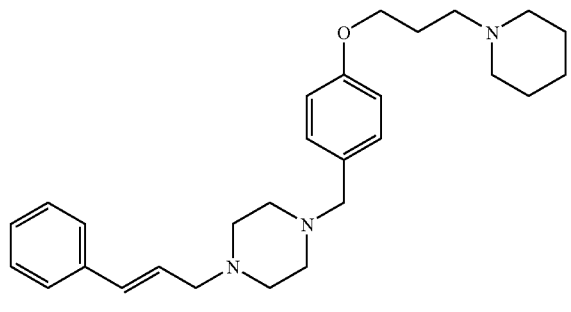

K_i = 1.6 nM 1-(3-Phenyl-allyl)-4-[4-(3-piperidin-1-yl-propoxy)-benzyl]-piperazine A solution of the product of Example 9 (215 mg), 1-(3-phenyl-allyl)-piperazine (176 mg), and acetic acid (0.06 mL) in DCM (3 mL) was treated with sodium triacetoxyborohydride (290 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (303 mg). ¹H NMR (400 MHz, CDCl₃): 7.36 (m, 2H), 7.30 (m, 2H), 7.24-7.18 (m, 3H), 6.83 (d, J=8.6 Hz, 2H), 6.51 (d, J=15.9 Hz, 1H), 6.31-6.23 (m, 1H), 3.98 (t, J=6.3 Hz, 2H), 3.45 (s, 2H), 3.15 (m, 2H), 2.60-2.32 (m, 12H), 1.67 (br, 1H), 1.62-1.56 (m, 4H), 1.47-1.40 (m, 2H).

Example 76

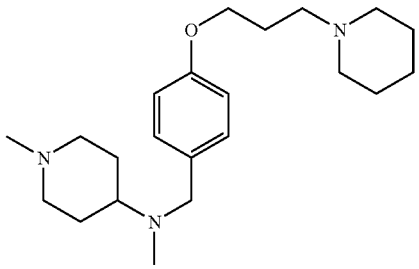

K_i = 1.1 nM

Methyl-(1-methyl-piperidin-4-yl)-[4-(3-piperidin-1-yl-propoxy)-benzyl]-amine

A solution of the product of Example 9 (227 mg), methyl-(1-methyl-piperidin-4-yl)-amine (118 mg), and acetic acid (0.06 mL) in DCM (3 mL) was treated with sodium triacetoxyborohydride (290 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (270 mg). ¹H NMR (400 MHz, CDCl₃): 7.19 (d, J=8.6 Hz, 2H), 6.83 (d, J=8.6 Hz, 2H), 3.98 (t, J=6.3 Hz, 2H), 3.49 (s, 2H), 2.90 (m, 2H), 2.78 (m, 2H), 2.46 (m, 2H), 2.43-2.35 (m, 4H), 2.26 (s, 3H), 2.17 (s, 3H), 2.00-1.87 (m, 5H), 1.78 (m, 2H), 1.68 (m, 2H), 1.61-1.54 (m, 4H), 1.47-1.40 (m, 2H).

Example 77

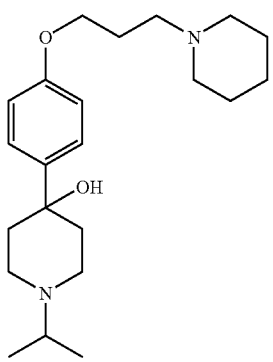

$K_i = 2.9$ nM

1-Isopropyl-4-[4-(3-piperidin-1-yl-propoxy)-phenyl]-piperidin-4-ol

A solution of the product of Example 5 (297 mg) in THF (2 mL) was cooled in a −78° C. bath and treated with a 1.6 M solution of butyllithium in hexanes (0.69 mL). After 1 h, a solution of 1-benzyl-piperidin-4-one (0.19 mL) in THF (1 mL) was added, and the mixture was allowed to warm to RT. After 1 h, water (2 mL) was added. The mixture was extracted with ether (2×2 mL), and the combined organic phases were dried (magnesium sulfate), and evaporated. Chromatography of the residue (3% 2 M methanolic ammonia/DCM) gave the title compound as an amorphous white solid (94 mg). $^1$H NMR (400 MHz, CDCl$_3$): 7.42 (d, J=9.0 Hz, 2H), 6.87 (d, J=9.0 Hz, 2H), 3.99 (t, J=6.5 Hz, 2H), 2.82-2.74 (m, 3H), 2.66-2.58 (m, 2H), 2.48-2.34 (m, 5H), 2.18-2.08 (m, 2H), 2.01-1.74 (m, 5H), 1.63-1.52 (m, 5H), 1.47-1.39 (m, 2H), 1.10 (d, J=6.7 Hz, 6H).

Example 78

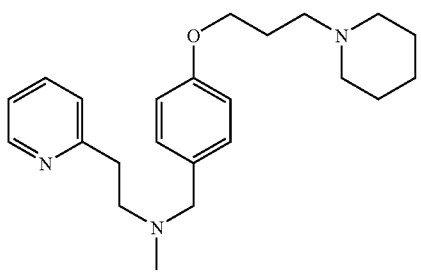

$K_i = 1.0$ nM

Methyl-[4-(3-piperidin-1-yl-propoxy)-benzyl]-(2-pyridin-2-yl-ethyl)-amine

A solution of the product of Example 9 (256 mg), methyl-(2-pyridin-2-yl-ethyl)-amine (143 mg), and acetic acid (0.06 mL) in DCM (4 mL) was treated with sodium triacetoxyborohydride (330 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (325 mg). $^1$H NMR (400 MHz, CDCl$_3$): 8.51 (m, 1H), 7.57 (m, 1H), 7.18-7.12 (m, 3H), 7.10 (m, 1H), 6.82 (d, J=8.6 Hz, 2H), 3.98 (t, J=6.3 Hz, 2H), 3.49 (s, 2H), 2.99 (m, 2H), 2.78 (m, 2H), 2.46 (m, 2H), 2.39 (br, 4H), 2.25 (s, 3H), 1.96 (m, 2H), 1.61-1.54 (m, 4H), 1.47-1.40 (m, 2H).

Example 79

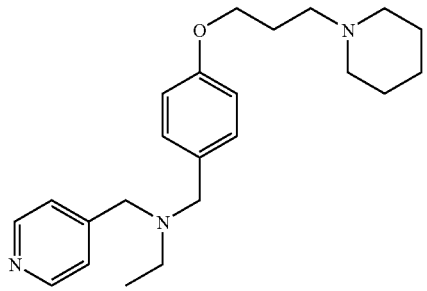

$K_i = 1.3$ nM

Ethyl-[4-(3-piperidin-1-yl-propoxy)-benzyl]-pyridin-4-ylmethyl-amine

A solution of the product of Example 9 (222 mg) ethyl-pyridin-4-ylmethyl-amine (122 mg), and acetic acid (0.06 mL) in DCM (3 mL) was treated with sodium triacetoxyborohydride (290 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (246 mg). $^1$H NMR (400 MHz, CDCl$_3$): 8.51 (m, 2H), 7.29 (m, 2H), 7.24 (m, 2H), 6.84 (d, J=8.6 Hz, 2H), 3.98 (t, J=6.3 Hz, 2H), 3.52 (s, 2H), 3.50 (s, 2H), 2.51-2.44 (m, 4H), 2.40 (br, 4H), 1.97 (m, 2H), 1.62-1.55 (m, 4H), 1.47-1.40 (m, 2H), 1.06 (t, J=7.0 Hz, 3H).

Example 80

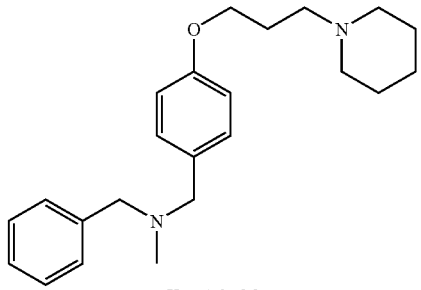

$K_i = 1.0$ nM

Benzyl-methyl-[4-(3-piperidin-1-yl-propoxy)-benzyl]-amine

A solution of the product of Example 9 (218 mg), benzyl methylamine (108 mg), and acetic acid (0.05 mL) in DCM (3 mL) was treated with sodium triacetoxyborohydride (300 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (269 mg). $^1$H NMR (400 MHz, CDCl$_3$): 7.37-7.28 (m, 4H), 7.27-7.22 (m, 5H), 6.85 (d, J=8.6 Hz, 2H), 3.99 (t, J=6.3 Hz, 2H), 3.49 (s, 2H), 3.45 (s, 2H), 2.50-2.31 (m, 6H), 2.16 (s, 3H), 1.97 (m, 2H), 1.62-1.55 (m, 4H), 1.47-1.40 (m, 2H).

Example 81

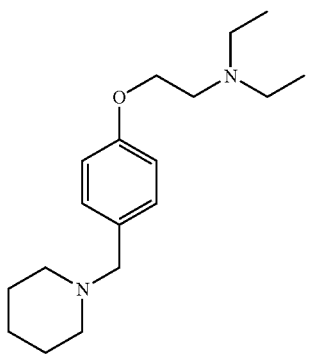

$K_i$ = 140 nM

Diethyl-[2-(4-piperidin-1-ylmethyl-phenoxy)-ethyl]-amine

A suspension of the product of Example 17 (176 mg), 2-Diethylamino-ethanol (0.12 mL), and polymer supported triphenylphosphine (613 mg; loading: 3 mmol/g) in DCM (5 mL) was treated with di-tert-butylazodicarboxylate (316 mg). After 2 h, the resulting mixture was filtered, and the filtrate was evaporated. Chromatography of the residue (3% 2 M methanolic ammonia/DCM) gave the title compound as a pale yellow oil (37 mg). $^1$H NMR (400 MHz, CDCl$_3$): 7.20 (d, J=8.8 Hz, 2H), 6.84 (d, J=8.6 Hz, 2H), 4.03 (t, J=6.5 Hz, 2H), 3.40 (s, 2H), 2.87 (t, J=6.5 Hz, 2H), 2.63 (q, J=7.0 Hz, 4H), 2.35 (br s, 4H), 1.59-1.52 (m, 4H), 1.46-1.37 (m, 2H), 1.07 (t, J=7.1 Hz, 6H).

Example 82

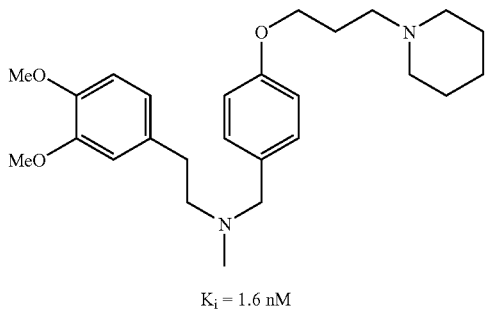

$K_i$ = 1.6 nM

[2-(3,4-Dimethoxy-phenyl)-ethyl]-methyl-[4-(3-piperidin-1-yl-propoxy)-benzyl]-amine A solution of the product of Example 9 (214 mg), [2-(3,4-dimethoxy-phenyl)-ethyl]-methyl-amine (170 mg), and acetic acid (0.05 mL) in DCM (3 mL) was treated with sodium triacetoxyborohydride (300 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (350 mg). $^1$H NMR (400 MHz, CDCl$_3$): 7.18 (d, J=8.6 Hz, 2H), 6.85-6.69 (m, 5H), 3.99 (t, J=6.3 Hz, 2H), 3.85 (s, 6H), 3.48 (s, 2H), 2.79-2.74 (m, 2H), 2.63-2.58 (m, 2H), 2.50-2.35 (m, 6H), 2.25 (s, 3H), 1.97 (m, 2H), 1.63-1.56 (m, 4H), 1.47-1.40 (m, 2H).

Example 83

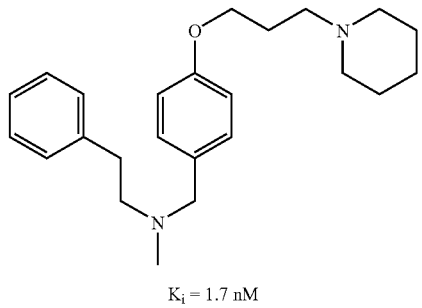

$K_i$ = 1.7 nM

Methyl-phenethyl-[4-(3-piperidin-1-yl-propoxy)-benzyl]-amine

A solution of the product of Example 9 (208 mg), methyl-phenethyl-amine (113 mg), and acetic acid (0.05 mL) in DCM (3 mL) was treated with sodium triacetoxyborohydride (290 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (300 mg). $^1$H NMR (400 MHz, CDCl$_3$): 7.30-7.25 (m, 2H), 7.21-7.16 (m, 5H), 6.83 (d, J=8.6 Hz, 2H), 3.99 (t, J=6.3 Hz, 2H), 3.49 (s, 2H), 2.84-2.79 (m, 2H), 2.65-2.62 (m, 2H), 2.51-2.37 (m, 6H), 2.26 (s, 3H), 1.98 (m, 2H), 1.63-1.56 (m, 4H), 1.47-1.40 (m, 2H).

Example 84

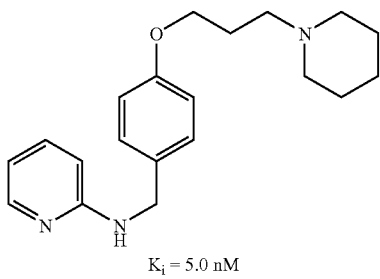

$K_i$ = 5.0 nM

[4-(3-Piperidin-1-yl-propoxy)-benzyl]-pyridin-2-yl-amine

A solution of the product of Example 9 (0.51 g), 2-aminopyridine (0.24 g), and acetic acid (0.12 mL) in DCM (7 mL) was treated with sodium triacetoxyborohydride (650 mg). After 16 h, the resulting mixture was treated with 10% sodium hydroxide (10 mL) and extracted with DCM (3×10 mL). The combined organic phases were dried (sodium sulfate) and evaporated. Chromatography of the residue (1-4% 2 M methanolic ammonia/DCM) gave the title compound as an off white solid (440 mg). $^1$H NMR (400 MHz, CDCl$_3$): 8.05 (m, 1H), 7.35 (m, 1H), 7.23 (d, J=8.6 Hz, 2H), 6.83 (d, J=8.6 Hz, 2H), 6.53 (m, 1H), 6.32 (m, 1H), 5.05 (m, 1H), 4.37 (d, J=5.6, 2H), 3.95 (t, J=6.3 Hz, 2H), 2.44 (m, 2H), 2.37 (br, 4H), 1.94 (m, 2H), 1.59-1.53 (m, 4H), 1.45-1.38 (m, 2H).

Example 85

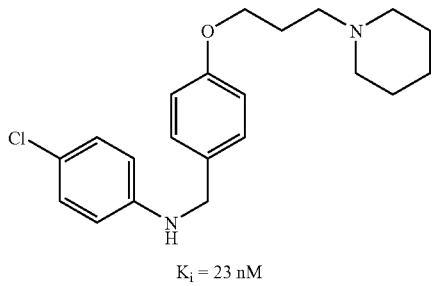

$K_i$ = 23 nM (4-Chloro-phenyl)-[4-(3-piperidin-1-yl-propoxy)-benzyl]-amine

A solution of the product of Example 9 (260 mg), 4-chloroaniline (180 mg), and acetic acid (0.06 mL) in DCE (3 mL) was treated with sodium triacetoxyborohydride (360 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (168 mg). $^1$H NMR (400 MHz, CDCl$_3$): 7.25 (d, J=8.8 Hz, 2H), 7.10 (d, J=8.9 Hz, 2H), 6.87 (d, J=8.8 Hz, 2H), 6.54 (d, J=8.9 Hz, 2H), 4.21 (d, J=4.7, 2H), 3.99 (t, J=6.3 Hz, 2H), 2.52-2.38 (m, 6H), 1.99 (m, 2H), 1.64-1.57 (m, 4H), 1.49-1.42 (m, 2H).

Example 86

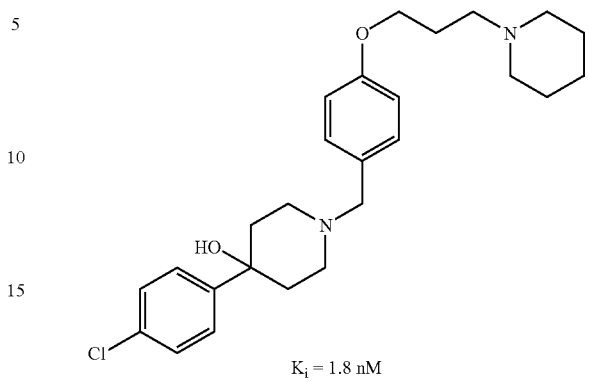

$K_i$ = 1.8 nM 4-(4-Chloro-phenyl)-1-[4-(3-piperidin-1-yl-propoxy)-benzyl]-piperidin-4-ol A solution of the product of Example 9 (200 mg), 4-(4-chloro-phenyl)-piperidin-4-ol (170 mg), and acetic acid (0.05 mL) in DCM (3 mL) was treated with sodium triacetoxyborohydride (300 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (203 mg). $^1$H NMR (400 MHz, CDCl$_3$): 7.46-7.42 (m, 2H), 7.32-7.28 (m, 2H), 7.25-7.22 (m, 2H), 6.87-6.84 (m, 2H), 3.99 (t, J=6.3 Hz, 2H), 3.51 (s, 2H), 2.78 (m, 2H), 2.51-2.36 (m, 8H), 2.11 (m, 2H), 1.98 (m, 2H), 1.69 (m, 2H), 1.63-1.56 (m, 4H), 1.48-1.40 (m, 2H).

Example 87

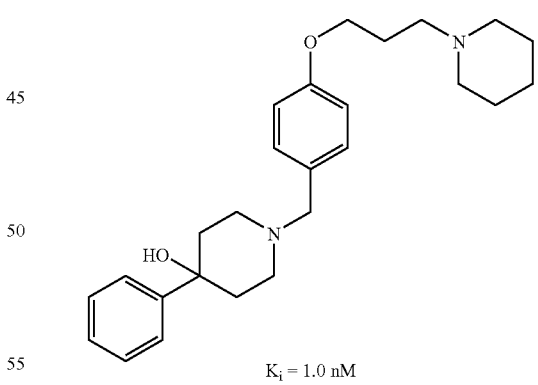

$K_i$ = 1.0 nM

4-Phenyl-1-[4-(3-piperidin-1-yl-propoxy)-benzyl]-piperidin-4-ol

A solution of the product of Example 9 (210 mg), 4-Phenyl-piperidin-4-ol (150 mg), and acetic acid (0.05 mL) in DCM (3 mL) was treated with sodium triacetoxyborohydride (290 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (225 mg). $^1$H NMR (400 MHz, CDCl$_3$): 7.54-7.49 (m, 2H), 7.37-7.33 (m, 2H), 7.28-7.23 (m, 3H), 6.88-6.84 (m, 2H), 3.99 (t, J=6.3 Hz, 2H), 3.51 (s, 2H), 2.78 (m, 2H), 2.50-2.36 (m, 8H), 2.15 (m, 2H), 1.97 (m, 2H), 1.73 (m, 2H), 1.63-1.55 (m, 4H), 1.47-1.40 (m, 2H).

Example 88

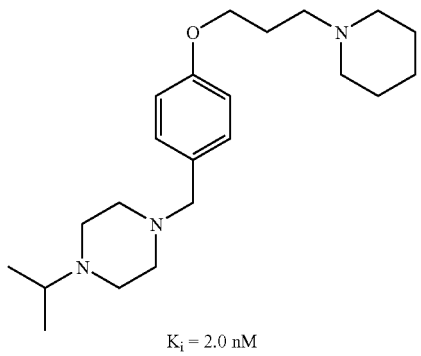

$K_i$ = 2.0 nM

1-Isopropyl-4-[4-(3-piperidin-1-yl-propoxy)-benzyl]-piperazine

A solution of the product of Example 9 (200 mg), 1-isopropyl-piperazine (100 mg), and acetic acid (0.05 mL) in DCM (3 mL) was treated with sodium triacetoxyborohydride (290 mg). After 16 h, the resulting mixture was treated with 10% sodium hydroxide (5 mL) and extracted with DCM (3×10 mL). The combined organic phases were dried (sodium sulfate) and evaporated. Chromatography of the residue (1-5% 2 M methanolic ammonia/DCM) gave the title compound as a colorless oil (225 mg). $^1$H NMR (400 MHz, CDCl$_3$): 7.19 (d, J=8.6 Hz, 2H), 6.83 (d, J=8.6 Hz, 2H), 3.98 (t, J=6.6 Hz, 2H), 3.43 (s, 2H), 2.63 (m, 1H), 2.53 (br, 4H), 2.46 (m, 4H), 2.39 (br, 4H), 1.96 (m, 2H), 1.58 (m, 4H), 1.46-1.40 (m, 2H), 1.03 (d, J=6.5 Hz, 6H).

Example 89

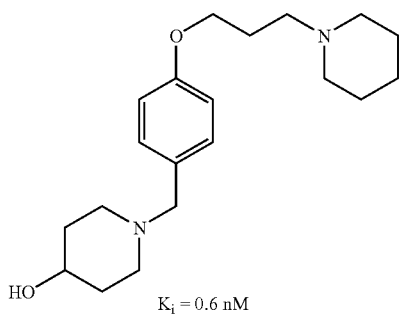

$K_i$ = 0.6 nM

1-[4-(3-Piperidin-1-yl-propoxy)-benzyl]-piperidin-4-ol

A solution of the product of Example 9 (175 mg), 4-hydroxypiperidine (79 mg), and acetic acid (0.01 mL) in DCE (3 mL) was treated with sodium triacetoxyborohydride (231 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (6% 2 M methanolic ammonia/DCM) gave the title compound as a white crystalline solid (63 mg). $^1$H NMR (400 MHz, CDCl$_3$): 7.19 (d, J=8.6 Hz, 2H), 6.84 (d, J=8.6 Hz, 2H), 3.99 (t, J=6.5 Hz, 2H), 3.71-3.62 (m, 1H), 3.43 (s, 2H), 2.77-2.69 (m, 2H), 2.49-2.34 (m, 6H), 2.15-2.05 (m, 2H), 2.01-1.92 (m, 2H), 1.91-1.82 (m, 2H), 1.76 (br s, 1H), 1.62-1.52 (m, 6H), 1.47-1.40 (m, 2H).

Example 90

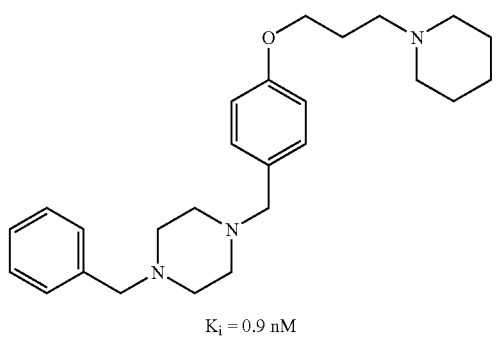

$K_i$ = 0.9 nM

1-Benzyl-4-[4-(3-piperidin-1-yl-propoxy)-benzyl]-piperazine

A solution of the product of Example 9 (175 mg), 1-benzylpiperazine (0.14 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (2% 2 M methanolic ammonia/DCM) gave the title compound as a white solid (63 mg). $^1$H NMR (400 MHz, CDCl$_3$): 7.32-7.17 (m, 7H), 6.83 (d, J=8.6 Hz, 2H), 3.98 (t, 6.4 Hz, 2H), 3.50 (s, 2H), 3.44 (s, 2H), 2.52-2.35 (m, 14H), 2.00-1.92 (m, 2H), 1.62-1.55 (m, 4H), 1.47-1.39 (m, 2H).

Example 91

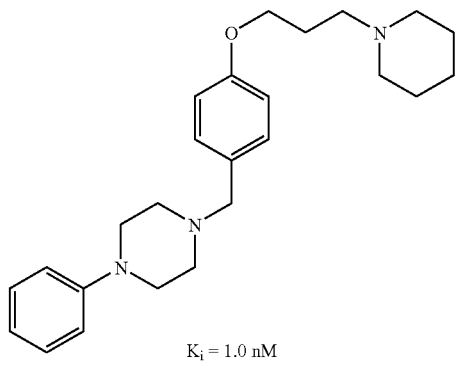

$K_i$ = 1.0 nM

1-Phenyl-4-[4-(3-piperidin-1-yl-propoxy)-benzyl]-piperazine

A solution of the product of Example 9 (175 mg), 1-phenylpiperazine (0.12 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (2% 2 M methanolic ammonia/DCM) gave the title compound as a white solid (70 mg). $^1$H NMR (400 MHz, CDCl$_3$): 7.28-7.22 (m, 4H), 6.94-6.81 (m, 5H), 4.00 (t, J=6.5 Hz, 2H), 3.50 (s, 2H), 3.21-3.16 (m, 4H), 2.61-2.56 (m, 4H), 2.50-2.35 (m, 6H), 2.02-1.94 (m, 2H), 1.63-1.56 (m, 4H), 1.48-1.40 (m, 2H).

Example 92

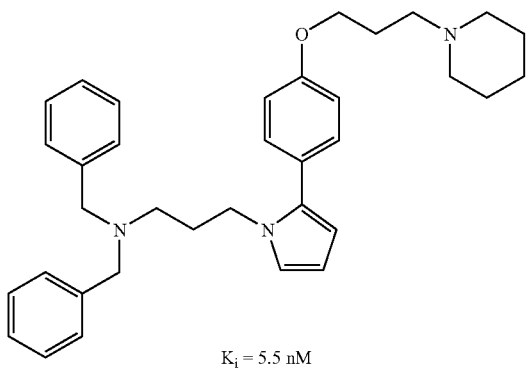

$K_i = 5.5$ nM

Dibenzyl-(3-{2-[4-(3-piperidin-1-yl-propoxy)-phenyl]-pyrrol-1-yl}-propyl)-amine To a stirred suspension of sodium hydride (0.14 g) in DMF (9 mL) at RT was added dropwise a solution of the product of Example 18 (1 g) in DMF (9 mL). After 20 min, 1-(3-bromopropyl)-2,2,5,5-tetramethyl-1-aza-2,5-disilacyclopentane (0.876 mL) was added dropwise. After 20 min, the mixture was carefully treated with water (30 mL) and then extracted several times with methylene chloride. The combined organic layers were washed with brine, dried (sodium sulfate), filtered, and concentrated under reduced, giving a dark red oil (1.2 g). To a solution of this oil (0.211 g) in dichloroethane (6 mL) was added benzaldehyde (0.138 mL), acetic acid (0.138 mL), and sodium triacetoxyborohydride (0.367 g). The mixture was stirred for 12 h at RT and then diluted with methylene chloride and saturated aqueous sodium bicarbonate solution. The organic layer was separated and the aqueous layer extracted with several portions of methylene chloride. The combined organic layers were washed with brine, dried (sodium sulfate), filtered and concentrated under reduced pressure to give an orange oil (0.289 g). Silica gel chromatography (2% methanol/ethyl acetate) afforded the title compound as a yellow oil (0.103 g). $^1$H NMR (400 MHz, MeOH-d$_4$): 7.30-7.17 (m, 12H), 6.90-6.86 (m, 2H), 6.58-6.57 (m, 1H), 6.01 (t, 3 Hz, 1H), 5.97-5.95 (m, 1H), 3.95 (t, J=6.3 Hz, 2H), 3.88 (t, J=7.6 Hz, 2H), 3.37 (s, 4H), 2.55-2.4 (m, 6H), 2.29 (t, J=6.6 Hz, 2H), 2.02-1.95 (m, 2H), 1.75-1.68 (m, 2H), 1.66-1.58 (m, 4H), 1.53-1.43 (m, 2H).

Example 93

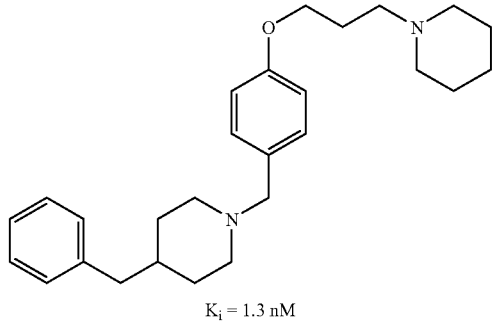

$K_i = 1.3$ nM

1-{3-[4-(4-Benzyl-piperidin-1-ylmethyl)-phenoxy]-propyl}-piperidine

A solution of the product of Example 9 (175 mg), 4-benzylpiperidine (0.14 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (1.5% 2 M methanolic ammonia/DCM) gave the title compound as a colorless oil (97 mg). $^1$H NMR (400 MHz, CDCl$_3$): 7.29-7.10 (m, 7H), 6.81 (d, J=8.3 Hz, 2H), 3.99 (t, J=6.3 Hz, 2H), 3.40 (s, 2H), 2.86-2.81 (m, 2H), 2.54-2.44 (m, 4H), 2.00-1.81 (m, 4H), 1.65-1.40 (m, 13H), 1.35-1.23 (m, 2H).

Example 94

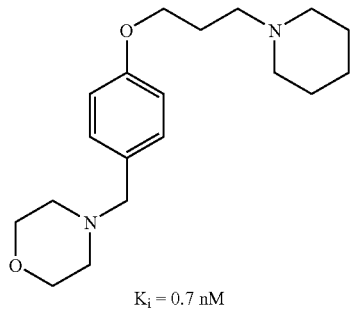

$K_i = 0.7$ nM

4-[4-(3-Piperidin-1-yl-propoxy)-benzyl]-morpholine

A solution of the product of Example 9 (175 mg), morpholine (0.07 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (3.5% 2 M methanolic ammonia/DCM) gave the title compound as a colorless oil (145 mg). $^1$H NMR (400 MHz, CDCl$_3$): 7.21 (d, J=8.6 Hz, 2H), 6.85 (d, J=8.6 Hz, 2H), 3.99 (t, J=6.4 Hz, 2H), 3.71-3.67 (m, 4H), 3.42 (s, 2H), 2.50-2.36 (m, 10H), 2.01-1.93 (m, 2H), 1.63-1.56 (m, 4H), 1.49-1.40 (m, 2H).

Example 95

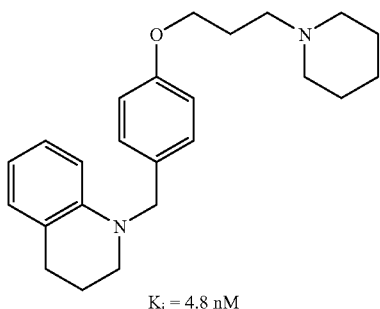

$K_i$ = 4.8 nM

1-[4-(3-Piperidin-1-yl-propoxy)-benzyl]-1,2,3,4-tetrahydro-quinoline

A solution of the product of Example 9 (175 mg), 1,2,3,4-tetrahydro-quinoline (0.10 mL), and acetic acid (0.09 mL) in DCE (3 mL) was treated with sodium triacetoxyborohydride (210 mg). After 16 h, the resulting mixture was treated with 10% sodium hydroxide (1 mL) and extracted with DCM (3×3 mL). The combined organic phases were dried (magnesium sulfate) and evaporated. Chromatography of the residue (1.5% 2 M methanolic ammonia/DCM) gave the title compound as a colorless oil (77 mg). $^1$H NMR (400 MHz, CDCl$_3$): 7.13 (d, J=8.8 Hz, 2H), 6.96 (t, J=7.3 Hz, 2H), 6.83 (d, J=8.8 Hz, 2H), 6.58-6.51 (m, 2H), 4.40 (s, 2H), 3.97 (t, J=6.3 Hz, 2H), 3.32 (dd, J=5.7, 5.7 Hz, 2H), 2.79 (t, J=6.3 Hz, 2H), 2.50-2.35 (m, 6H), 2.02-1.92 (m, 4H), 1.62-1.55 (m, 4H), 1.47-1.39 (m, 2H).

Example 96

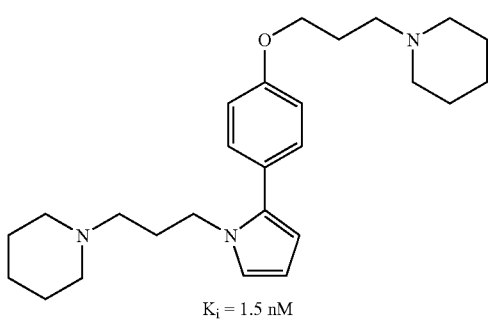

$K_i$ = 1.5 nM 1-(3-{4-[1-(3-Piperidin-1-yl-propyl)-1H-pyrrol-2-yl]-phenoxy}-propyl)-piperidin To a stirred suspension of sodium hydride (0.051 g) in DMF (3 mL) at RT was added dropwise the product of Example 18 (0.2 g) in DMF (4 mL). After 20 min, 1-(3-chloro-propyl)-piperdine (0.139 g) was added dropwise and the mixture stirred for 12 h. The mixture was diluted with water and extracted several times with diethyl ether. The combined organic layers were washed with brine, dried (sodium sulfate), filtered and concentrated under reduced pressure, giving the title compound as a dark red oil (0.257 g). $^1$H NMR (400 MHz, C$_6$D$_6$): 7.35 (d, J=8.8 Hz, 2H), 6.90 (d, J=8.8 Hz, 2H), 6.72 (t, J=2.5 Hz, 1H), 6.44 (d, J=2.5 Hz), 3.82 (m, 4H), 2.37-2.16 (m, 8H), 2.06 (br s, 4H), 1.96 (t, J=6.6 Hz, 2H), 1.87-1.81 (m, 2H), 1.59-1.22 (m, 16H).

Example 97

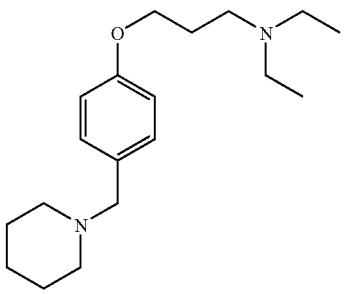

Diethyl-[3-(4-piperidin-1-ylmethyl-phenoxy)-propyl]-amine

A suspension of the product of Example 17 (176 mg), 3-diethylaminolpropan-1-ol (0.14 mL), and polymer-supported triphenylphosphine (613 mg, 3 mmol/g phosphorus content) in dichloromethane (4 mL) was treated with a solution of di-tert-butyl azodicarboxylate (318 mg) in dichloromethane (1 mL). The resulting mixture was stirred for 3 h and filtered. Chromatography of the filtrate (0-8% 2M methanolic ammonia/dichloromethane) gave the title compound as a pale yellow oil (130 mg). $^1$H NMR (400 MHz, CDCl$_3$): 7.20 (d, J=8.6 Hz, 2H), 6.82 (d, J=8.6 Hz, 2H), 3.98 (t, J=3.98 Hz, 2H), 3.42 (s, 2H), 2.64-2.52 (m, 6H), 2.41-2.33 (m, 4H), 1.96-1.86 (m, 2H), 1.59-1.53 (m, 4H), 1.44-1.38 (m, 2H).1.04 (t, J=7.2 Hz, 6H).

Example 98

Biological Methods

In Vitro

Transfection of Cells with Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% CO$_2$ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 μL complete media and transferred to an electroporation cuvette with a 0.4 cm gap between the electrodes (Bio-Rad #165-2088). One microgram of supercoiled H$_3$ receptor cDNA was added to the cells and mixed. The voltage for the electroporation was set at 0.25 kV, the capacitance was set at 960 μF. After electroporation the cells were diluted into 10 mL complete media and plated onto four 10 cm dishes. Because of the variability in the efficiency of electroporation, four different concentrations of cells were plated. The ratios used were; 1:20, 1:10, 1:5, with the remainder of the cells being added to the fourth dish. The cells were allowed to recover for 24 hours before adding the selection media (complete media with 600 μg/mL G418). After 10 days dishes were analyzed for surviving colonies of cells. Dishes with well isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

[$^3$H]-N-methylhistamine Binding

Cell pellets from histamine $H_3$ receptor-expressing SK-N-MC cells were homogenized in 20 mM TrisHCl/0.5 mM EDTA. Supernatants from a 800 g spin were collected, recentrifuged at 30,000 g for 30 minutes. Pellets were re-homogenized in 50 mM Tris/5 mM EDTA (pH 7.4). Membranes were incubated with 0.8 nM [$^3$H]-N-methylhistamine plus/minus test compounds for 45 min at 25° C. and harvested by rapid filtration over GF/C glass fiber filters (pretreated with 0.3% polyethylenimine) followed by four washes with ice cold buffer. Filters were dried, added to 4 mL scintillation cocktail and then counted on a liquid scintillation counter. Non-specific binding was defined with 10 μM histamine. The $pK_i$ values were calculated based on a $K_d$ of 800 pM and a ligand concentration ([L]) of 800 pM according to the formula:

$$K_i = (IC_{50})/(1+([L]/(K_d)))$$

In Vivo

Elucidation of Oral Absorption and Blood-Brain Barrier Penetration Profiles of $H_3$ Receptor Antagonists in the Rat A rat in vivo system was used to determine the blood-brain barrier penetration profiles and kinetics of various $H_3$ receptor antagonists after single bolus oral administration.

Female Sprague Dawley Rats (~300 gram body weight) were housed in accordance with institutional standards and allowed to acclimate for at least 7 days prior to the study. Each $H_3$ antagonist was formulated in 0.5% hydroxypropylmethyl cellulose at a concentration of 1 mg/mL for oral dosing. The test compound was administered to each of eight animals as a single oral dose of 10 mL/kg (10 mg/kg). Remaining dosing solution was retained for analysis. Two animals from each original group of eight were euthanized via $CO_2$ asphyxiation at t=1, 6, 24, and 48 hours. After each animal was euthanized, 0.1 mL of its blood was sampled via cardiac puncture, and its brain was removed via dissection of the cranial bones and placed in a pre-weighed 50 mL conical tube on dry ice.

The blood was added to 0.3 mL of 6% trichloroacetic acid, and the acidified sample was vortexed and then centrifuged (5 minutes at 14,000 rpm in a microcentrifuge). The clear supernatant was retained for analysis. The frozen brain was weighed, homogenized in 6% trichloroacetic acid (3 mL/g wet weight of tissue), and then centrifuged. The clear supernatant was retained for analysis. The supernatants from the blood and brain samples were analyzed by liquid chromatography with mass spectral detection utilizing selective reaction monitoring (LC-MS/MS). The LC method used a Phenomonex Polar RP column (2×50 mm) and a linear solvent gradient of water and acetonitrile (both 1% in acetic acid).

Graphs of $H_3$ receptor antagonist concentration versus time for blood and brain were generated from the LC-MS/MS results. The mean residency time (MRT) of the $H_3$ receptor antagonist, in blood or in the brain, was calculated from the ratio of the area under the first moment curve (AUMC) to the area under the, concentration time curve (AUC): AUMC/AUC. The Blood Brain Barrier index was calculated from the log of $AUC_{brain}/AUC_{blood}$.

F. OTHER EMBODIMENTS

The features and advantages of the invention will be apparent to one of ordinary skill in view of the discussion, examples, embodiments, and claims relating to the invention. The invention also contemplates variations and adaptations, based on the disclosure herein concerning the key features and advantages of the invention, and within the abilities of one of ordinary skill.

What is claimed is:
1. A compound of formula (I):

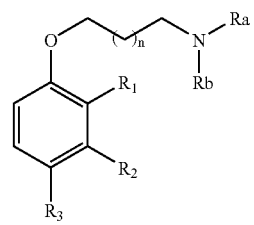

wherein $R_a$ and $R_b$ taken together with the nitrogen to which they are attached form a piperidyl or pyrrolidinyl group;

n is 0-4;

$R_1$ and $R_2$ are independtly hydrogen or halo and $R_3$ is G;

G is a 5 or 6 member heterocyclic ring of formula (iii)

wherein:

$L_6$ is $C_{1-2}$ alkylene;

$L_7$ is $C_{1-2}$ alkylene or absent;

$R_7$ is H, hydroxyl, halo, $C_{2-6}$ alkoxy or absent where the carbon linking $L_6$ and $L_7$ (or bonded to $R_6$) participates in a double bond;

$R_{10}$ is H, $C_{1-8}$ alkyl, $C_{3-8}$ alkenyl, $C_{3-7}$ cycloalkyl, ($C_{3-7}$ cycloalkyl)$C_{1-6}$ alkylene, ($C_{2-15}$ heterocyclyl)$C_{1-6}$ alkylene, or (phenyl)$C_{1-6}$ alkylene;

wherein each of the above alkyl, alkylene, alkenyl, heterocyclyl, and cycloalkyl groups may each be independently and optionally substituted with between 1 and 3 substituents selected from halo, amino, nitro, hydroxyl, and $C_{1-3}$ alkyl;

or a pharmaceutically acceptable salt, ester, or amide thereof.

2. A compound of claim 1, wherein n is 1.

3. A compound of claim 1, wherein $R_{10}$ is H, branched $C_{3-6}$ alkyl, or benzyl.

4. A compound of claim 3, wherein $R_{10}$ is isopropyl or benzyl.

5. A compound of claim 1, selected from: 1-{3-[4-(1-Methyl-pyrrolidin-2-yl)-phenoxy]-propyl}-piperidine, and 1-Benzyl-4-[4-(3-piperidin-1-yl-propoxy)-phenyl]-piperidin-4-ol.

6. A pharmaceutical composition comprising a compound of claim 1, and a pharmaceutically-acceptable excipient.

7. A compound of claim 1, isotopically-labelled to be detectable by PET or SPECT.

* * * * *